(12) United States Patent
Nguyen et al.

(10) Patent No.: US 11,033,763 B2
(45) Date of Patent: Jun. 15, 2021

(54) RESPIRATOR INCLUDING POLYMERIC NETTING AND METHOD OF FORMING SAME

(71) Applicant: 3M INNOVATIVE PROPERTIES COMPANY, St. Paul, MN (US)

(72) Inventors: Nhat Ha Thi Nguyen, Woodbury, MN (US); Thomas J. Xue, Woodbury, MN (US); Seyed A. Angadjivand, Los Angeles, CA (US); Ronald W. Ausen, St. Paul, MN (US); William J. Kopecky, Hudson, WI (US); Mark T. Gibson, Stillwater, MN (US); Olof N. Hansson, Varnamo (SE); Joseph P. Kronzer, Shoreview, MN (US)

(73) Assignee: 3M Innovative Properties Company, St. Paul, MN (US)

( * ) Notice: Subject to any disclaimer, the term of this patent is extended or adjusted under 35 U.S.C. 154(b) by 877 days.

(21) Appl. No.: 15/503,732

(22) PCT Filed: Aug. 12, 2015

(86) PCT No.: PCT/US2015/044748
§ 371 (c)(1),
(2) Date: Feb. 14, 2017

(87) PCT Pub. No.: WO2016/028553
PCT Pub. Date: Feb. 25, 2016

(65) Prior Publication Data
US 2017/0274228 A1 Sep. 28, 2017

Related U.S. Application Data

(60) Provisional application No. 62/038,455, filed on Aug. 18, 2014.

(51) Int. Cl.
*A62B 23/02* (2006.01)
*A62B 18/08* (2006.01)
(Continued)

(52) U.S. Cl.
CPC .......... *A62B 23/025* (2013.01); *A41D 13/113* (2013.01); *A41D 13/1138* (2013.01);
(Continued)

(58) Field of Classification Search
CPC ..... A62B 23/025; A62B 18/084; A62B 18/00; A62B 18/02; A62B 18/025; A41D 13/11;
(Continued)

(56) References Cited

U.S. PATENT DOCUMENTS 2,489,277 A 11/1945 Faralla
3,082,767 A 3/1963 Matheson
(Continued)

FOREIGN PATENT DOCUMENTS

| AU | 2014101151 | 12/2014 |
| CN | 2704338 | 6/2005 |

(Continued)

OTHER PUBLICATIONS

Davies, "The Separation of Airborne Dust Particles", Institution of Mechanical Engineers Proceedings, vol. 1B, No. 1-12, 1952, pp. 185-198.
(Continued)

*Primary Examiner* — Ophelia A Hawthorne
*Assistant Examiner* — Caitlin A Carreiro

(57) ABSTRACT

One or more embodiments of a respirator that includes a polymeric netting is disclosed. The respirator can include a mask body including a perimeter, a harness attached to the mask body, and a face seal disposed adjacent at least a portion of the perimeter of the mask body. In one or more embodiments, the face seal includes a polymeric netting
(Continued)

including polymeric ribbons and polymeric strands, where each of the polymeric ribbons and strands having a length, width, and height, where the length is the longest dimension, the width is the shortest dimension, and the height is the dimension transverse to the length and the width. The polymeric ribbons have a height-to-width aspect ratio of at least 5 to 1, a major surface that is intermittently bonded to only one polymeric strand, and a height that is at least two times greater than a height of the one polymeric strand.

15 Claims, 33 Drawing Sheets

(51) Int. Cl.
  *A41D 13/11* (2006.01)
  *A61F 11/14* (2006.01)
  *B29D 28/00* (2006.01)
  *A62B 18/02* (2006.01)
  *A61F 5/01* (2006.01)

(52) U.S. Cl.
  CPC ........ *A41D 13/1176* (2013.01); *A61F 5/0104* (2013.01); *A61F 11/14* (2013.01); *A62B 18/025* (2013.01); *A62B 18/084* (2013.01); *B29D 28/00* (2013.01)

(58) Field of Classification Search
  CPC ............ A41D 13/1115; A41D 13/1138; A41D 13/1123; A41D 13/113; A41D 13/1176; A41D 13/1173; A61M 16/06; A61M 16/047; A61F 5/0104; A61F 11/14; B29D 28/00
  USPC ........... 128/206.12, 206.19, 206.21, 206, 28, 128/207.11, 205, 29 M, 205.25, 206.24, 128/863, 857, 858, 206.23; D24/110, D24/110.1; 602/17, 74; 2/410, 8.2, 428
  See application file for complete search history.

(56) References Cited

U.S. PATENT DOCUMENTS

| | | |
|---|---|---|
| 3,471,588 A | 10/1969 | Kanner |
| 3,506,980 A | 4/1970 | Aileo |
| 3,521,630 A | 7/1970 | Westberg |
| RE28,102 E | 8/1974 | Mayhew |
| 3,971,373 A | 7/1976 | Braun |
| 4,013,816 A | 3/1977 | Sabee |
| 4,215,682 A | 8/1980 | Kubik |
| 4,300,549 A | 11/1981 | Parker |
| 4,381,326 A | 4/1983 | Kelly |
| RE31,285 E | 6/1983 | van Turnhout |
| 4,419,993 A | 12/1983 | Petersen |
| 4,419,994 A | 12/1983 | Hilton |
| 4,454,881 A | 6/1984 | Huber |
| 4,536,440 A | 8/1985 | Berg |
| 4,564,009 A | 1/1986 | Brinkhoff |
| 4,588,537 A | 5/1986 | Klaase |
| 4,634,485 A * | 1/1987 | Welygan ............... B29C 48/05 156/244.11 |
| 4,790,306 A | 12/1988 | Braun |
| 4,798,850 A | 1/1989 | Brown |
| 4,802,473 A | 2/1989 | Hubbard |
| 4,807,619 A | 2/1989 | Dyrud |
| 4,827,924 A | 5/1989 | Japuntich |
| 4,850,347 A | 7/1989 | Skov |
| 4,873,972 A | 10/1989 | Magidson |
| 4,937,147 A * | 6/1990 | Cartier ............... B32B 17/10761 428/425.3 |
| 4,958,697 A | 9/1990 | Moody |
| 5,052,084 A | 10/1991 | Braun |
| 5,237,986 A | 8/1993 | Seppala |
| 5,307,796 A | 5/1994 | Kronzer |
| 5,325,892 A | 7/1994 | Japuntich |
| 5,429,126 A | 7/1995 | Bracken |
| 5,496,507 A | 3/1996 | Angadjivand |
| 5,558,089 A | 9/1996 | Castiglione |
| D378,610 S | 3/1997 | Reischel |
| 5,656,368 A | 8/1997 | Braun |
| 5,803,077 A | 9/1998 | Gazzara |
| 5,804,295 A | 9/1998 | Braun |
| 5,817,704 A | 10/1998 | Shiveley |
| 5,885,686 A | 3/1999 | Cederblad |
| 5,908,598 A | 6/1999 | Rousseau |
| 5,920,911 A | 7/1999 | Cushman |
| D412,573 S | 8/1999 | Castiglione |
| 5,948,517 A | 9/1999 | Adamko |
| D421,118 S | 2/2000 | Reischel |
| 6,041,782 A | 3/2000 | Angadjivand |
| 6,062,221 A | 5/2000 | Brostrom |
| 6,070,579 A | 6/2000 | Bryant |
| 6,123,077 A | 9/2000 | Bostock |
| 6,129,175 A | 10/2000 | Tutor |
| 6,228,449 B1 | 5/2001 | Meyer |
| 6,234,171 B1 | 5/2001 | Springett |
| D443,927 S | 6/2001 | Chen |
| 6,277,178 B1 | 8/2001 | Hilmquist-Brown |
| D448,472 S | 9/2001 | Chen |
| 6,332,465 B1 | 12/2001 | Xue |
| 6,334,671 B1 | 1/2002 | Umehara |
| 6,348,249 B2 | 2/2002 | Meyer |
| 6,375,886 B1 | 4/2002 | Angadjivand |
| 6,391,420 B1 | 5/2002 | Cederblad |
| 6,391,429 B1 | 5/2002 | Senkus |
| 6,394,090 B1 | 5/2002 | Chen |
| D458,364 S | 6/2002 | Curran |
| D459,471 S | 6/2002 | Curran |
| 6,397,458 B1 | 6/2002 | Jones |
| 6,398,847 B1 | 6/2002 | Jones |
| 6,406,657 B1 | 6/2002 | Eitzman |
| 6,409,806 B1 | 6/2002 | Jones |
| 6,436,529 B1 | 8/2002 | Deeb |
| 6,454,986 B1 | 9/2002 | Eitzman |
| 6,457,473 B1 | 10/2002 | Brostrom |
| 6,465,107 B1 | 10/2002 | Kelly |
| 6,484,722 B2 | 11/2002 | Bostock |
| D467,656 S | 12/2002 | Mittelstadt |
| 6,492,286 B1 | 12/2002 | Berrigan |
| RE37,974 E | 2/2003 | Bower |
| D471,627 S | 3/2003 | Mittelstadt |
| 6,568,392 B1 | 5/2003 | Bostock |
| 6,591,837 B1 | 7/2003 | Byram |
| 6,715,489 B2 | 4/2004 | Bostock |
| 6,715,490 B2 | 4/2004 | Byram |
| 6,722,366 B2 | 4/2004 | Bostock |
| 6,732,733 B1 | 5/2004 | Brostrom |
| 6,743,464 B1 | 6/2004 | Insley |
| 6,783,574 B1 | 8/2004 | Angadjivand |
| 6,824,718 B2 | 11/2004 | Eitzman |
| 6,843,248 B2 | 1/2005 | Japuntich |
| 6,854,463 B2 | 2/2005 | Japuntich |
| 6,874,499 B2 | 4/2005 | Viner |
| 6,883,518 B2 | 4/2005 | Mittelstadt |
| 6,923,182 B2 | 8/2005 | Angadjivand |
| 7,013,895 B2 | 3/2006 | Martin |
| D518,571 S | 4/2006 | Martin |
| 7,028,689 B2 | 4/2006 | Martin |
| 7,117,868 B1 | 10/2006 | Japuntich |
| 7,131,442 B1 | 11/2006 | Kronzer |
| RE39,493 E | 2/2007 | Yuschak |
| 7,188,622 B2 | 3/2007 | Martin |
| 7,210,484 B1 | 5/2007 | Tiemens |
| 7,302,951 B2 | 12/2007 | Mittelstadt |
| 7,311,104 B2 | 12/2007 | Japuntich |
| 7,428,903 B1 | 9/2008 | Japuntich |
| 7,594,510 B2 | 9/2009 | Betz |
| 7,650,884 B2 | 1/2010 | Flannigan |
| D613,850 S | 4/2010 | Holmquist-Brown |
| 7,757,334 B2 | 7/2010 | Patel |
| 7,897,078 B2 | 3/2011 | Petersen |
| 8,066,006 B2 | 11/2011 | Daugaard |

(56) References Cited

U.S. PATENT DOCUMENTS

| | | |
|---|---|---|
| 8,067,110 B2 | 11/2011 | Rakow |
| D652,507 S | 1/2012 | Mittelstadt |
| 8,113,201 B2 | 2/2012 | Steindorf |
| D659,821 S | 5/2012 | Spoo |
| 8,302,731 B2 | 11/2012 | Nilsson |
| 8,596,224 B2 | 12/2013 | Taylor |
| 8,640,704 B2 | 2/2014 | Spoo |
| 8,733,711 B2 | 5/2014 | Fristoe |
| 8,800,563 B2 | 8/2014 | Doherty |
| 2004/0163653 A1 | 8/2004 | Fleming |
| 2004/0163882 A1 | 8/2004 | Fleming |
| 2004/0214489 A1 | 10/2004 | Porter |
| 2005/0081857 A1 | 4/2005 | Fenton |
| 2005/0238181 A1 | 10/2005 | Nilsson |
| 2006/0001464 A1 | 1/2006 | Yokozeki |
| 2006/0062416 A1 | 3/2006 | Wu |
| 2006/0072005 A1 | 4/2006 | Thomas-Wayne |
| 2006/0266364 A1 | 11/2006 | Turdjian |
| 2007/0000499 A1 | 1/2007 | Buck |
| 2007/0044803 A1 | 3/2007 | Xue |
| 2007/0068529 A1 | 3/2007 | Kalatoor |
| 2007/0136967 A1 | 6/2007 | Tochacek |
| 2007/0157388 A1 | 7/2007 | Mossbeck |
| 2007/0251522 A1 | 11/2007 | Welchel |
| 2008/0023006 A1 | 1/2008 | Kalatoor |
| 2008/0029892 A1 | 2/2008 | Jung |
| 2008/0099022 A1 | 5/2008 | Gebrewold |
| 2008/0128198 A1 | 6/2008 | Du |
| 2008/0158846 A1 | 7/2008 | Martin |
| 2008/0271737 A1 | 11/2008 | Facer |
| 2008/0271740 A1 | 11/2008 | Gloag |
| 2009/0090364 A1 | 4/2009 | Daugaard |
| 2009/0144923 A1 | 6/2009 | Tuman |
| 2010/0031962 A1 | 2/2010 | Chiu |
| 2010/0154805 A1 | 6/2010 | Duffy |
| 2010/0224199 A1 | 9/2010 | Smith |
| 2011/0014475 A1 | 1/2011 | Murata |
| 2011/0036661 A1 | 2/2011 | Munro |
| 2011/0067700 A1 | 3/2011 | Duffy |
| 2011/0067701 A1* | 3/2011 | Duffy ................. A41D 13/1115 128/206.19 |
| 2011/0147475 A1 | 6/2011 | Biegler |
| 2011/0151171 A1 | 6/2011 | Biegler |
| 2011/0156314 A1 | 6/2011 | Alberg |
| 2012/0012418 A1 | 1/2012 | Nilsson |
| 2012/0123004 A1* | 5/2012 | Stowell ................. C08G 18/48 521/107 |
| 2012/0125341 A1 | 5/2012 | Gebrewold |
| 2013/0074845 A1 | 3/2013 | Smith |
| 2013/0149925 A1 | 6/2013 | Handziak |
| 2013/0247916 A1 | 9/2013 | Symons |
| 2013/0291877 A1 | 11/2013 | Nguyen |
| 2013/0312760 A1 | 11/2013 | Kostyk |

FOREIGN PATENT DOCUMENTS

| | | | | |
|---|---|---|---|---|
| DE | 102010045810 | 3/2012 | | |
| DE | 102008050462 | 9/2013 | | |
| EP | 1495785 | 1/2005 | | |
| EP | 1614361 | 1/2006 | | |
| EP | 2314353 | 10/2010 | | |
| GB | 2163056 | 11/1988 | | |
| GB | 2200281 | 8/1998 | | |
| GB | 2480288 | 11/2011 | | |
| JP | 53-045470 | 4/1978 | | |
| JP | 04332567 | 11/1992 | | |
| JP | 3115302 | 11/2005 | | |
| JP | 3162641 | 9/2010 | | |
| JP | 5240638 | 7/2013 | | |
| JP | 2014-030584 | 2/2014 | | |
| KR | 2007-0071962 | 7/2007 | | |
| KR | 2009-0077454 | 7/2009 | | |
| KR | 10-0973995 | 8/2010 | | |
| KR | 2011-0004564 | 1/2011 | | |
| KR | 10-1074601 | 10/2011 | | |
| KR | 2012-0055440 | 5/2012 | | |
| TH | 69699 | 7/2005 | | |
| TW | 2011-21595 | 7/2011 | | |
| WO | WO 1996-028216 | 9/1996 | | |
| WO | WO 1996-039349 | 12/1996 | | |
| WO | WO 1997-032493 | 9/1997 | | |
| WO | WO 1998-031743 | 7/1998 | | |
| WO | WO 1999-030583 | 6/1999 | | |
| WO | WO 2002-015829 | 2/2002 | | |
| WO | WO 2005-051255 | 6/2005 | | |
| WO | WO 2006-055151 | 5/2006 | | |
| WO | WO 2006-113116 | 10/2006 | | |
| WO | WO 2009-022250 | 2/2009 | | |
| WO | WO 2009-086649 | 7/2009 | | |
| WO | WO 2011-014931 | 2/2011 | | |
| WO | WO 2011-090586 | 7/2011 | | |
| WO | WO 2013-028654 | 2/2013 | | |
| WO | WO 2013-032683 | 3/2013 | | |
| WO | WO 2013-052371 | 4/2013 | | |
| WO | WO-2013052371 A2 * | 4/2013 | ............ | B29C 48/05 |
| WO | WO 2013-165984 | 11/2013 | | |
| WO | WO-2013165984 A1 * | 11/2013 | ........... | A62B 18/025 |
| WO | WO 2013-181009 | 12/2013 | | |
| WO | WO 2014-164242 | 10/2014 | | |
| WO | WO 2015-130934 | 9/2015 | | |

OTHER PUBLICATIONS

Wente, "Superfine Thermoplastic Fibers", Industrial and Engineering. Chemistry, 1956, pp. 1342-1346.

International Search Report for PCT International Application No. PCT/US2015/044748 dated Jan. 5, 2016, 7 pages.

\* cited by examiner

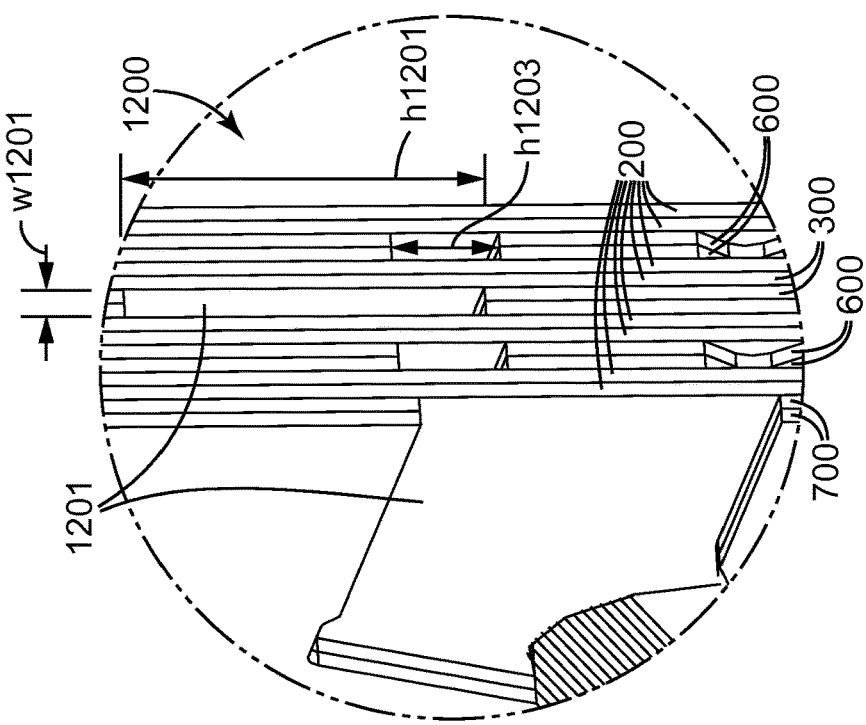
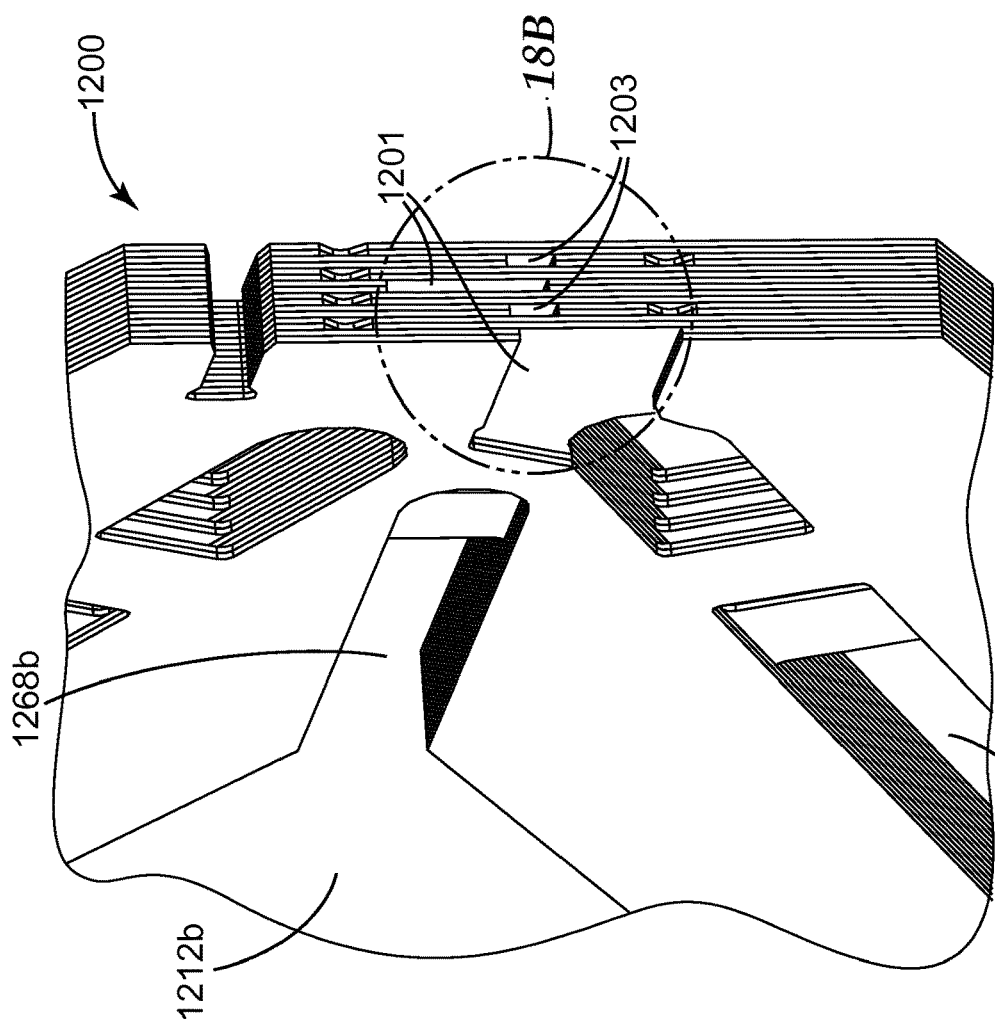
FIG. 18B
FIG. 18A

RESPIRATOR INCLUDING POLYMERIC NETTING AND METHOD OF FORMING SAME

CROSS REFERENCE TO RELATED APPLICATIONS

This application is a national stage filing under 35 U.S.C. 371 of PCT/US2015/044748, filed Aug. 12, 2015, which claims the benefit of Provisional Application No. 62/038,455, filed Aug. 18, 2014, the disclosure of which is incorporated by reference in its/their entirety herein.

BACKGROUND

Respirators are commonly worn over a person's breathing passages for at least one of two common purposes: (1) to prevent impurities or contaminants from entering the wearer's respiratory system; and (2) to protect other persons or things from being exposed to pathogens and other contaminants exhaled by the wearer. In the first situation, the respirator is worn in an environment where the air contains particles that may be harmful to the wearer, for example, in an auto body shop. In the second situation, the respirator is worn in an environment where there is risk of contamination to other persons or things, for example, in an operating room or clean room.

A variety of respirators have been designed to meet either (or both) of these purposes. Some respirators have been categorized as being "filtering face-pieces" because the mask body itself functions as the filtering mechanism. Unlike respirators that use rubber or elastomeric mask bodies with attachable filter cartridges (see, e.g., U.S. Pat. RE39,493 to Yuschak et al.) or insert-molded filter elements (see, e.g., U.S. Pat. No. 4,790,306 to Braun), filtering face-piece respirators are designed to have the filter media cover much of the mask body so that there is no need for installing or replacing a filter cartridge. These filtering face-piece respirators commonly come in one of two configurations: molded respirators and flat-fold respirators.

Molded filtering face-piece respirators often include nonwoven webs of thermally-bonding fibers or open-work plastic meshes to furnish the mask body with its cup-shaped configuration. Molded respirators tend to maintain the same shape during both use and storage. These respirators, therefore, cannot be folded flat for storage and shipping. Examples of patents that disclose molded, filtering, face-piece respirators include U.S. Pat. No. 7,131,442 to Kronzer et al; U.S. Pat. Nos. 6,923,182; 6,041,782 to Angadjivand et al.; U.S. Pat. No. 4,807,619 to Dyrud et al.; and U.S. Pat. No. 4,536,440 to Berg.

Flat-fold respirators, as the name implies, can be folded flat for shipping and storage. Such respirators can be opened into a cup-shaped configuration for use. Examples of flat-fold respirators are described in U.S. Pat. Nos. 6,568,392 and 6,484,722 to Bostock et al.; and U.S. Pat. No. 6,394,090 to Chen. Some flat-fold respirators have been designed with weld lines, seams, and folds to help maintain their cup-shaped configuration during use. Stiffening members also have been incorporated into panels of the mask body. See, e.g., U.S. Patent Publication Nos. 2001/0067700 and 2010/0154805 to Duffy et al.; and U.S. Design Pat. 659,821 to Spoo et al.

Filtering face-piece respirators of the kinds described typically include several different components that are joined or assembled together to make an integral unit. These components may include harnesses, exhalation valves, face seals, headbands, nose clips, and the like. For example, face seal components are regularly added because they provide a comfortable fit between differing contours of a wearer's face and the respirator mask body, and also to accommodate dynamic changes that might render the seal ineffective, such as when a wearer's face is moving while the wearer is speaking.

Further, respirators are regularly provided with a harness that includes one or more straps. These straps are commonly made of an elastomeric material such as a braided headband or a Kraton rubber. See, e.g., U.S. Pat. No. 6,332,465 to Xue; and PCT Patent Publication Nos. WO98/31743 to Deeb et al.; and WO97/32493 A1 to Bryant el al. These straps typically are solid in appearance—that is, you cannot see through the strap, partially or totally. A variety of known respirators and their harnesses are shown in the following patents: U.S. Pat. Nos. RE39,493 to Yuschak et al.; U.S. Pat. No. 4,790,306 to Braun; U.S. Pat. No. 7,131,442 to Kronzer et al.; U.S. Pat. Nos. 6,923,182 and 6,041,782 to Angadjivand et al.; U.S. Pat. No. 4,807,619 to Dyrud et al.; U.S. Pat. No. 4,536,440 to Berg; U.S. Pat. Nos. 6,568,392 and 6,484,722 to Bostock et al.; and U.S. Pat. No. 6,394,090 to Chen. See also U.S. Patent Publication Nos. 2001/0067700 and 2010/0154805 to Duffy et al.; U.S. Design Pat. No. 659,821 to Spoo et al.; and U.S. Pat. No. 3,521,630 to Patrick, Jr. et al.

SUMMARY

In general, the present disclosure provides one or more embodiments of a respirator that includes a polymeric netting. In one or more embodiments, the polymeric netting can be utilized as material for a face seal that is disposed along at least a portion of a perimeter of a mask body of the respirator. Further, in one or more embodiments, the polymeric netting can be utilized as material for a harness that can include one or more straps that are joined to the mask body of the respirator. In one or more embodiments, the polymeric netting can be utilized as a cover web for a respirator. And in one or more embodiments, the polymeric netting can also be utilized in a hearing protector.

In one aspect, the present disclosure provides a respirator that includes a mask body including a perimeter, a harness attached to the mask body, and a face seal disposed adjacent at least a portion of the perimeter of the mask body. The face seal includes a polymeric netting including polymeric ribbons and polymeric strands, each of the polymeric ribbons and strands having a length, width, and height, where the length is the longest dimension, the width is the shortest dimension, and the height is the dimension transverse to the length and the width. The polymeric ribbons have a height-to-width aspect ratio of at least 5 to 1, a major surface that is intermittently bonded to only one polymeric strand, and a height that is at least two times greater than a height of the one polymeric strand.

In another aspect, the present disclosure provides a method of forming a respirator. The method includes forming a respirator body including a perimeter and attaching a harness to the respirator body. The method further includes forming a face seal including a polymeric netting, where the polymeric netting includes polymeric ribbons and polymeric strands, each of the polymeric ribbons and strands having a length, width, and height, where the length is the longest dimension, the width is the shortest dimension, and the height is the dimension transverse to the length and the width. The polymeric ribbons have a height-to-width aspect ratio of at least 5 to 1, a major surface that is intermittently bonded to only one polymeric strand, and a height that is at least two times greater than a height of the one polymeric strand. The method further includes attaching the face seal to the mask body adjacent at least a portion of the perimeter of the mask body.

In another aspect, the present disclosure provides a respirator that includes a mask body and a harness. The harness includes one or more straps that are joined to the mask body on opposing sides of the mask body, where the one or more straps include a polymeric netting. The polymeric netting includes polymeric ribbons and polymeric strands, each of the polymeric ribbons and strands having a length, width, and height, where the length is the longest dimension, the width is the shortest dimension, and the height is the dimension transverse to the length and the width. The polymeric ribbons have a height-to-width aspect ratio of at least 5 to 1, a major surface that is intermittently bonded to only one polymeric strand, and a height that is at least two times greater than a height of the one polymeric strand.

In another aspect, the present disclosure provides a method of forming a respirator. The method includes forming a respirator body including a perimeter, and forming a harness including one or more straps. The one or more straps include a polymeric netting that includes polymeric ribbons and polymeric strands, each of the polymeric ribbons and strands having a length, width, and height, wherein the length is the longest dimension, the width is the shortest dimension, and the height is the dimension transverse to the length and the width. The polymeric ribbons have a height-to-width aspect ratio of at least 5 to 1, a major surface that is intermittently bonded to only one polymeric strand, and a height that is at least two times greater than a height of the one polymeric strand. The method further includes attaching the harness to the respirator body.

In another aspect, the present disclosure provides a hearing protector that includes two ear cups shaped to cover ears of a wearer and a sealing ring secured along a periphery of each ear cup. The sealing ring includes a polymeric netting including polymeric ribbons and polymeric strands, each of the polymeric ribbons and strands having a length, width, and height, where the length is the longest dimension, the width is the shortest dimension, and the height is the dimension transverse to the length and the width. The polymeric ribbons have a height-to-width aspect ratio of at least 5 to 1, a major surface that is intermittently bonded to only one polymeric strand, and a height that is at least two times greater than a height of the one polymeric strand.

All headings provided herein are for the convenience of the reader and should not be used to limit the meaning of any text that follows the heading, unless so specified.

The terms "comprises" and variations thereof do not have a limiting meaning where these terms appear in the description and claims. Such terms will be understood to imply the inclusion of a stated step or element or group of steps or elements but not the exclusion of any other step or element or group of steps or elements. The term "consisting of" means "including," and is limited to whatever follows the phrase "consisting of." Thus, the phrase "consisting of" indicates that the listed elements are required or mandatory and that no other elements may be present. The term "consisting essentially of" means including any elements listed after the phrase, and is limited to other elements that do not interfere with or contribute to the activity or action specified in the disclosure for the listed elements. Thus, the phrase "consisting essentially of" indicates that the listed elements are required or mandatory, but that other elements are optional and may or may not be present depending upon whether or not they materially affect the activity or action of the listed elements.

The words "preferred" and "preferably" refer to embodiments of the disclosure that may afford certain benefits, under certain circumstances; however, other embodiments may also be preferred, under the same or other circumstances. Furthermore, the recitation of one or more preferred embodiments does not imply that other embodiments are not useful, and is not intended to exclude other embodiments from the scope of the disclosure.

In this application, terms such as "a," "an," and "the" are not intended to refer to only a singular entity, but include the general class of which a specific example may be used for illustration. The terms "a," "an," and "the" are used interchangeably with the term "at least one." The phrases "at least one of" and "comprises at least one of" followed by a list refers to any one of the items in the list and any combination of two or more items in the list.

The phrases "at least one of" and "comprises at least one of" followed by a list refers to any one of the items in the list and any combination of two or more items in the list.

As used herein, the term "or" is generally employed in its usual sense including "and/or" unless the content clearly dictates otherwise.

The term "and/or" means one or all of the listed elements or a combination of any two or more of the listed elements.

Also herein, all numbers are assumed to be modified by the term "about" and preferably by the term "exactly." As used herein in connection with a measured quantity, the term "about" refers to that variation in the measured quantity as would be expected by the skilled artisan making the measurement and exercising a level of care commensurate with the objective of the measurement and the precision of the measuring equipment used. Herein, "up to" a number (e.g., up to 50) includes the number (e.g., 50).

Also herein, the recitations of numerical ranges by endpoints include all numbers subsumed within that range as well as the endpoints (e.g., 1 to 5 includes 1, 1.5, 2, 2.75, 3, 3.80, 4, 5, etc.).

Glossary

The terms set forth herein will have the meanings as defined:

"adjacent at least a portion of the perimeter of the mask body" means that an element or device is disposed closer to at least a portion of the perimeter of the mask body than to a central region or portion of the mask body;

"clean air" means a volume of atmospheric ambient air that has been filtered to remove contaminants;

"contaminants" means particles (including dusts, mists, and fumes) and/or other substances that generally may not be considered to be particles (e.g., organic vapors, etc.) but which may be suspended in air;

"crosswise dimension" is the dimension that extends laterally across the respirator, from side-to-side when the respirator is viewed from the front;

"cup-shaped configuration" and variations thereof mean any vessel-type shape that is capable of adequately covering the nose and mouth of a person;

"elastic" in reference to a strap of a harness means being able to be stretched at least 100% and return essentially to the original dimension without imparting damage to the strap;

"exterior gas space" means the ambient atmospheric gas space into which exhaled gas enters after passing through and beyond the mask body and/or exhalation valve;

"exterior surface" means the surface of the mask body exposed to ambient atmospheric gas space when the mask body is positioned on the person's face;

"face seal" means a part(s) located between the mask body and a wearer's face at one or more locations where the mask body would otherwise contact the face;

"filtering face-piece" means that the mask body itself is designed to filter air that passes through it; there are no separately identifiable filter cartridges or insert-molded filter elements attached to or molded into the mask body to achieve this purpose;

"filter" or "filtration layer" means one layers of air-permeable material, which layer(s) is adapted for the primary purpose of removing contaminants (such as particles) from an air stream that passes through it;

"filter media" means an air-permeable structure that is designed to remove contaminants from air that passes through it;

"filtering structure" means a generally air-permeable construction that filters air;

"folded inwardly" means being bent back towards the part from which it extends;

"harness" means a structure or combination of parts that assists in supporting the mask body on a wearer's face;

"interior gas space" means the space between a mask body and a wearer's face;

"interior surface" means the surface of the mask body closest to a wearer's face when the mask body is positioned on the wearer's face;

"joined to" means secured to directly or indirectly;

"line of demarcation" means a fold, seam, weld line, bond line, stitch line, hinge line, and/or any combination thereof;

"mask body" means an air-permeable structure that is designed to fit over the nose and mouth of a wearer and that helps define an interior gas space separated from an exterior gas space (including the seams and bonds that join layers and parts thereof together);

"netting" means an openwork structure where the openings are formed by openings or spaces between ribbons and strands of the netting;

"nose clip" means a mechanical device (other than a nose foam), which device is adapted for use on a mask body to improve the seal at least around a wearer's nose;

"openwork" means having open spaces sized to be large enough for air to easily pass therethrough and for a person to see therethrough with the naked eye (i.e., without the assistance of an instrument);

"perimeter" means the outer edge of the mask body, which outer edge would be disposed generally proximate to a wearer's face when the respirator is being donned by a person; a "perimeter segment" is a portion of the perimeter;

"pleat" means a portion that is designed to be or is folded back upon itself;

"polymeric" and "plastic" each means a material that mainly includes one or more polymers and that may contain other ingredients as well;

"respirator" means an air filtration device that is worn by a person to provide the wearer with clean air to breathe;

"ribbon" refers to longitudinally extending elements in the polymeric netting having a generally rectangular or oblong cross section. There may be ribbons in the polymeric nettings disclosed herein other than those having a height-to-width aspect ratio of at least 3 to 1, at least 5 to 1, or at least 7 to 1. In other words, not all elements in the polymeric netting having rectangular cross sections are required to have a height-to-width aspect ratio of at least 3 to 1, at least 5 to 1, at least 7 to 1, etc. The polymeric strands may also have rectangular cross sections. A major surface of the polymeric ribbons is a surface defined by the height and the length of the ribbon;

"side" means an area on the mask body distanced from a plane that bisects the mask body centrally and vertically when the mask body is oriented in an upright position and viewed from the front;

"sinus region" means the nose region and parts or areas of the mask body that reside beneath the wearer's eyes and/or eye orbitals when the respirator is being worn in a proper configuration;

"snug fit" or "fit snugly" means that an essentially air-tight (or substantially leak-free) fit is provided (between the mask body and the wearer's face);

"strap" means a generally flat elongated structure; and

"transversely extending" means extending generally in the crosswise dimension.

These and other aspects of the present disclosure will be apparent from the detailed description herein. In no event, however, should the above summaries be construed as limitations on the claimed subject matter, which subject matter is defined solely by the attached claims, as may be amended during prosecution.

BRIEF DESCRIPTION OF THE DRAWINGS

Throughout the specification, reference is made to the appended drawings, where like reference numerals designate like elements, and wherein:

FIG. 18A is a perspective assembly drawing of a sequence of shims employing the shims of FIGS. 10-11 and 16-17 configured to form a portion of the polymeric netting as shown in FIG. 6;

FIG. 18B is an expanded view of the section referenced as "18B" in FIG. 18A;

DETAILED DESCRIPTION

Figure 1:
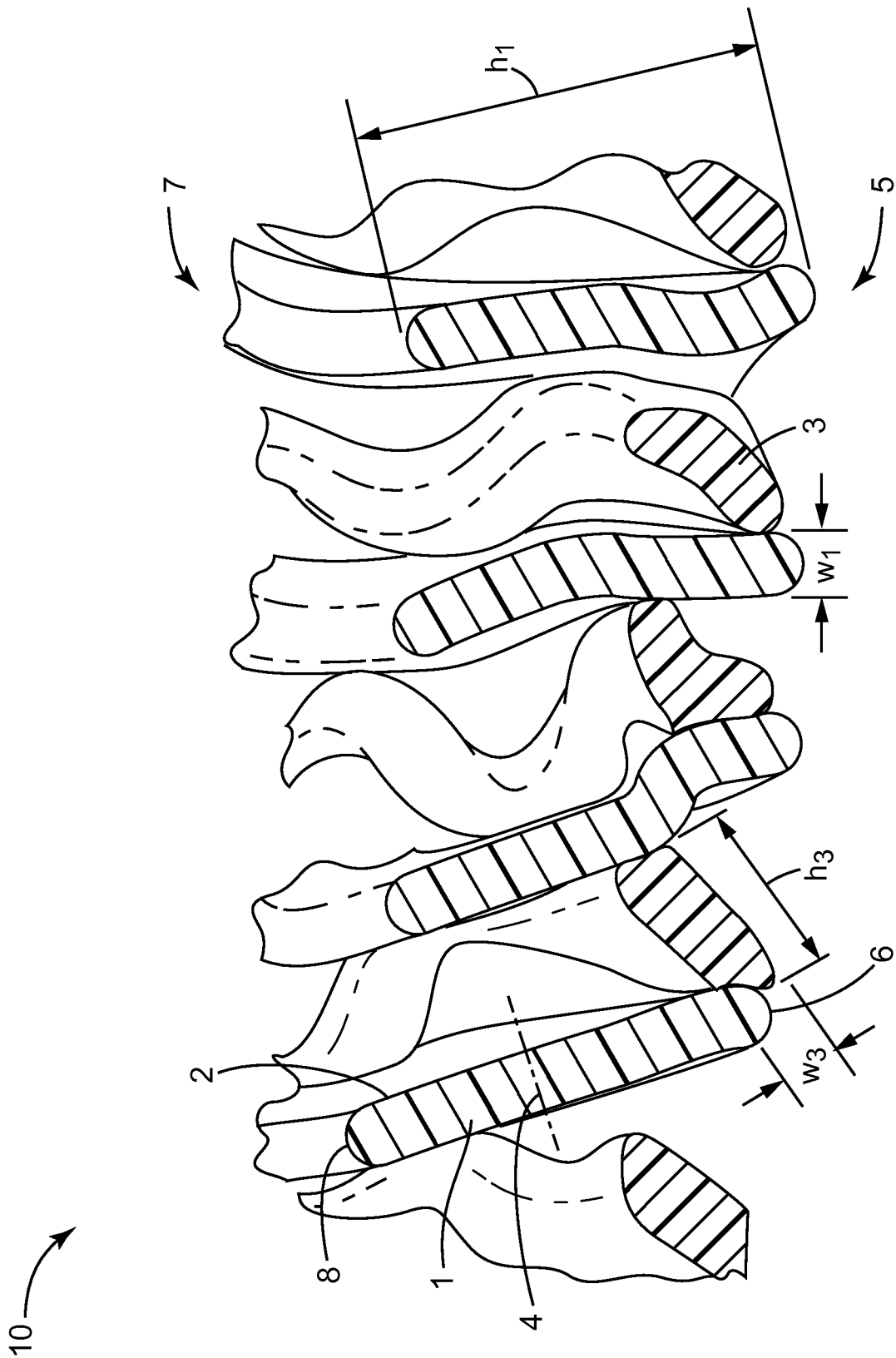
FIG. 1 is cross-sectional side view of an embodiment of a polymeric netting according to the present disclosure.

In general, the present disclosure provides one or more embodiments of a respirator that includes a polymeric netting. In one or more embodiments, the polymeric netting can be used or included as straps for a harness for respirator. Further, in one or more embodiments, the polymeric netting can also be used for a face seal that can be disposed adjacent a perimeter of a mask body of the respirator. And in one or more embodiments, the polymeric netting can also be used as a cover web of the respirator. Further, in one or more embodiments, the polymeric netting can be used in a hearing protector.

Respirators of the present disclosure can include a mask body and a harness attached to the mask body. In one or more embodiments, the harness can include one or more straps that are joined to the mask body on opposing sides of the mask body. Further, the one or more straps can include a polymeric netting as is further described herein. The polymeric netting can allow air to flow through the straps such that the straps are more comfortable for a wearer. Further, in one or more embodiments, the straps can allow moisture or sweat that would otherwise be trapped between the straps and the head of the wearer to be transported away from the head, thereby providing additional comfort to the wearer.

Straps that are commonly used with respirators typically include an elastomeric material such as a braided headband or a Kraton rubber. See, e.g., U.S. Pat. No. 6,332,465 to Xue; WO 9831743 to Deeb et al.; and WO9732493 A1 to Bryant el al. These straps typically are solid in appearance—that is, you cannot see through the strap, partially or totally. The solid nature of the known straps can add to overall product weight and increase heat retention on a wearer's neck. Additionally, conventional respirator straps are constructed such that the strap exhibits one color throughout. Both major strap surfaces therefore have the same appearance. As such it can be difficult to notice if the strap is twisted. The straps also are deprived of any opportunity to be aesthetically colorful or artistically pleasing by exhibiting more than one color.

In one or more embodiments, the polymeric netting that forms or is utilized in one or more straps of the harness can include polymeric ribbons and polymeric strands. Each of the polymeric ribbons and strands has a length, width, and height. The length is the longest dimension, the width is the shortest dimension, and the height is the dimension transverse to the length and the width. Further, in one or more embodiments, the polymeric ribbons can have a height to width aspect ratio of at least 5 to 1. In one or more embodiments, a major surface of each polymeric ribbon can be intermittently bonded to only one polymeric strand. And in one or more embodiments, a height of a polymeric ribbon can be at least 2 times greater than a height of a polymeric strand.

One or more embodiments of respirators described herein can include a face seal that is disposed adjacent at least a portion of a perimeter of a mask body of the respirator. In one or more embodiments, the face seal can include or be constructed from a polymeric netting as is further described herein. Such face seals can allow moisture to be transported away from the face of the wearer, thereby making the masks more comfortable to wear.

Common face seals used in respirators are typically made of a foam material that helps seal the mask body to the face of the wearer. Such foam material, however, may prevent moisture that collects on the face of the wearer from being transported away from the face. This trapped moisture can irritate the skin of the wearer and make the mask feel uncomfortable.

In one or more embodiments, the polymeric netting that forms or is included in the face seal can include polymeric ribbons and polymeric strands. Each of the polymeric ribbons and strands has a length, width, and height. The length is the longest dimension, the width is the shortest dimension, and the height is the dimension transverse to the length and the width. Further, in one or more embodiments, the polymeric ribbons can have a height to width aspect ratio of at least 5 to 1. In one or more embodiments, a major surface of each polymeric ribbon can be intermittently bonded to only one polymeric strand. And in one or more embodiments, a height of a polymeric ribbon can be at least 2 times greater than a height of a polymeric strand.

Further, in one or more embodiments, the respirators described herein can include one or both of an inner cover web and an outer cover web as is further described herein. In one or more embodiments, one or both of the inner cover web and outer cover web can include or be constructed from a polymeric netting as is further described herein.

And in one or more embodiments, the polymeric nettings described herein can be used to form or construct a sealing ring utilized in an ear cup of a hearing protector.

Polymeric Netting

FIG. 1 illustrates a side view of an embodiment of a polymeric netting 10 according to the present disclosure that can be utilized with a respirator as, e.g., straps of a harness, a face seal, etc. The polymeric netting 10 includes polymeric ribbons 1 and polymeric strands 3. The polymeric ribbons 1 and polymeric strands 3 each have a length, width "w1" and "w3," and height "h1" and "h3." The length of the polymeric ribbons 1 and strands 3 is the longest dimension and is not shown in FIG. 1. The length is the longest dimension, the width is the shortest dimension, and the height is the dimension transverse to the length and the width. The height "h1" of the ribbons and the height "h3" strands is typically between the length and width of each, respectively. However, the strands 3 can also have heights "h3" that are substantially the same as their widths "w3". For circular strands, the height and width may both be referred to as diameter. The height-to-width aspect ratio of at least some of the polymeric ribbons is at least three to one. In some embodiments, the height-to-width aspect ratio of at least some of the polymeric ribbons is at least 5:1, 7:1, 8:1, 10:1, 11:1, 15:1, 20:1, 30:1, or 40:1. The height of the polymeric ribbon is generally greater than that of the polymeric strands. In one or more embodiments, the height of each of the polymeric ribbons is at least 2, 2.5, 3, 5, 10, or 20 times greater than the height of the single polymeric strand. In one or more embodiments, the polymeric netting 10 can include any suitable ratio between the height h1 of one or more of the ribbons 1 and the height h3 of one or more of the strands 3. In one or more embodiments, a ratio h1 to h3 can be at least 1:1, 2:1, 3:1, 4:1, 5:1, 6:1, etc. In one or more embodiments, a ratio h1 to h3 can be no greater than 100:1, 50:1, 10:1, etc.

The polymeric ribbons can have any suitable height h1. In one or more embodiments, the height of the polymeric ribbons may be in a range from 0.05 millimeters to 10 millimeters. In one or more embodiments, the height of the polymeric ribbons may be in a range from 0.05 millimeters to 3 millimeters (mm). In one or more embodiments, the height of the polymeric ribbons is greater than 750 micrometers. In one or more embodiments, the height of the polymeric ribbons can be no greater than 1 cm. In one or more embodiments, the height of the polymeric ribbons is in a range from greater than 750 micrometers to 3 mm (e.g., 0.775 mm to 2 mm or 0.8 mm to 1.5 mm). In one or more embodiments, the height of at least one of the polymeric ribbons or polymeric strands is less than 750 micrometers. In one or more embodiments, the height of at least one of the polymeric ribbons or polymeric strands is in a range from 0.1 mm to less than 750 micrometers (e.g., 0.3 mm to 0.745 mm or 0.5 mm to 0.745 mm).

Figure 2:
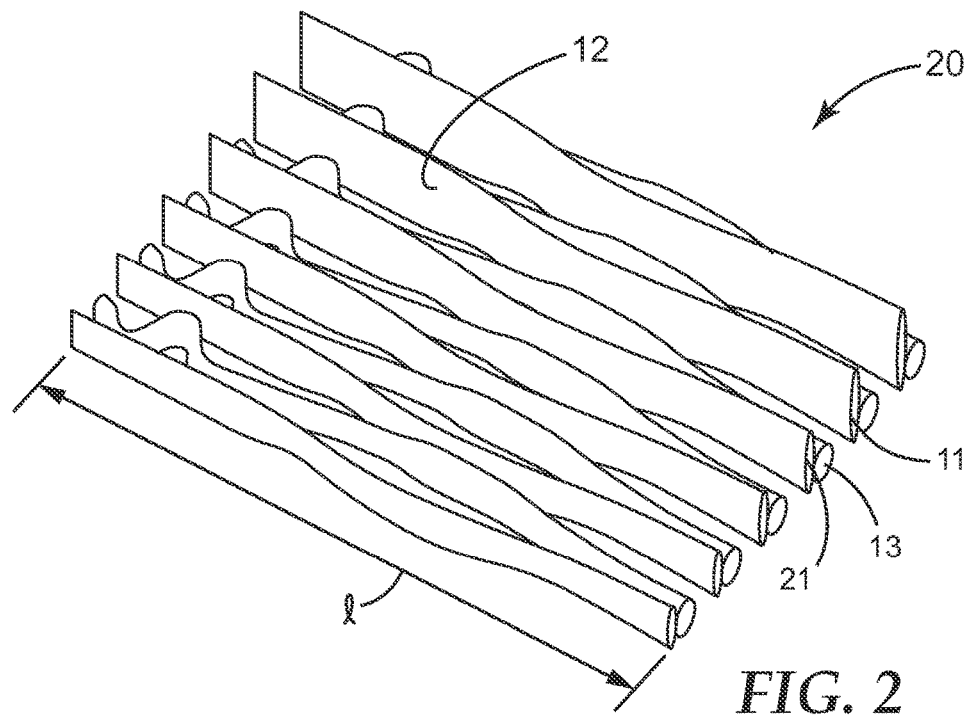
FIG. 2 is a perspective view of an embodiment of a polymeric netting according to the present disclosure.

FIG. 2 illustrates a perspective view of an embodiment of a polymeric netting according to the present disclosure. In this perspective view, the length "1" of the polymeric ribbons and strands can be observed.

Referring again to FIGS. 1-2, the polymeric ribbons 1, 11, 21, each have a first major surface 2, 12 that is intermittently joined to a single polymeric strand 3, 13. That is, two or more polymeric strands are not joined to the first major surface of the polymeric ribbon. When it is said that the first major surface of polymeric ribbon is intermittently joined to the single polymeric strand, it can be observed that the polymeric strand oscillates between bonding to the polymeric ribbon and another portion of the netting on the opposite side of the polymeric strand. In the embodiment illustrated in FIG. 2, two adjacent polymeric ribbons 11, 21 are joined together by a single polymeric strand 13 at least partially alternately bonded to the two adjacent polymeric ribbons 11, 21. However, this is not a requirement. For example, in one or more embodiments, the polymeric strand can oscillate between bonding to the polymeric ribbon and a non-oscillating strand that does not necessarily have a height-to-width aspect ratio of at least three to one. Since a major surface of the polymeric ribbon is intermittently bonded to a polymeric strand, which is at least partially alternately bonded to the polymeric ribbon and another strand or ribbon of the netting, the polymeric ribbons are typically not intersected by the polymeric strands. In any of the embodiments of the polymeric netting disclosed herein, the strands and ribbons of polymer typically do not substantially intersect each other (e.g., at least 50 (at least 55, 60, 65, 70, 75, 80, 85, 90, 95, 99, or even 100) percent by number do not intersect each other) either by forming a superimposed intersection point or an interlaid intersection point.

Figure 3:
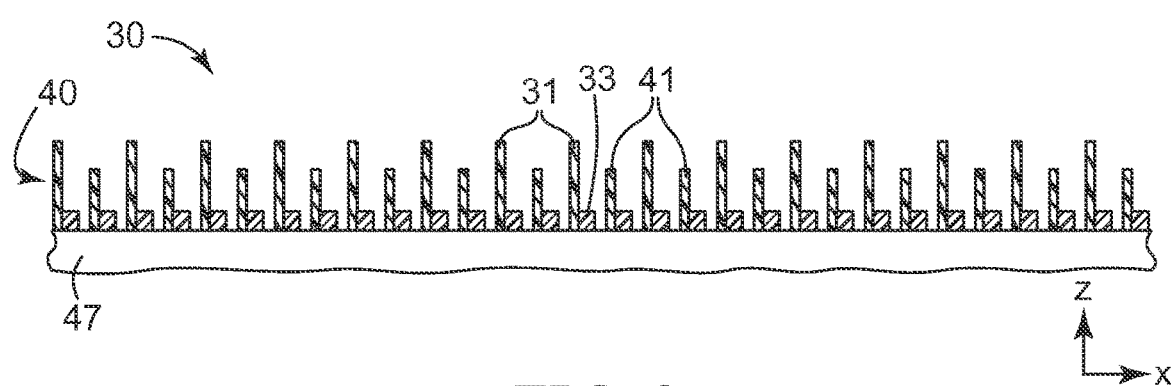
FIG. 3 is a schematic cross-sectional view of a plane of another embodiment of a polymeric netting according to the present disclosure, in which the polymeric netting is joined to a substrate such as an absorbent component.
Figure 4:
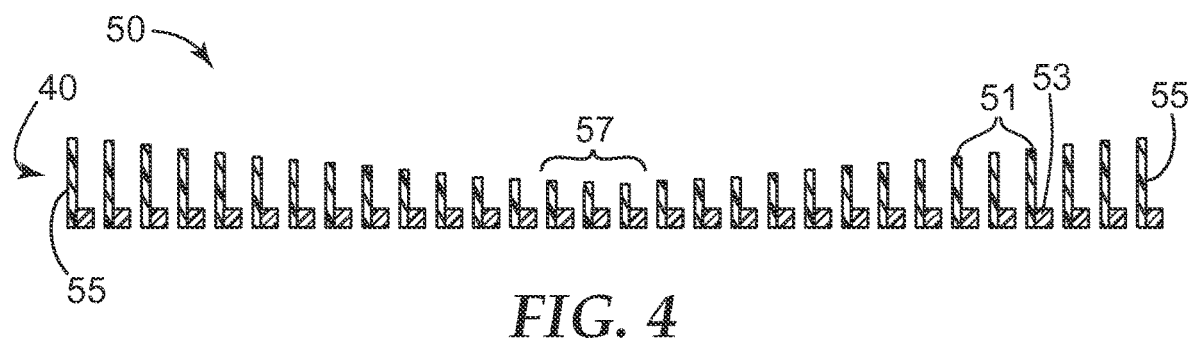
FIG. 4 is a schematic cross-sectional view of a plane of yet another embodiment of a polymeric netting according to the present disclosure.

In FIG. 1, the heights h1 of the polymeric ribbons 1 are all about the same size, and the heights h3 of the polymeric strands 3 are all the same size, but as shown in FIGS. 2-4, this is not a requirement. For example, there may be two different types of polymeric ribbons 31, 41 as shown in FIG. 3. The height-to-width aspect ratio of polymeric ribbon 31 is greater than the height-to-width aspect ratio of polymeric ribbon 41. In FIGS. 2 and 4, the polymeric ribbons 11, 21, 51 have a range of heights. In FIG. 4, the height-to-width aspect ratio of polymeric ribbons 51 is greater on edges 55 of polymeric netting 50 than in a center 57 of the netting. In these embodiments, at least some of the polymeric ribbons 51 have a height-to-width aspect ratio of at least 3 to 1.

While in FIGS. 1-4 the spacings between the various polymeric ribbons and polymeric strands in the polymeric netting are approximately equal, this is not a requirement. The spacing between any two adjacent polymeric ribbons 1, 11, 21, 31, 41, 51 or any two adjacent polymeric strands 3, 13, 33, 53 can vary in the cross-web direction. For example, any two adjacent polymeric ribbons or any two adjacent polymeric strands may be positioned more closely together at the center of the netting than on the edges or vice versa.

In the embodiments illustrated in FIGS. 1-4, the polymeric ribbons and polymeric strands alternate. In some embodiments of the polymeric netting according to the present disclosure and/or made according to the techniques disclosed herein, the polymeric ribbons and polymeric strands alternate in at least a portion of the netting. In these embodiments and even in other embodiments in which the polymeric ribbons and polymeric strands do not alternate, typically each major surface of the polymeric ribbon is intermittently bonded to only one polymeric strand. Furthermore, it should be noted that the spacing shown in the cross-sectional view of a plane of the polymeric netting shown in FIGS. 3-6 and 8 (described herein) is idealized. In a typically cross-sectional planar view, not all of the polymeric strands would appear to be identically bonded to the major surfaces of the polymeric ribbons. Instead, the positions of the strands may appear to be more like that shown in the cross-sectional planar view of FIG. 7 and in the side view shown in FIG. 1.

As described herein, one or more polymeric strands of the polymeric netting can oscillate between ribbons. In such embodiments, the oscillating polymeric strand can form one or more spaces, openings, or apertures through the netting. For example, polymeric netting 30 of FIG. 3 includes one or more oscillating strands 33 that form one or more openings 34 in the polymeric netting. These openings in the netting 30 can allow air or other fluids to be transported through the netting. In one or more embodiments, the polymeric netting 30 can be permeable to air such that the polymeric netting would be considered to be breathable. Alternatively, in one or more embodiments, the polymeric strands 33 can be nonoscillating. In one or more embodiments that include one or more nonoscillating strands, the polymeric netting may not include one or more openings or apertures. In such embodiments, the polymeric netting 30 may impermeable to air or other fluids. In embodiments where the polymeric netting is impermeable, the polymeric netting would not be considered to be breathable.

In one or more embodiments, the polymeric nettings of the present disclosure can be formed on a substrate or backing layer. For example, netting 30 of FIG. 3 is disposed on substrate 47, which can include any suitable material or combination of materials. In one or more embodiments, the substrate 47 can be an absorbent material. The substrates utilized with the polymeric nettings described herein can be permeable or impermeable. In one or more embodiments, the substrate 47 can block or obstruct air or fluids that would have passed through the netting 30 through one or more apertures or openings 34 formed by the oscillating strands such that the combination of the netting and substrate is impermeable to air or other fluids.

Figure 5:
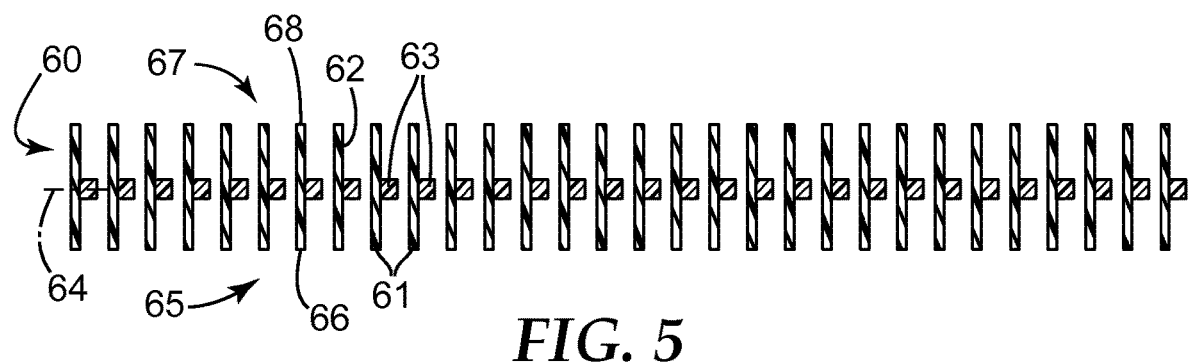
FIG. 5 is a schematic cross-sectional view of a plane of still another embodiment of a polymeric netting according to the present disclosure.
Figure 6:
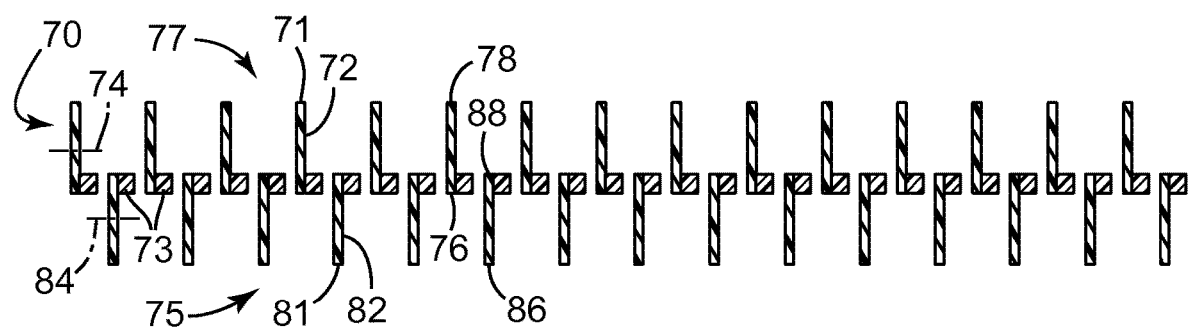
FIG. 6 is a schematic cross-sectional view of a plane of still another embodiment of a polymeric netting according to the present disclosure.

Some embodiments of configurations of the polymeric netting according to the present disclosure are illustrated in FIGS. 1 and 5-6. In FIG. 1, the polymeric ribbons 1 each have a center line 4 bisecting major surface 2 and first and second edges 6, 8 symmetrically disposed on opposite sides of the center line 4. For each of the polymeric ribbons 1, the associated single polymeric strand 3 is bonded to the major surface 2 at a location between the center line 4 and the first edges 6. In the illustrated embodiment, the single polymeric strand 3 is bonded to the two adjacent polymeric ribbons 1 at a location between the center line 4 and the first edges 6. In other words, the single polymeric strand 3 is bonded to major surface 2 closer to the first edge 6 than the second edge 8. Explained yet another way, the polymeric netting 10 has first and second opposing major surfaces 5, 7 transverse to the major surfaces 2 of the polymeric ribbons 1. The second major surface 7 of the polymeric netting 10 includes the second edges 8 of the polymeric ribbons 1, and the first major surface 5 of the polymeric netting 10 includes the first edges 6 of the polymeric ribbons 1 and portions of at least some of the polymeric strands 3.

In the embodiment shown in FIG. 5, polymeric ribbons 61 and polymeric strands 63 are vertically aligned. In these embodiments, a single polymeric strand 63 is bonded to major surface 62 of ribbon 61 at a location including center line 64. Explained yet another way, the polymeric netting 60 has first and second opposing major surfaces 65, 67 transverse to the major surfaces 62 of the polymeric ribbons 61. The first major surface 65 of the polymeric netting 60 includes the first edges 66 of the polymeric ribbons 61, and the second major surface 67 of the polymeric netting 60 includes the second edges 68 of the polymeric ribbons 61. Neither the first nor second major surfaces 65, 67 include a portion of the polymeric strands 63.

In the embodiment illustrated in FIG. 6, the polymeric ribbons 71, 81 each have a center line 74, 84 bisecting major surface 72, 82, and first, top 78, 88 and second, bottom edges 76, 86 symmetrically disposed on opposite sides of the center line 74, 84, where some polymeric ribbons 81 are bonded to their single polymeric strands 73 at a location between the center line 84 and the first, top edge 88 and some of the polymeric ribbons 71 are bonded to their single polymeric strand 73 at a location between the center line 74 at the second, bottom edge 76. In other words, the single polymeric strands 73 are bonded to a major surface 72 of a first portion of polymeric ribbons 71 closer to the first edge 76 than the second edge 78, and the single polymeric strands 73 are bonded to major surface 82 of a second portion of polymeric ribbons 81 closer to the second edge 88 than the first edge 86. Explained another way, the polymeric netting 70 has first and second opposing major surfaces 75, 77 transverse to the major surfaces 72, 82 of the polymeric ribbons 71, 81. The first major surface 75 of the polymeric netting 70 includes the first edges 86 of a first group of the polymeric ribbons 81, and the second major surface 77 of the polymeric netting 70 includes the second edges 78 of a second group of the polymeric ribbons 71. Neither the first nor second major surfaces 75, 77 include a portion of the polymeric strands 73. The first group of the polymeric ribbons 81 does not extend to the second major surface 77, and the second group of the polymeric ribbons 71 does not extend to the first major surface 75. Further details about this embodiment can be found, e.g., in co-pending U.S. Patent Application Ser. No. 64/946,592 to Legatt et al. entitled POLYMERIC NETTING OF STRANDS AND FIRST AND SECOND RIBBONS AND METHODS OF MAKING THE SAME.

While in FIGS. 1-6 the widths w1 of the polymeric ribbons are each about the same, and the widths w3 of the polymeric strands are each about the same, this is also not a requirement. The widths of the polymeric ribbons and/or polymeric strands may change across the netting (e.g., in a direction transverse to the length of the polymeric ribbons and polymeric strands). For example, at least one of the polymeric ribbons or polymeric strands may have a larger width w1 or w3 at the center of the netting than on the edges or vice versa.

Figure 7:
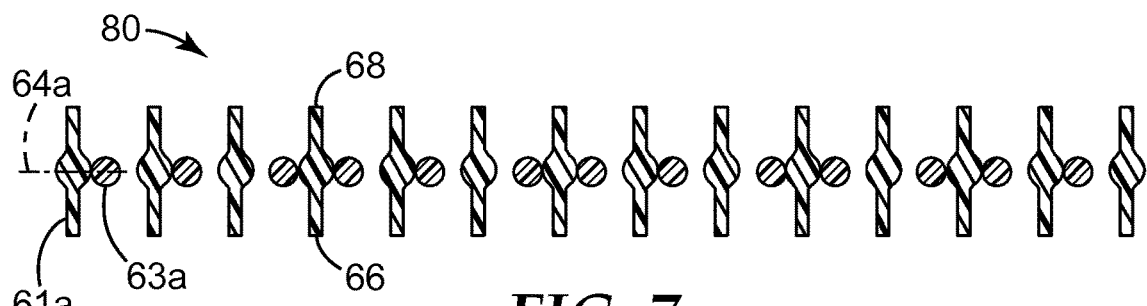
FIG. 7 is a schematic cross-sectional view of a plane of still another embodiment of a polymeric netting according to the present disclosure.

In the embodiments illustrated in FIGS. 1-6, the width w1 of the polymeric ribbons is uniform from the top edge 8, 78, 88 to the bottom edge 6, 76, 86. Again, this is not a requirement. For example, a polymeric netting 80 having ribbons with non-uniform widths between the top and bottom edges is shown in FIG. 7. This embodiment is like the embodiment shown in FIG. 5 in which polymeric ribbons 61a and polymeric strands 63a are vertically centered. In polymeric netting 80, however, the width of the polymeric ribbon 61a is wider at a location including a center line 64a than it is at top and bottom edges 68 and 66. That is, in the illustrated embodiment, the polymeric ribbon 61a is wider at the location where it is bonded to the polymeric strand 63a.

In the polymeric netting 80 illustrated in FIG. 7, the polymeric ribbon 61a is designed to have a greater width near the center line 64a than at the top and bottom edges 68 and 66. The width of the polymeric ribbon can also be designed to change from the top edge to the bottom edge in other ways. For example, the width can be greater at the top edge 68 and/or bottom edge 66 than near the center line 64a. The polymeric strands may be bonded to the polymeric ribbons at these locations. The polymeric ribbons may also have random fluctuations in width caused by the extrusion process. In any situation in which the width of the polymeric ribbon is non-uniform, the width w1 of the polymeric ribbon for the purposes of determining the height-to-width aspect ratio is measured at its smallest width.

Similarly, the height of the polymeric ribbon may be measured at its tallest height. The heights of the polymeric ribbons are generally uniform. The polymeric ribbons in any of the embodiments of polymeric nettings disclosed herein typically would not have any discrete posts (e.g., mechanical fasteners or hooks) upstanding from the edges of the polymeric ribbons. Similarly, the polymeric nettings disclosed herein in any of their embodiments typically would not have any discrete posts (e.g., mechanical fasteners or hooks) on their first or second major surfaces.

Figure 8:
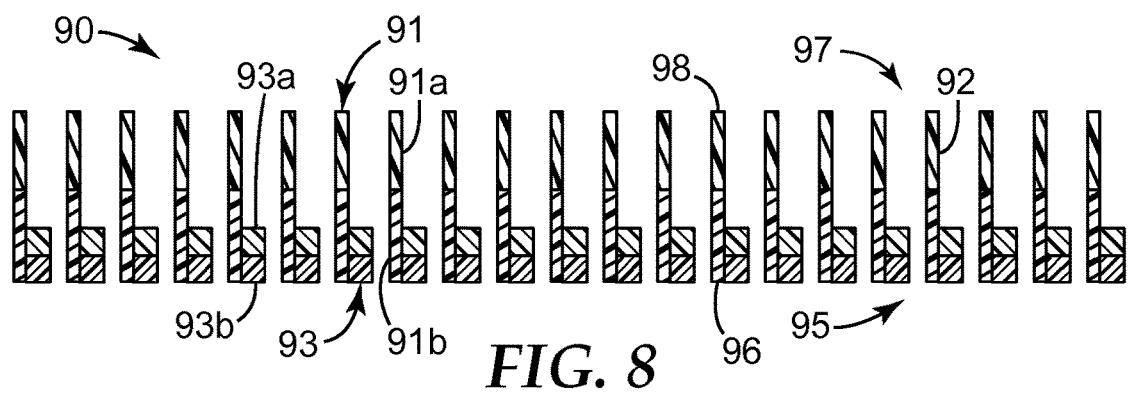
FIG. 8 is a schematic cross-sectional view of a plane of yet another embodiment of a polymeric netting according to the present disclosure.

In some embodiments in which the polymeric ribbons each have a center line bisecting the major surface and first and second edges symmetrically disposed on opposite sides of the center line, the first edges of the polymeric ribbons include a different composition than the second edges of the polymeric ribbons. An embodiment of such a polymeric netting is shown in FIG. 8. In FIG. 8, polymeric netting 90 includes polymeric ribbons 91 and polymeric strands 93. The polymeric ribbons 91 each have a first portion 91a and a second portion 91b. The first and second portions 91a and 91b are made from different polymeric compositions. Likewise, the polymeric strands 93 each have a first portion 93a and a second portion 93b. In these embodiments, the polymeric netting 90 has first and second opposing major surfaces 95, 97 transverse to the major surfaces 92 of the polymeric ribbons 91. The first major surface 95 of the polymeric netting 90 includes the first edges 96 of polymeric ribbons 91 and second portions 93b of polymeric strands 93, and the second major surface 97 of the polymeric netting 90 includes the second edges 98 of polymeric ribbons 91. The first portions 91a of the polymeric ribbons 91 and consequently the second edges 98 include a first polymeric composition, and the second portions 91b of the polymeric ribbons 91 and consequently the first edges 96 include a second polymeric composition. The first portions 93a of the polymeric strands include a third polymeric composition, and the second portions 93b of the polymeric strands 93 include a fourth polymeric composition. In the illustrated embodiment, at least the first and second polymeric compositions are different, and the first polymeric composition does not extend to the first edges 96 of the polymeric ribbons 91.

Although other techniques may be useful, the various embodiments of polymeric nettings disclosed herein can be prepared by an extrusion die and/or method according to the present disclosure. The extrusion die according to the present disclosure has a variety of passageways from cavities within the die to dispensing orifices. The dispensing orifices each have a width, which is the dimension that corresponds to the width of a particular polymeric ribbon or polymeric strand, and a height, which is the dimension that corresponds to the thickness of the resulting extruded polymeric netting and the height of a particular polymeric ribbon or polymeric strand.

In one or more embodiments of the extrusion die and method of making a polymeric netting according to the present disclosure, the extrusion die has at least one cavity, a dispensing surface, and fluid passageways between the at least one cavity and the dispensing surface. The dispensing surface has an array of first dispensing orifices separated by an array of second dispensing orifices. This means that for any two first dispensing orifices, there is at least one second dispensing orifice between them. However, it is possible that for any two first dispensing orifices, there is more than one second dispensing orifice between them, and there may be dispensing orifices other than the second dispensing orifices between them in a side-by-side configuration.

The fluid passageways are capable of physically separating the polymers from the at least one cavity (e.g., first and second cavities and optionally any further die cavities within the extrusion die) until the fluid passageways enter the dispensing orifices. The shape of the different passageways within the die may be identical or different. Examples of passageway cross-sectional shapes include round, square, and rectangular shapes. These cross-sectional shapes, selection of polymeric materials, and die swell can influence the cross-sectional shape of the ribbons and strands.

In one or more embodiments, including the embodiments illustrated in FIGS. 9 through 27A and 27B, the extrusion die includes at least a first and second cavity, with first fluid passageways between the first cavity and the first dispensing orifices and second fluid passageways between the second cavity and the second dispensing orifices. The first and second dispensing orifices each have a height and a width, the first dispensing orifices each have a height-to-width aspect ratio of at least 3:1 (in some embodiments, at least 5:1, 8:1, 10:1, 11:1, 15:1, 20:1, 30:1, or 40:1), and the height of the first dispensing orifices is larger (in some embodiments, at least 2, 2.5, 3, 5, 10, or 20 times larger) than the height of the second dispensing orifices. In some embodiments, particularly embodiments of the extrusion die, the first dispensing orifices, second dispensing orifices, and any other dispensing orifices are arranged one-by-one across the dispensing surface. That is, in these embodiments, in the width dimension of the die, the dispensing orifices are arranged singly or one-by-one regardless of the alignment of the dispensing orifices in these embodiments. For example, the dispensing orifices are not stacked in a group of two, three, or more in the height direction.

In one or more embodiments of the method according to the present disclosure, polymeric ribbons are dispensed from the first dispensing orifices at a first speed while simultaneously polymeric strands are dispensed from the second dispensing orifices at a second speed, and the second speed is at least 2 times the first speed. In some embodiments, the second speed is in a range from 2 to 6 or from 2 to 4 times the first speed. In one or more embodiments in which the extrusion die includes at least first and second cavities, the first cavity of the extrusion die is supplied with a first polymeric composition at a first pressure so as to dispense the polymeric ribbons from the array of first dispensing orifices at a first speed, the second cavity of the extrusion die is supplied with a second polymeric composition at a second pressure so as to dispense the polymeric strands from the array of second dispensing orifices at a second speed, where the second speed is at least 2 (in some embodiments, 2 to 6, or 2 to 4) times the first speed.

In one or more embodiments of the method according to the present disclosure, polymeric ribbons are dispensed from the first dispensing orifices at a first speed while simultaneously polymeric strands are dispensed from the second dispensing orifices at a second speed, and the first speed is at least 2 times the second speed. In one or more embodiments, the first speed is in a range from 2 to 6 or from 2 to 4 times the second speed. In one or more embodiments in which the extrusion die includes at least first and second cavities, the first cavity of the extrusion die is supplied with a first polymeric composition at a first pressure so as to dispense the polymeric ribbons from the array of first dispensing orifices at a first speed, the second cavity of the extrusion die is supplied with a second polymeric composition at a second pressure so as to dispense the polymeric strands from the array of second dispensing orifices at a second speed, wherein the first speed is at least 2 (in some embodiments, 2 to 6, or 2 to 4) times the second speed.

While either the polymeric ribbons or polymeric strands may be made to oscillate, typically larger bond areas are observed when the polymeric strands are oscillating. Therefore, in the methods described herein, the polymeric strand is described as the oscillating strand.

The size of the polymeric ribbons and polymeric strands can be adjusted, for example, by the composition of the extruded polymers, velocity of the extruded strands, and/or the orifice design (e.g., cross sectional area (e.g., height and/or width of the orifices)). As taught in PCT Patent Publication No. WO 2013/028654 (Ausen et al.), a dispensing surface with a first polymer orifice three times greater in area than the second polymer orifice may not generate a net with polymeric ribbons with a height greater than the polymeric stands depending on the identity of the polymeric compositions and the pressure within the cavities. In one or more embodiments of the extrusion die and method according to the present disclosure, the height-to-width aspect ratio of the orifices is at least 5:1.

Conveniently, the extrusion die according to and/or useful for practicing the present disclosure may include a plurality of shims. The plurality of shims together define the at least one cavity, the dispensing surface, and the fluid passageways between the at least one cavity and the dispensing surface. In one or more embodiments, the plurality of shims includes a plurality of sequences of shims where each sequence includes at least one first shim that provides a first fluid passageway between the at least one cavity and at least one of the first dispensing orifices, and at least one second shim that provides a second fluid passageway between the at least one cavity and at least one of the second dispensing orifices. In some embodiments, the shims together define a first cavity and a second cavity, the extrusion die having a plurality of first dispensing orifices in fluid communication with the first cavity and having a plurality of second dispensing orifices in fluid communication with the second cavity.

In one or more embodiments, the shims will be assembled according to a plan that provides a sequence of shims of diverse types. Since different applications may have different requirements, the sequences can have diverse numbers of shims. The sequence may be a repeating sequence that is not limited to a particular number of repeats in a particular zone. Or the sequence may not regularly repeat, but different sequences of shims may be used.

Figure 9:
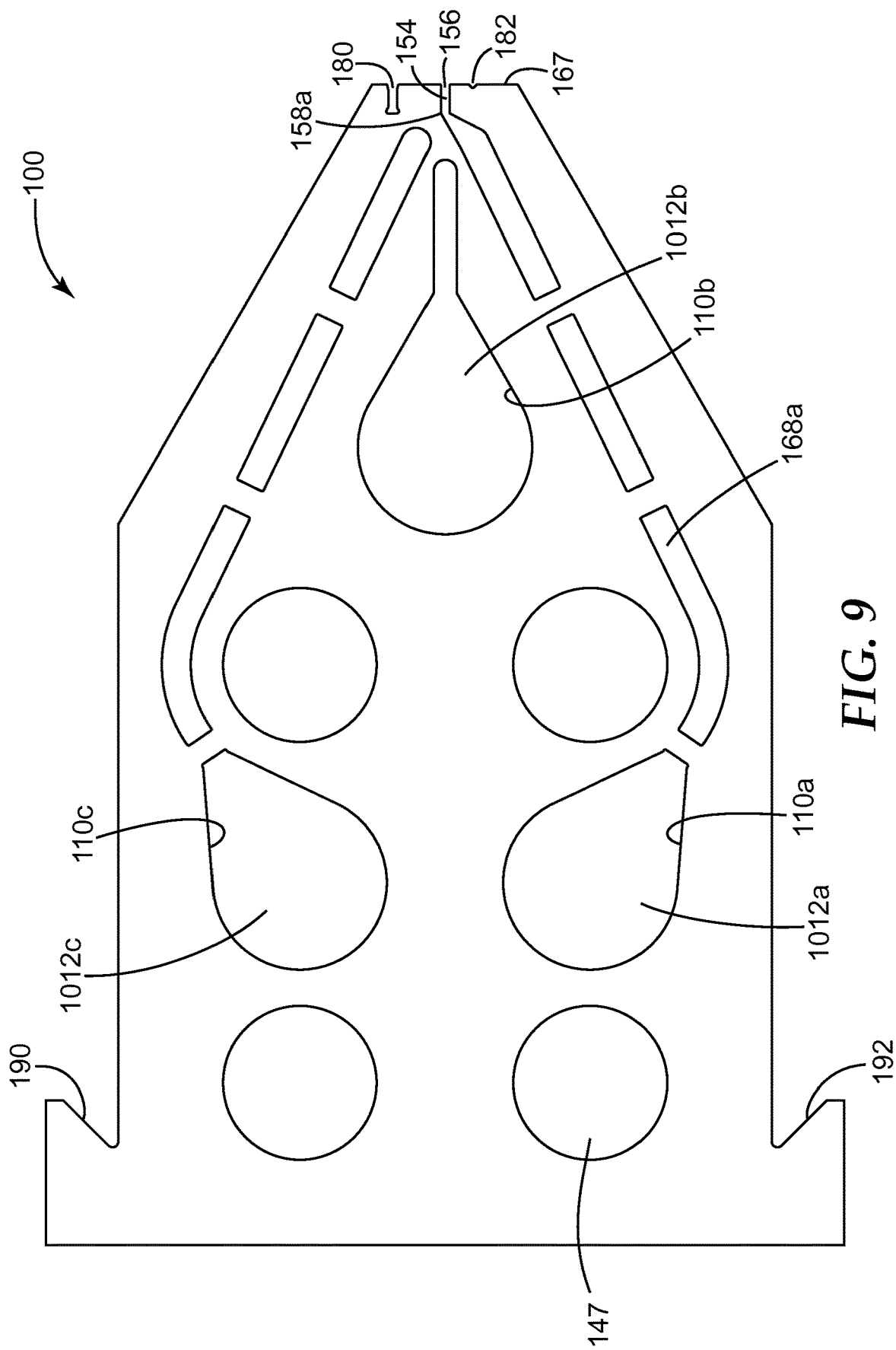
FIG. 9 is a plan view of an embodiment of a shim suitable for a sequence of shims capable of forming a polymeric netting as shown, e.g., in FIGS. 1-4.
Figure 10:
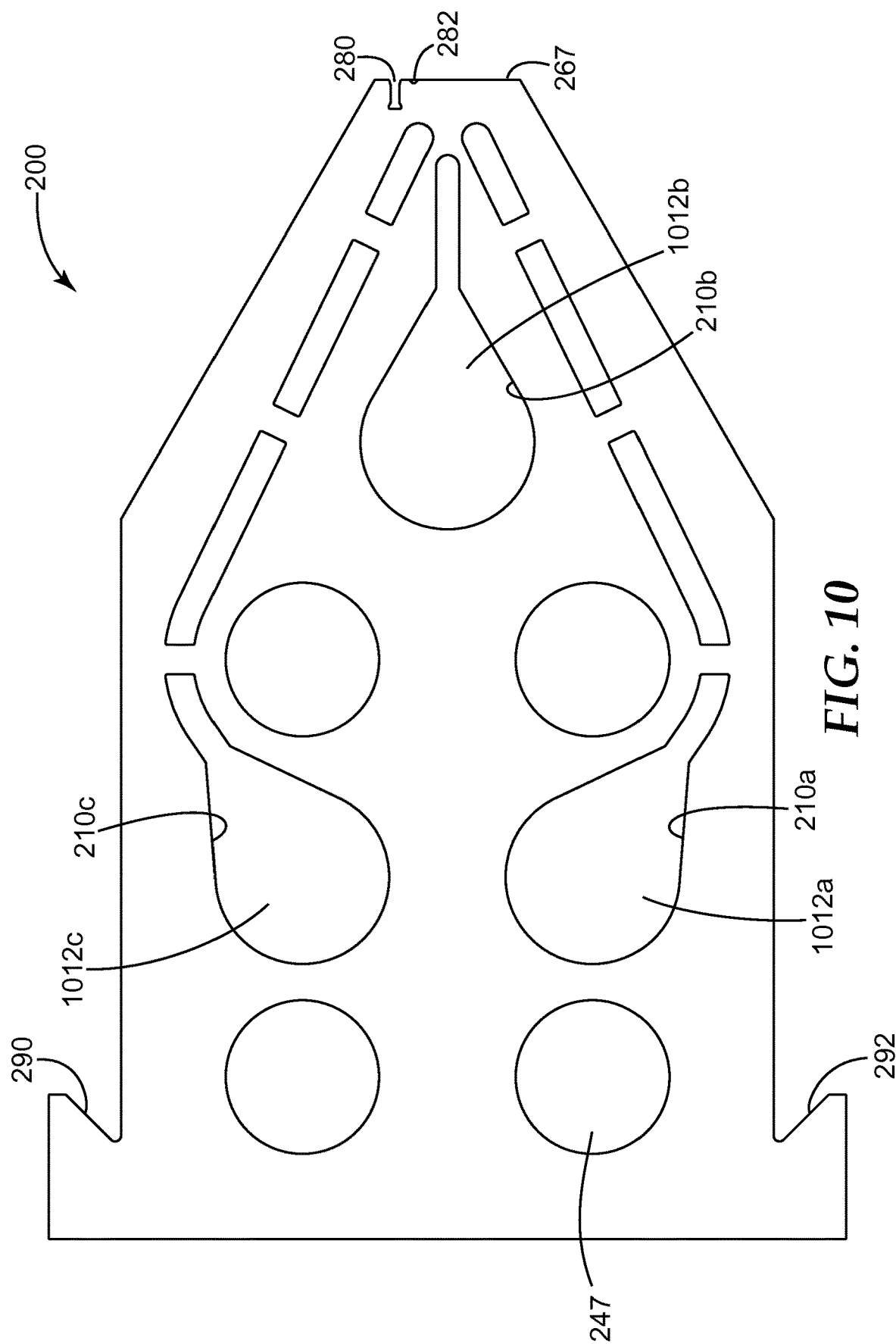
FIG. 10 is a plan view of another embodiment of a shim suitable for a sequence of shims capable of forming a polymeric netting as shown, e.g., in FIGS. 1-7.
Figure 11:
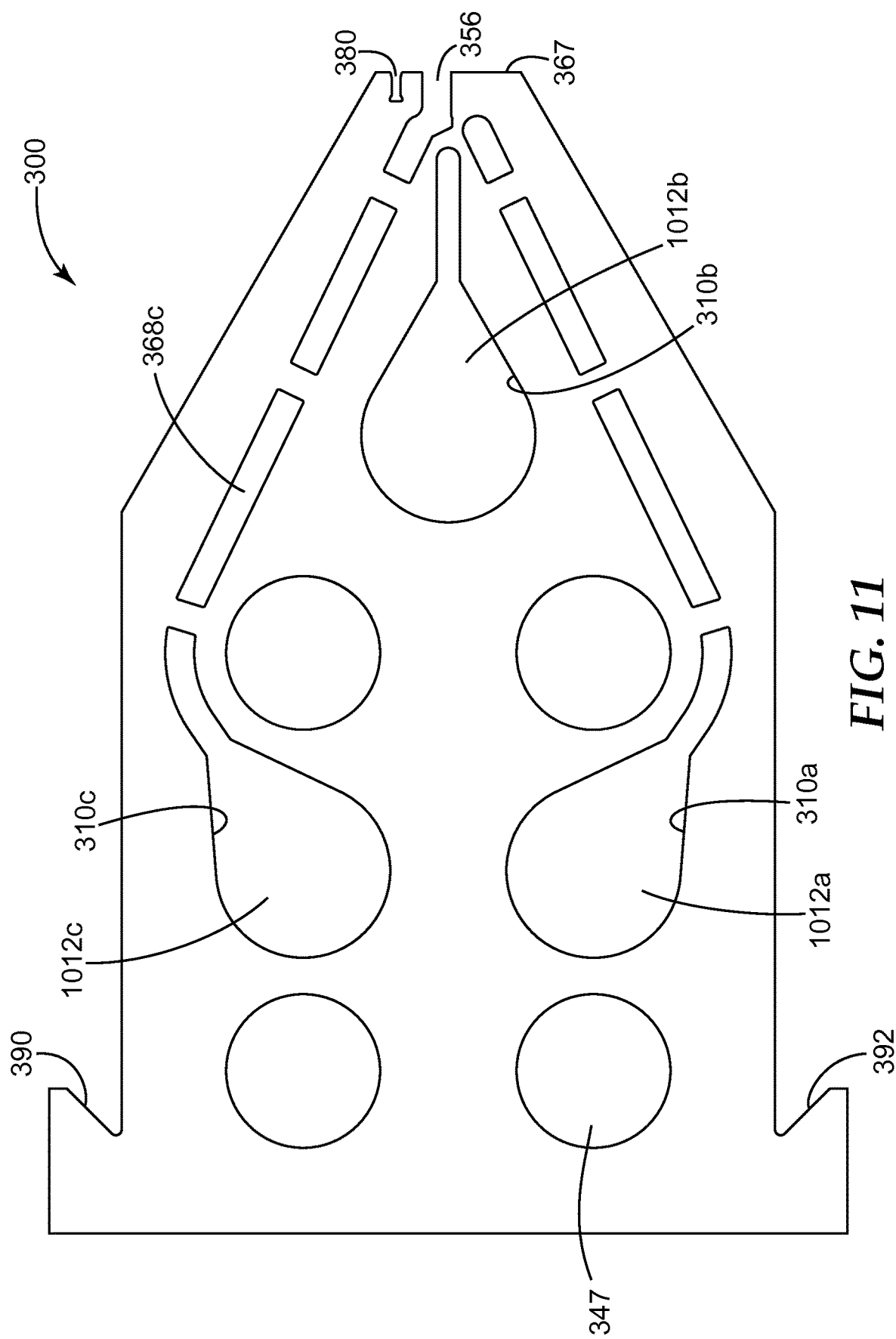
FIG. 11 is a plan view of another embodiment of a shim suitable for a sequence of shims capable of forming a polymeric netting as shown, e.g., in FIGS. 1-4.

A plurality of shims that is useful for providing a polymeric netting according to the present disclosure is shown in FIGS. 9-11, 12A, and 12B. Referring now to FIG. 9, a plan view of shim 100 is illustrated. Shim 100 is useful in a sequence of shims 1000 shown in FIGS. 12A and 12B. Other shims useful in this sequence are shown in FIGS. 10-11. Shim 100 has first aperture 110$a$, second aperture 110$b$, and third aperture 110$c$. When shim sequence 1000 is assembled, first apertures 110$a$, 210$a$, and 310$a$ in shims 100, 200, and 300 together define at least a portion of first cavity 1012$a$. Similarly, second apertures 110$b$, 210$b$, and 310$b$ in shims 100, 200, and 300 together define at least a portion of second cavity 1012$b$, and third apertures 110$c$, 210$c$, and 310$c$ in shims 100, 200, and 300 together define at least a portion of third cavity 1012$c$. Shim 100 has several holes 147 to allow the passage of, e.g., bolts to hold shim 100 and others to be described herein into an assembly. Shim 100 has dispensing surface 167, and in this particular embodiment, dispensing surface 167 has indexing groove 180, which is useful for conveniently aligning the shims with an appropriately shaped key during assembly of the shims into a die, and identification notch 182 to help verify that the die has been assembled in the desired manner Shim 100 has shoulders 190 and 192, which can be conveniently engaged by compression blocks 2204 described herein in connection with FIGS. 22-23. Shim 100 has dispensing opening 156 but no integral connection between dispensing opening 156 and any of apertures 110$a$, 110$b$, or 110$c$. There is no connection, for example, from cavity 110$a$ to dispensing opening 156, via, for example, passageway 168$a$, but the flow has a route 1068$a$ to the dispensing surface when shim 100 is assembled with shims 200 and 300 as illustrated in assembly drawing 1000 (see FIG. 12A). The dimensions of duct 154, and especially dispensing opening 156 at its end, can be designed to provide the dimensions desired in the polymer strands extruded from them. The dimensions of dispensing opening 156 and the dimensions of passageway 158$a$ also influence the desired strand speed.

Referring now to FIG. 10, a plan view of shim 200 is illustrated. Shim 200 has first aperture 210$a$, second aperture 210$b$, and third aperture 210$c$. When shim 200 is assembled with others as shown in FIG. 12A, aperture 210a helps define first cavity 1012a, aperture 210b helps define second cavity 1012b, and aperture 210c helps define third cavity 1012c. Shim 200 has several holes 247 to allow the passage of, e.g., bolts to hold shim 200 and others to be described herein into an assembly. Shim 200 has dispensing surface 267, and in this particular embodiment, dispensing surface 267 has indexing groove 280 and identification notch 282. Shim 200 also has shoulders 290 and 292. There is no passage from any of the cavities to dispensing surface 267 since this shim creates a non-dispensing area along the width of the die. In use shim(s) 200 separates shims 100 producing polymeric strands 3 from shims 300 producing polymeric ribbons 1.

Referring now to FIG. 11, a plan view of shim 300 is illustrated. Shim 300 has first aperture 310a, second aperture 310b, and third aperture 310c. When shim 300 is assembled with others as shown in FIG. 12A, aperture 310a helps define first cavity 1012a, aperture 310b helps define second cavity 1012b, and aperture 310c helps define third cavity 1012c. Shim 300 has several holes 347 to allow the passage of, e.g., bolts to hold shim 300 and others to be described herein into an assembly. Shim 300 has dispensing surface 367, and in this particular embodiment, dispensing surface 367 has indexing groove 380. Shim 300 also has shoulders 390 and 392. Shim 300 has dispensing opening 356 but no integral connection between dispensing opening 356 and any of and any of apertures 310a, 310b, or 310c. There is no connection, e.g., from aperture 310c to dispensing opening 356, via, for example, passageway 368c, but the flow has a route 1068c to the dispensing surface when shim 300 is assembled with shims 100 and 200 as illustrated in sequence 1000 (see FIG. 12A). Comparing FIG. 11 with FIG. 9, one observes that dispensing opening 356 is bigger than dispensing opening 156. In some embodiments, dispensing opening 356 is at least twice the size of dispensing opening 156. In some embodiments, dispensing opening 356 is at least 2.5, 3, 5, 10, or 20 times bigger than dispensing opening 156.

Figure 12B:
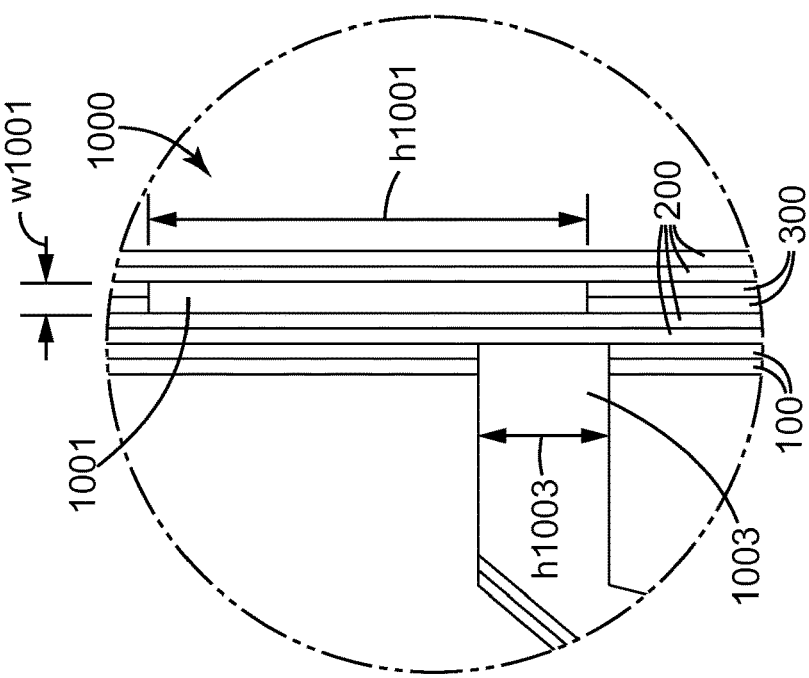
FIG. 12B is an expanded view of the section referenced as "12B" in FIG. 12A.
Figure 12A:
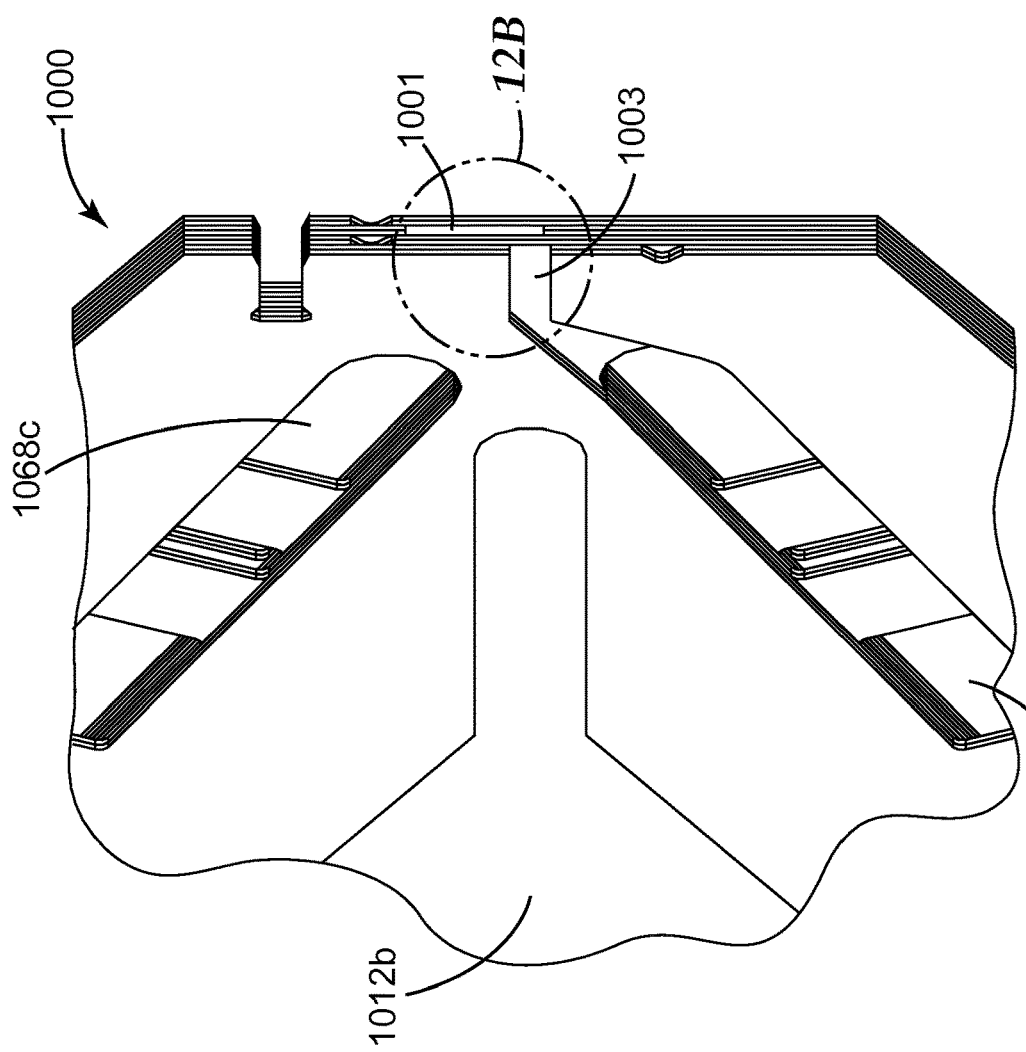
FIG. 12A is a perspective assembly drawing of a sequence of shims employing the shims of FIGS. 9-11 configured to form a portion of the polymeric netting as shown in FIG. 1.

FIGS. 12A and 12B illustrate a perspective assembly drawing of a sequence of shims, collectively 1000, employing the shims of FIGS. 9 to 11 so as to produce a polymeric netting 10 as shown in FIG. 1. Proceeding left to right, sequence 1000 includes two shims 100 that can extrude polymeric strands (e.g., polymeric strands 3 of netting 10 of FIG. 1), two shims 200, two shims 300 that can extrude polymeric ribbons (e.g., polymeric ribbons 1 of netting 10 of FIG. 1), and two shims 200. The first dispensing orifices 1001 each have an aspect ratio defined by height h1001 and width w1001. The height-to-width aspect ratio is at least three to one (in some embodiments, at least 5:1, 8:1, 10:1, 11:1, 15:1, 20:1, 30:1, or 40:1). First dispensing orifices 1001 and second dispensing orifices 1003 are separated by two instances of shims 200. The separation causes the separation of polymeric ribbons 1 from polymeric strands 3 in the polymeric netting 10. The height h1001 of the first dispensing orifices is greater than the height h1003 of the second dispensing orifices. In some embodiments, the height of the first dispensing orifices h1001 is at least 2, 2.5, 3, 5, 10, or 20 times larger than the height of the second dispensing orifices h1003.

Modifications of the sequence 1000 shown in FIGS. 12A and 12B can be used in combination with sequence 1000, for example, to make the polymeric nettings 20, 30, and 50, as shown in FIGS. 2-4. To make polymeric netting 30 shown in FIG. 3, sequence 1000 can be alternated with another sequence similar to 1000 in which shim 300 has a somewhat smaller opening 356, for example. While shim 300 can be useful for extruding polymeric ribbons 31, a shim with a somewhat smaller opening 356 can be useful for extruding polymeric ribbons 41. In some embodiments, sequence 1000 can be alternated with another sequence similar to 1000 in which shim 300 is replaced by shim 100, and the flow rate of the polymer coming from cavity 1012c can be adjusted so that this strand does not oscillate. This sequence can make a polymeric netting in which a polymeric strand 33 oscillates between bonding to the polymeric ribbon 31 and bonding to a non-oscillating strand that does not necessarily have a height-to-width aspect ratio of at least three to one. To make polymeric netting 20 shown in FIG. 2, sequence 1000 can be combined with similar sequences in which shim 300 is modified to have progressively smaller openings 356, for example, to provide a plurality of shim sequences. While shim 300 can be useful for extruding polymeric ribbons 11, a shim with a somewhat smaller opening 356 can be useful for extruding polymeric ribbons 21. Such a plurality of shim sequences can be repeated in the opposite order to provide a polymeric netting 50 as shown in FIG. 4.

In a method using the extrusion die shown in FIGS. 12A and 12B to make a polymeric netting as shown in FIG. 1, for example, polymer from first cavity 1012a emerges as polymeric strands 3 from second dispensing orifices 1003, and polymer from third cavity 1012c emerges as polymeric ribbons 1 from first dispensing orifices 1001. The dimensions of the fluid passageways and the pressures in cavities 1012a and 1012c are typically selected so that the speed of oscillating polymeric strands 3 is between about 2 and 6 (in some embodiments, 2 and 4) times greater than the speed of polymeric ribbons 1. To make a polymeric netting as shown in FIG. 1, second cavity 1012b is unused, but this cavity could be used to introduce another polymeric composition in polymeric netting 10.

Figure 14:
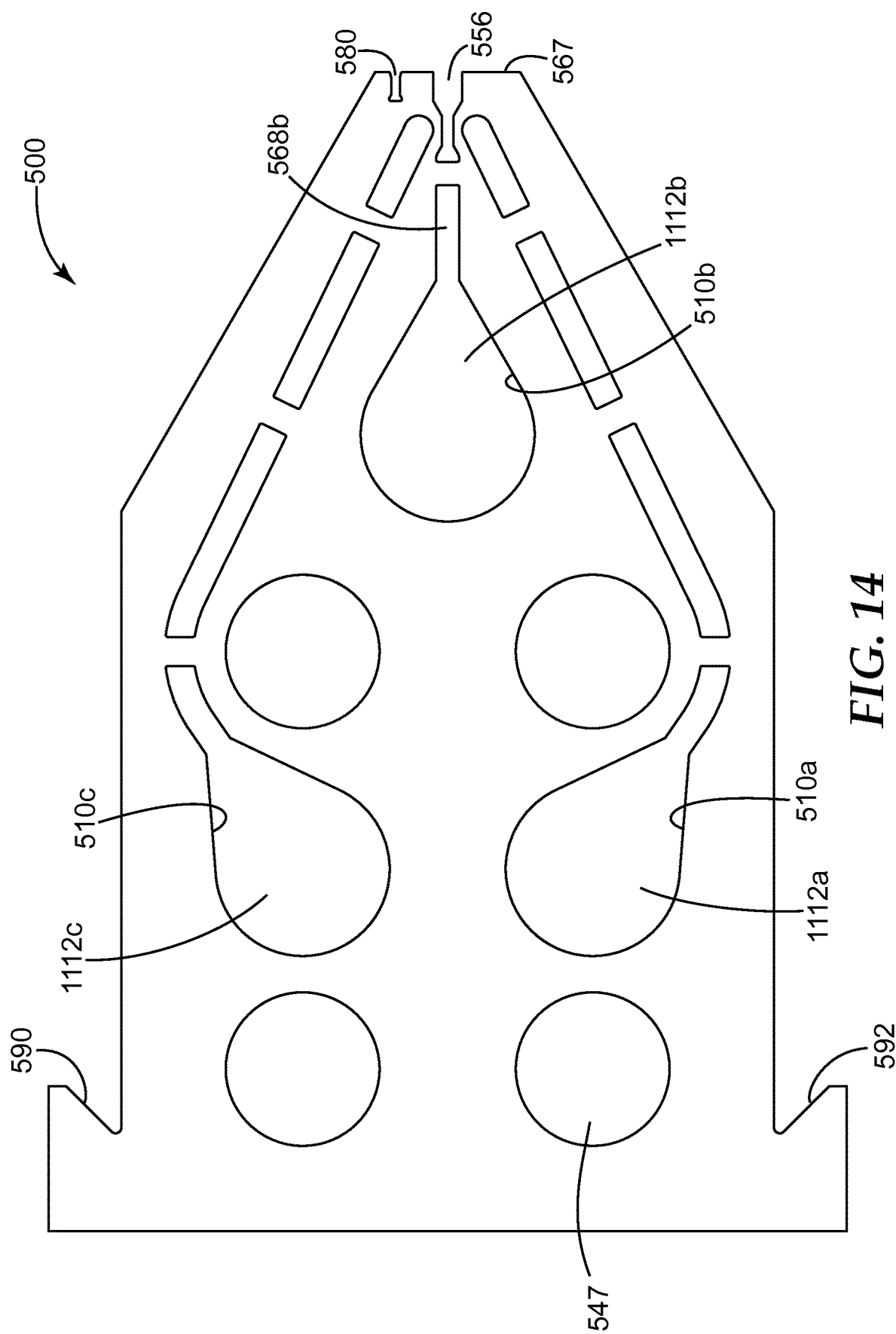
FIG. 14 is a plan view of another embodiment of a shim suitable for a sequence of shims capable of forming a polymeric netting as shown, e.g., in FIG. 5.
Figure 15B:
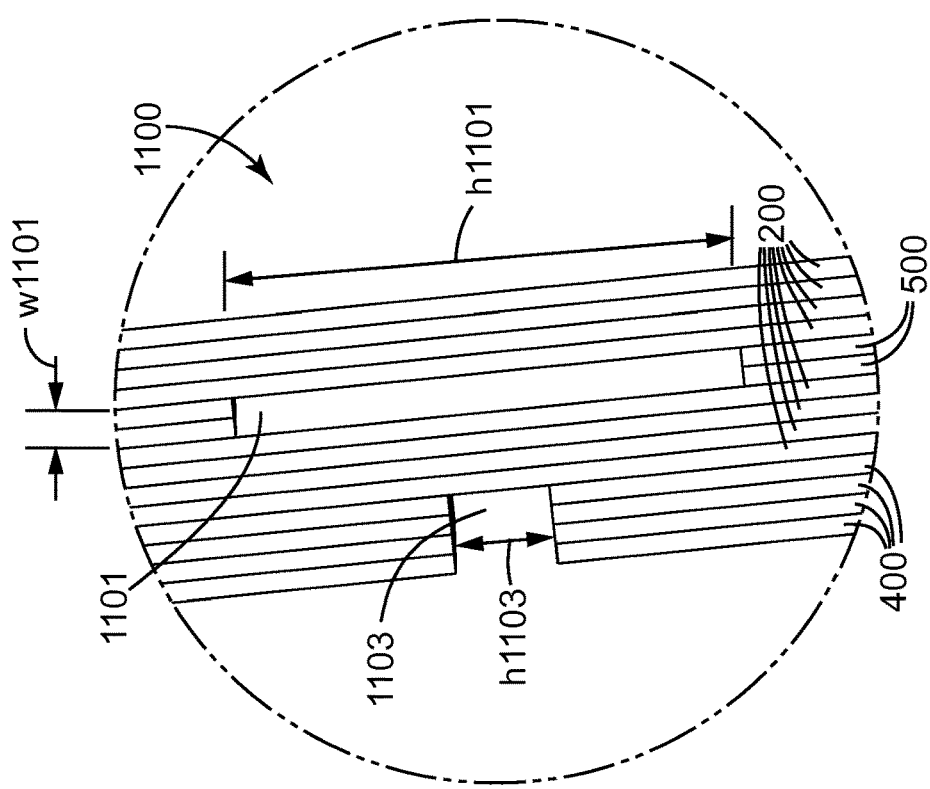
FIG. 15B is an expanded view of the section referenced as "15B" in FIG. 15A.
Figure 15A:
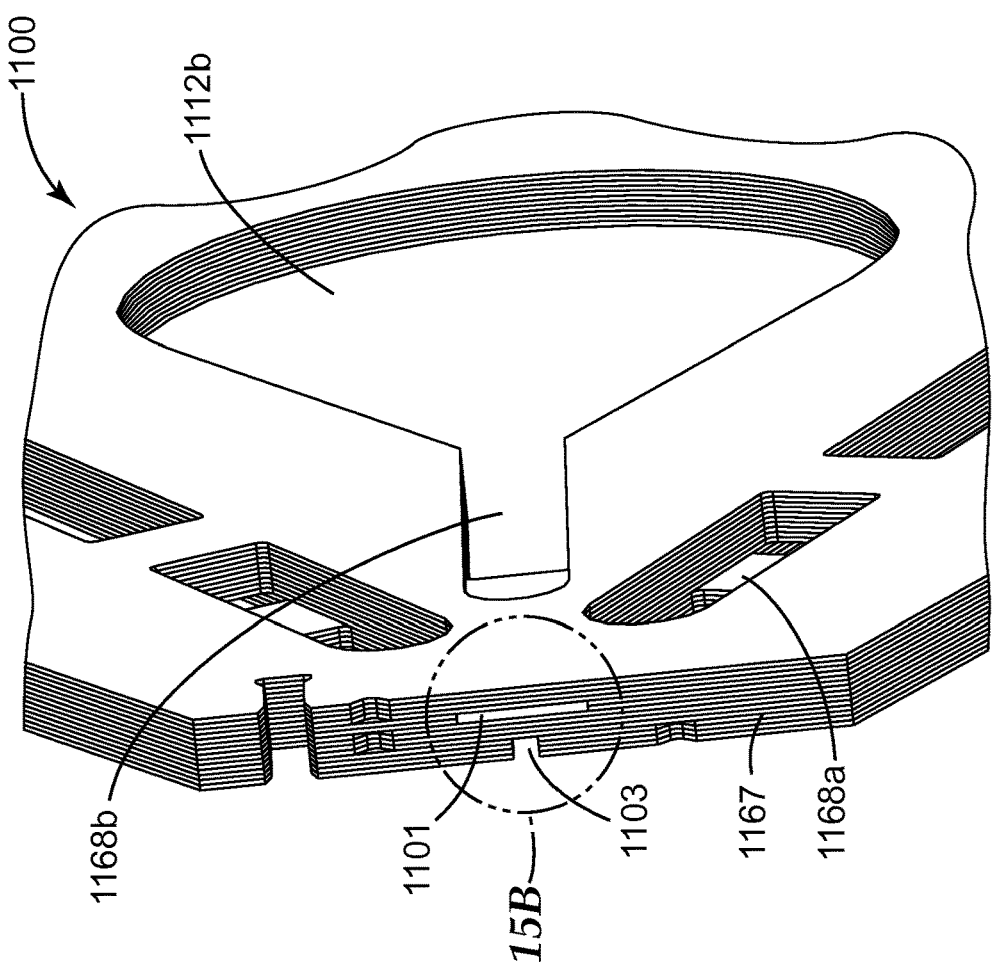
FIG. 15A is a perspective assembly drawing of a sequence of shims employing the shims of FIGS. 10 and 13-14 configured to form a portion of the polymeric netting as shown in FIG. 5.

A polymeric netting such as that indicated by polymeric netting 60 in FIG. 5 can be made, for example, using a shim sequence shown in FIGS. 15A and 15B. FIGS. 15A and 15B show a perspective assembly of a sequence of shims including shims 200 as described herein in connection with FIG. 10 and shims 400 and 500, described herein in connection with FIGS. 13 and 14, respectively.

Figure 13:
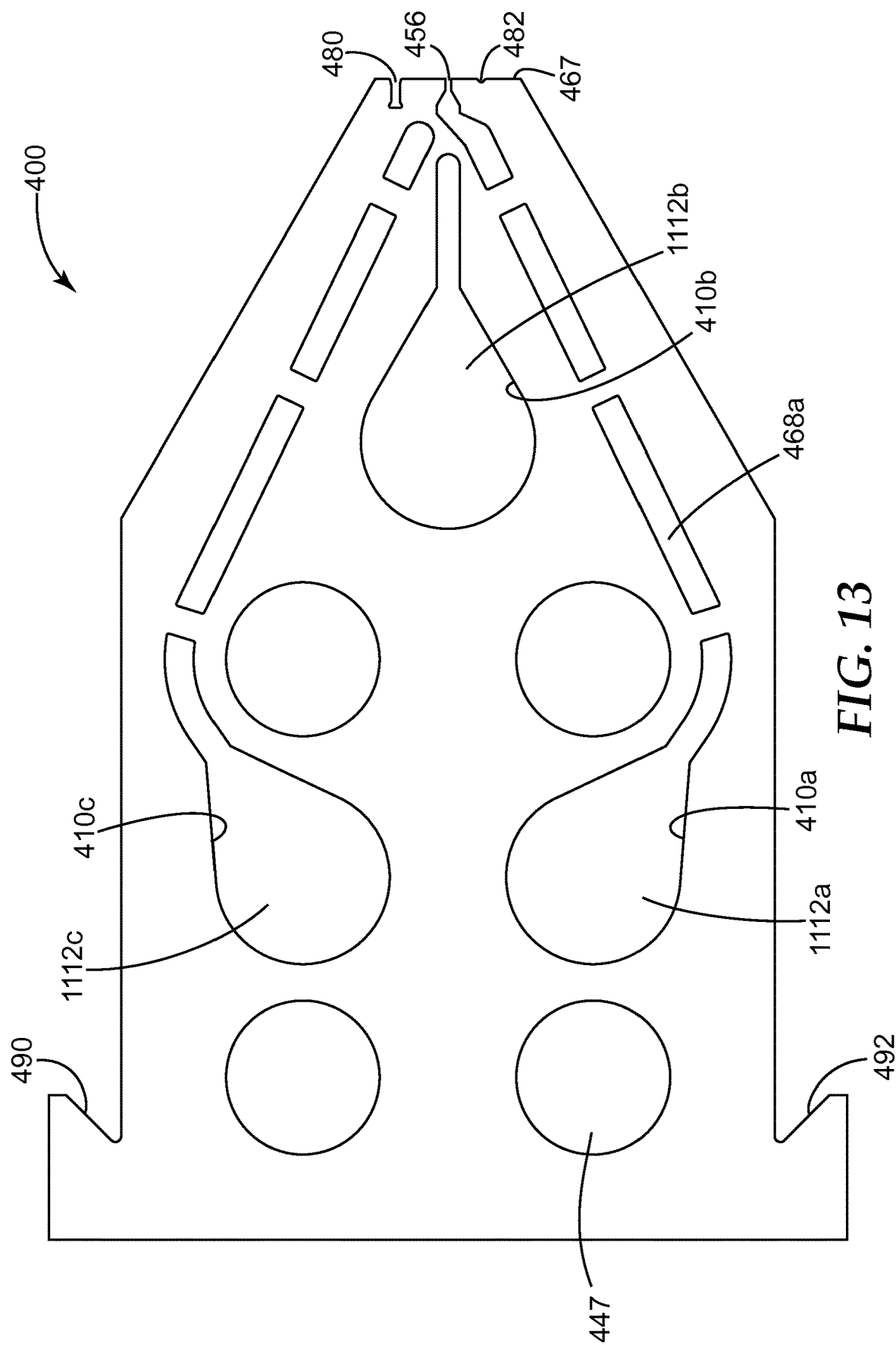
FIG. 13 is a plan view of an embodiment of a shim suitable for a sequence of shims capable of forming a polymeric netting as shown, e.g., in FIG. 5.

Referring now to FIG. 13, a plan view of shim 400 is illustrated. Shim 400 has first aperture 410a, second aperture 410b, and third aperture 410c. When shim 400 is assembled with others as shown in FIG. 15, aperture 410a helps define first cavity 1112a, aperture 410b helps define second cavity 1112b, and aperture 410c helps define third cavity 1112c. Shim 400 has several holes 447 to allow the passage of, e.g., bolts to hold shim 400 and others to be described herein into an assembly. Shim 400 has dispensing surface 467, and in this particular embodiment, dispensing surface 467 has indexing groove 480 and identification notch 482. Shim 400 also has shoulders 490 and 492. Shim 400 has dispensing opening 456 but no integral connection between dispensing opening 456 and any of apertures 410a, 410b, or 410c. There is no connection, for example, from aperture 410c to dispensing opening 456, via, for example, passageway 468a, but the flow has a route 1168a to the dispensing surface in the perpendicular-to-the-plane-of-the-drawing dimension when shim 400 is assembled with shims 200 and 500 as illustrated in sequence 1100 (see FIG. 15A). The dimensions of 456 can be designed to provide the dimensions desired in the polymer strands extruded therefrom. The dimensions of dispensing opening 456 and the dimensions of passageway leading to it also influence the strand speed.

Referring now to FIG. 14, a plan view of shim 500 is illustrated. Shim 500 has first aperture 510a, second aperture 510b, and third aperture 510c. When shim 500 is assembled with others as shown in FIGS. 15A and 15B, aperture 510a helps define first cavity 1112a, aperture 510b helps define second cavity 1112b, and aperture 510c helps define third cavity 1112c. Shim 500 has several holes 547 to allow the passage of, for example, bolts to hold shim 500 and others to be described herein into an assembly. Shim 500 has dispensing surface 567, and in this particular embodiment, dispensing surface 567 has indexing groove 580. Shim 500 also has shoulders 590 and 592. Shim 500 has dispensing opening 556 but has no integral connection between dispensing opening 556 and any of apertures 510a, 510b, or 510c. There is no connection, e.g., from aperture 510b to dispensing opening 556, via, e.g., passageway 568b, but the flow has a route 1168b to the dispensing surface when shim 500 is assembled with shims 200 and 400 as illustrated in assembly drawing, e.g., FIG. 15A.

FIGS. 15A and 15B illustrate a perspective assembly drawing of a sequence of shims, collectively 1100, employing the shims of FIGS. 10 and 13-14 so as to produce a polymeric netting 60 as shown in FIG. 5. Proceeding left to right, sequence 1100 includes four shims 400 that can extrude polymeric strands 63, four shims 200, two shims 500 that can extrude polymeric ribbons 61, and four shims 200. Dispensing orifices 1101 and 1103 are separated by four instances of shims 200. The separation causes the separation of polymeric ribbons 61 from polymeric strands 63 in the polymeric netting 60. The sequence of shims 1100 is similar to that of 1000 except that the dispensing orifices 1101 and 1103 are vertically aligned so that the second dispensing orifices are located in the cross-sectional middle of the dispensing surface 1167. As in the embodiment shown in FIG. 12B, the first dispensing orifices 1101 each have an aspect ratio defined by height h1101 and width w1101 of at least three to one (in some embodiments, at least 5:1, 8:1, 10:1, 11:1, 15:1, 20:1, 30:1, or 40:1), and the height h1101 of the first dispensing orifices is at least 2, 2.5, 3, 5, 10, or 20 times larger than the height h1103 of the second dispensing orifices.

In a method using the extrusion die shown in FIGS. 15A and 15B to make a polymeric netting as shown in FIG. 5, e.g., polymer from first cavity 1112a emerges as polymeric strands 63 from second dispensing orifices 1103, and polymer from second cavity 1112b emerges as polymeric ribbons 61 from first dispensing orifices 1101. The dimensions of the fluid passageways and the pressures in cavities 1112a and 1112b are typically selected so that the speed of oscillating polymeric strands 63 is between about 2 and 6 (in some embodiments, 2 and 4) times greater than the speed of polymeric ribbons 61. To make a polymeric netting as shown in FIG. 5, third cavity 1112c is unused, but this cavity could be used to introduce another polymeric composition in polymeric netting 60.

A polymeric netting such as that indicated by polymeric netting 70 in FIG. 6 can be made, e.g., using a shim sequence shown in FIGS. 18A and 18B. FIGS. 18A and 18B show a perspective assembly of a sequence of shims including shims 200 and 300 as described herein in connection with FIGS. 10 and 11, respectively, and shims 600 and 700, described herein.

Figure 16:
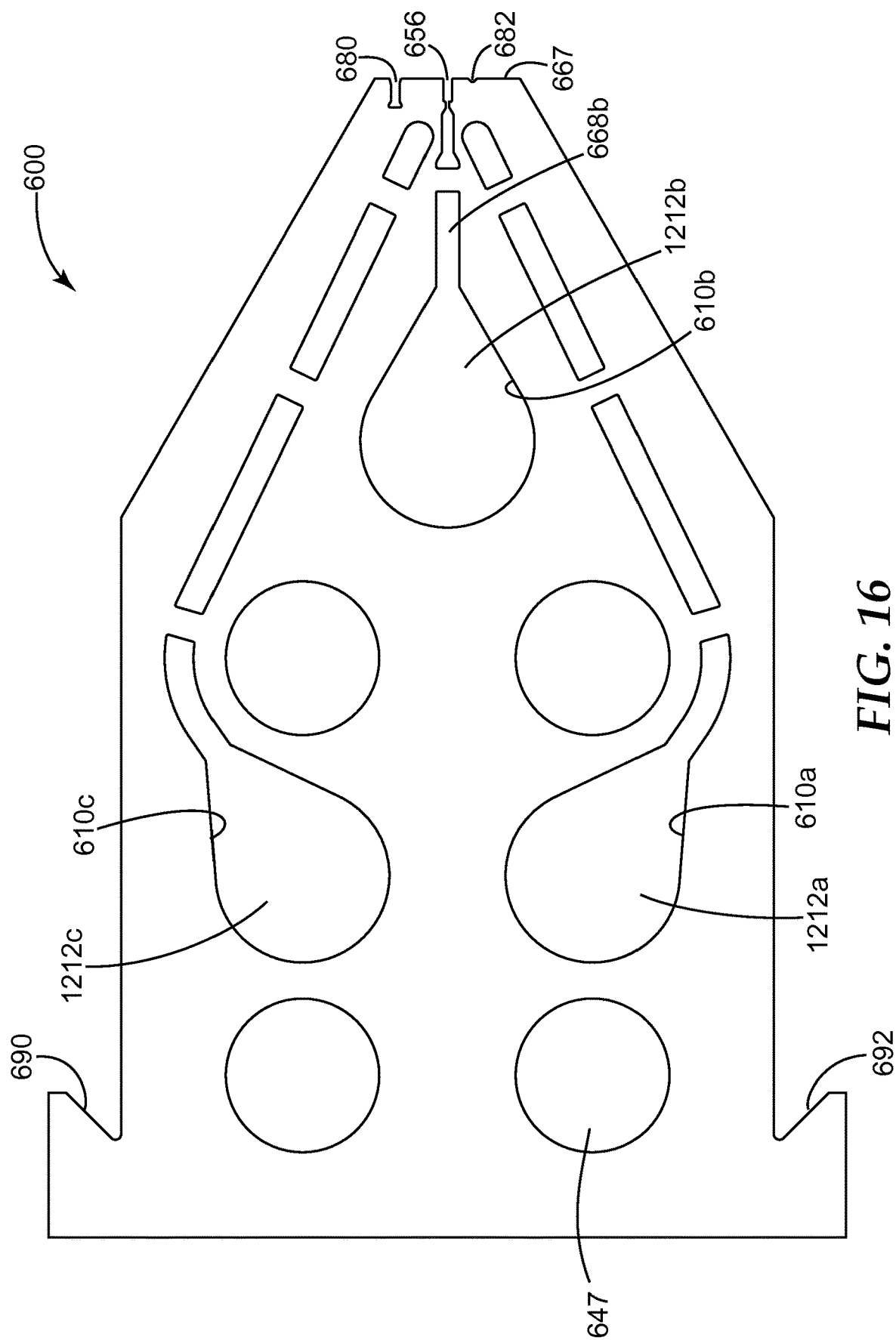
FIG. 16 is a plan view of an embodiment of a shim suitable for a sequence of shims capable of forming a polymeric netting as shown, e.g., in FIG. 6.

Referring now to FIG. 16, a plan view of shim 600 is illustrated. Shim 600 has first aperture 610a, second aperture 610b, and third aperture 610c. When shim 600 is assembled with others as shown in FIG. 18A, aperture 610a helps define first cavity 1212a, aperture 610b helps define second cavity 1212b, and aperture 610c helps define third cavity 1212c. Shim 600 has several holes 647 to allow the passage of, for example, bolts to hold shim 600 and others to be described herein into an assembly. Shim 600 has dispensing surface 667, and in this particular embodiment, dispensing surface 667 has indexing groove 680 and identification notch 682. Shim 600 also has shoulders 690 and 692. Shim 600 has dispensing opening 656 but has no integral connection between dispensing opening 656 and any of apertures 610a, 610b, or 610c. There is no connection, e.g., from aperture 610b to dispensing opening 656, via, for example, passageway 668b, but the flow has a route 1268b to the dispensing surface when shim 600 is assembled with shims 200, 300, and 700 as illustrated in sequence 1200 (see FIG. 18A). The dimensions of 656 can be designed to provide the dimensions desired in the polymer strands extruded therefrom. The dimensions of dispensing opening 656 and the dimensions of passageway leading to it also influence the strand speed.

Figure 17:
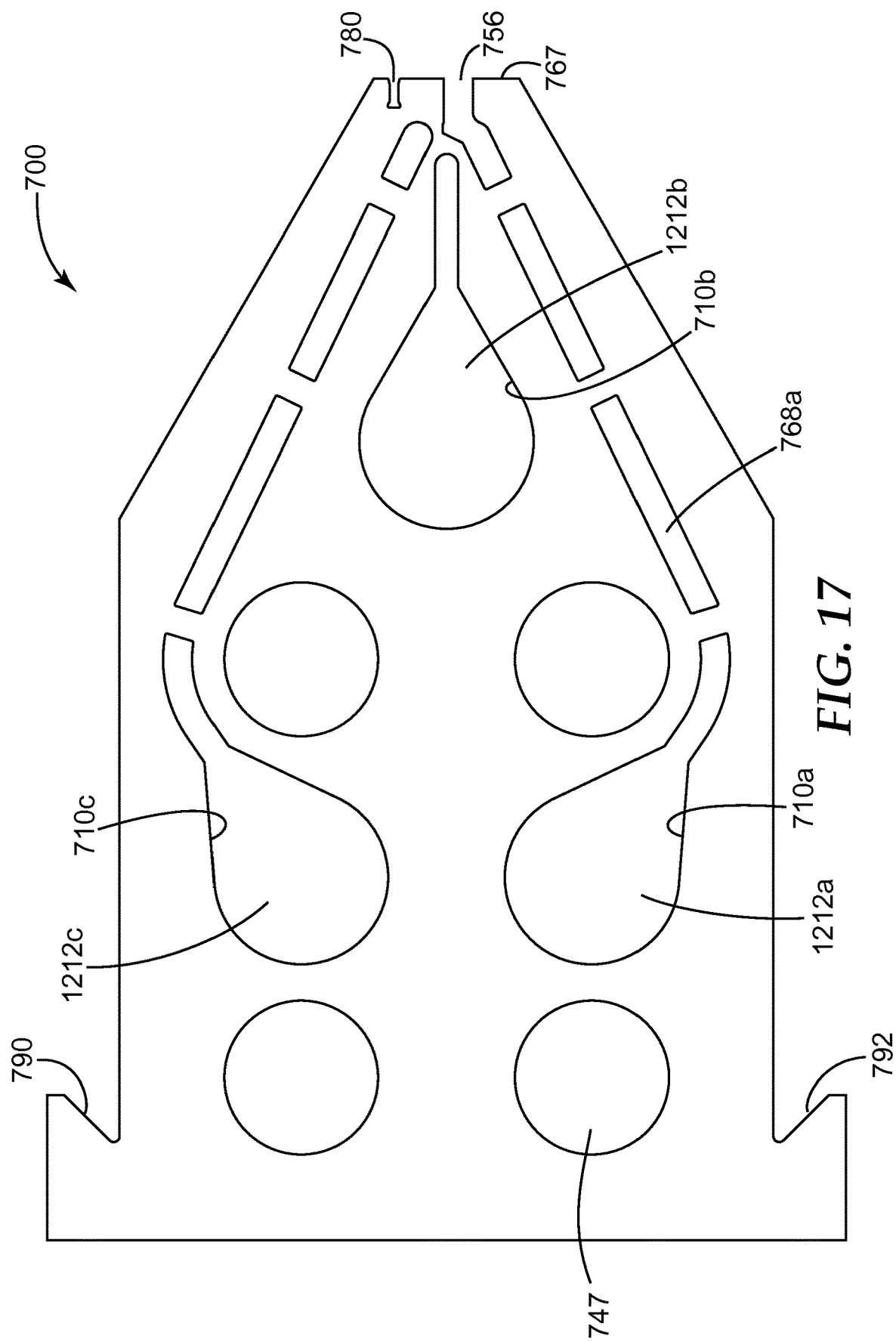
FIG. 17 is a plan view of another embodiment of a shim suitable for a sequence of shims capable of forming a polymeric netting as shown, e.g., in FIG. 6.

Referring now to FIG. 17, a plan view of shim 700 is illustrated. Shim 700 is similar to shim 300, shown in FIG. 11. Shim 700 has first aperture 710a, second aperture 710b, and third aperture 710c. When shim 700 is assembled with others as shown in FIGS. 18A and 18B, aperture 710a helps define first cavity 1212a, aperture 710b helps define second cavity 1212b, and aperture 710c helps define third cavity 1212c. Shim 700 has several holes 747 to allow the passage of, e.g., bolts to hold shim 700 and others to be described herein into an assembly. Shim 700 has dispensing surface 767, and in this particular embodiment, dispensing surface 767 has indexing groove 780. Shim 700 also has shoulders 790 and 792. Shim 700 has dispensing opening 756 but has no integral connection between dispensing opening 756 and any of apertures 710a, 710b, or 710c. There is no connection, for example, from aperture 710a to dispensing opening 756, via, for example, passageway 768a, but the flow has a route 1268a to the dispensing surface when shim 700 is assembled with shims 200, 300, and 600 as illustrated in assembly drawing, e.g., FIG. 18A. As in FIG. 11, dispensing opening 756 is bigger than dispensing opening 656. In some embodiments, dispensing opening 756 is at least twice the size of dispensing opening 656. In some embodiments, dispensing opening 756 is at least 2.5, 3, 5, 10, or 20 times bigger than dispensing opening 656.

FIGS. 18A and 18B illustrate a perspective assembly drawing of a sequence of shims, collectively 1200, employing the shims of FIGS. 10-11 and 16-17 so as to produce a polymeric netting 70 as shown in FIG. 6. Proceeding left to right, the sequence 1200 includes two shims 700 that can extrude polymeric ribbons 81, two shims 200, two shims 600 that can extrude polymeric strands 73, two shims 200, two shims 300 that can extrude polymeric ribbons 71, two shims 200, two shims 600 that can extrude polymeric strands 73, and two shims 200. The first dispensing orifices 1201 each have a height-to-width aspect ratio of at least three to one (in some embodiments, at least 5:1, 8:1, 10:1, 11:1, 15:1, 20:1, 30:1, or 40:1). Dispensing orifices 1201 and 1203 are separated by shims 200, which causes the separation of polymeric ribbons 71 and 81 from polymeric strands 73 in the polymeric netting 70. As in the embodiment shown in FIG. 12B, the height h1201 of the first dispensing orifices is at least 2, 2.5, 3, 5, 10, or 20 times larger than the height h1203 of the second dispensing orifices. In the method disclosed herein polymer from first cavity 1212a emerges as polymeric ribbons 81 from first dispensing orifices 1201, polymer from second cavity 1212b emerges as oscillating strands 73 from second dispensing orifices 1203, and polymer from third cavity 1212c emerges as polymeric ribbons 71 from first dispensing orifices 1201. The dimensions of the fluid passageways and the pressures in the cavities are typically selected so that the speed of oscillating polymeric strands 73 is between about 2 and 6 (in some embodiments, 2 and 4) times greater than the speed of polymeric ribbons 71 and 81.

A polymeric netting such as that indicated by polymeric netting 80 in FIG. 7 can be made, e.g., using a shim sequence shown in FIGS. 21A and 21B. FIGS. 21A and 21B show a perspective assembly of a sequence of shims including shims 200 and 500 as described herein in connection with FIGS. 10 and 14, respectively, and shims 800 and 900, described herein.

Figure 19:
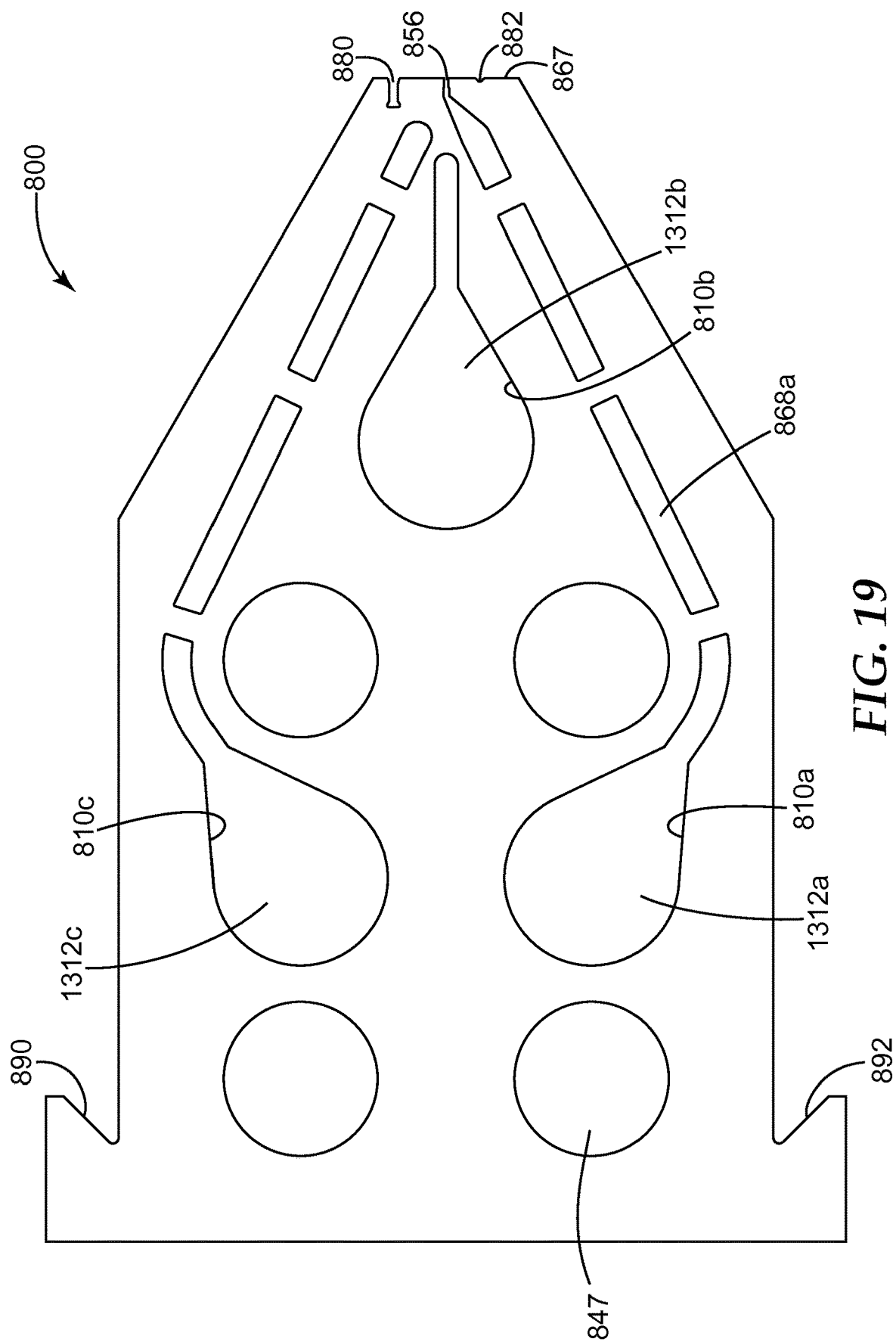
FIG. 19 is a plan view of an embodiment of a shim suitable for a sequence of shims capable of forming a polymeric netting as shown, e.g., in FIG. 7.

Referring now to FIG. 19, a plan view of shim 800 is illustrated. Shim 800 has first aperture 810a, second aperture 810b, and third aperture 810c. When shim 800 is assembled with others as shown in FIGS. 21A and 21B, aperture 810a helps define first cavity 1312a, aperture 810b helps define second cavity 1312b, and aperture 810c helps define third cavity 1312c. Shim 800 has several holes 847 to allow the passage of, e.g., bolts to hold shim 800 and others to be described herein into an assembly. Shim 800 has dispensing surface 867, and in this particular embodiment, dispensing surface 867 has indexing groove 880 and identification notch 882. Shim 800 also has shoulders 890 and 892. Shim 800 has dispensing opening 856 but has no integral connection between dispensing opening 856 and any of apertures 810a, 810b, or 810c. There is no connection, e.g., from aperture 810a to dispensing opening 856, via, e.g., passageway 868a, but the flow has a route 1368a to the dispensing surface when shim 800 is assembled with shims 200, 500, and 900 as illustrated in sequence 1300 (see FIG. 21A).

Figure 20:
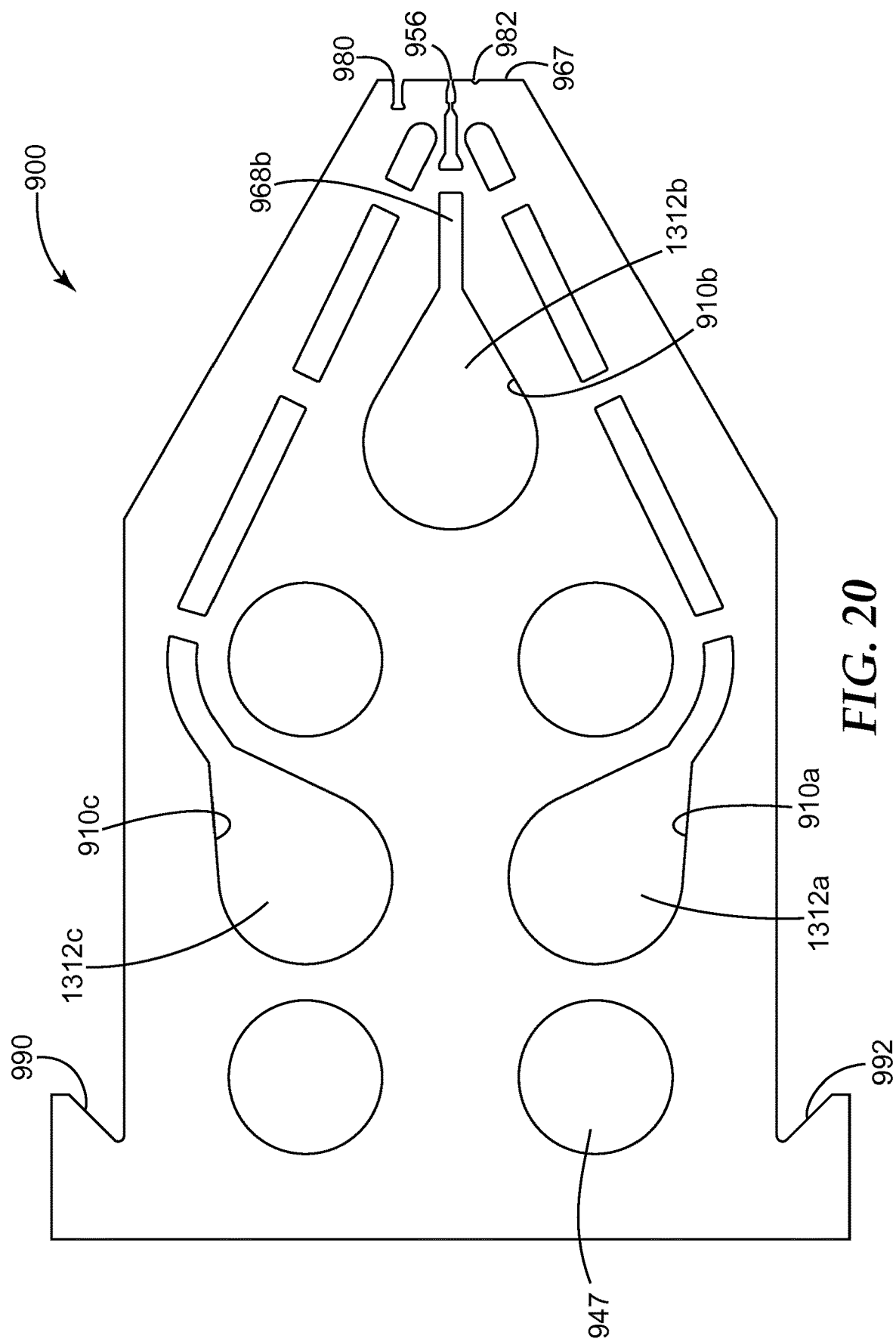
FIG. 20 is a plan view of another embodiment of a shim suitable for a sequence of shims capable of forming a polymeric netting as shown, e.g., in FIG. 7.
Figure 21:
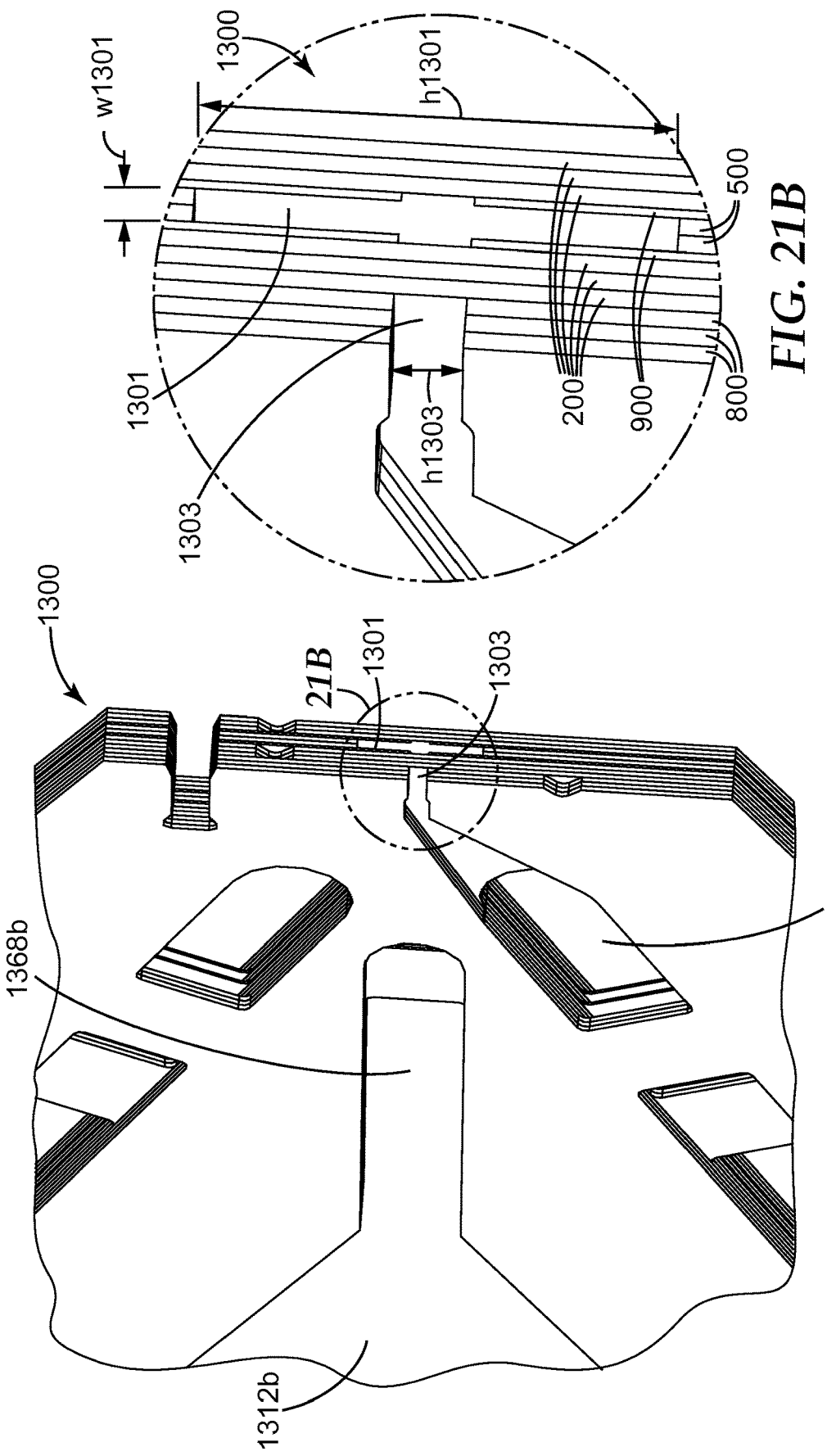
FIG. 21A is a perspective assembly drawing of a sequence of shims employing the shims of FIGS. 10, 14, and 19-20 configured to form a portion of the polymeric netting as shown in FIG. 7.
FIG. 21B is an expanded view of the section referenced as "21B" in FIG. 21A.

Referring now to FIG. 20, a plan view of shim 900 is illustrated. Shim 900 has first aperture 910a, second aperture 910b, and third aperture 910c. When shim 900 is assembled with others as shown in FIGS. 21A and 21B, aperture 910a helps define first cavity 1312a, aperture 910b helps define second cavity 1312b, and aperture 910c helps define third cavity 1312c. Shim 900 has several holes 947 to allow the passage of, e.g., bolts to hold shim 900 and others to be described herein into an assembly. Shim 900 has dispensing surface 967, and in this particular embodiment, dispensing surface 967 has indexing groove 980 and identification notch 982. Shim 900 also has shoulders 990 and 992. Shim 900 has dispensing opening 956 but no integral connection between dispensing opening 956 and any of apertures 910a, 910b, or 910c. There is no connection, e.g., from aperture 910b to dispensing opening 956, via, e.g., passageway 968b, but the flow has a route 1368b to the dispensing surface when shim 900 is assembled with shims 200, 500, and 800 as illustrated in assembly drawing, e.g., FIG. 21A. The dimensions of 956 can be designed to provide the dimensions desired in the polymer strands extruded therefrom. FIGS. 21A and 21B illustrate a perspective assembly drawing of a sequence of shims, collectively 1300, employing the shims of FIGS. 10, 14, 19, and 20 so as to produce a polymeric netting 80 as shown in FIG. 7. Proceeding left to right, the sequence 1300 includes three shims 800 that can extrude polymeric strands 63a, three shims 200, one shim 900 that can extrude a portion of the polymeric ribbons 61a around center line 64a, two shims 500 that can extrude polymeric ribbons 61a, one more shim 900 that can extrude a portion of the polymeric ribbons 61a around center line 64a, and three shims 200. Shim 900 and shim 500 both extrude polymer from cavity 1312b although the dispensing opening 956 is much smaller than dispensing opening 556. Openings 956 and 556 are vertically centered so that more polymer is extruded from cavity 1312b to the central portion of polymeric ribbon 61a. Dispensing orifices 1301 and 1303 are separated by shims 200, which causes the separation of polymeric ribbons 61a from polymeric strands 63a in the polymeric netting 80. The first dispensing orifices 1301 each have a height h1301 to width w1301 aspect ratio of at least three to one (in some embodiments, at least 5:1, 8:1, 10:1, 11:1, 15:1, 20:1, 30:1, or 40:1), when width w1301 is measured at its narrowest point. As in the embodiment shown in FIG. 12B, the height h1301 of the first dispensing orifices is larger (in some embodiments, at least 2, 2.5, 3, 5, 10, or 20 times larger) than the height h1303 of the second dispensing orifices.

In a method using the extrusion die shown in FIGS. 21A and 21B to make a polymeric netting as shown in FIG. 7, e.g., polymer from first cavity 1312a emerges as polymeric strands 63a from second dispensing orifices 1303, and polymer from second cavity 1312b emerges as polymeric ribbons 61a from first dispensing orifices 1301. The dimensions of the fluid passageways and the pressures in cavities 1312a and 1312b are typically selected so that the speed of oscillating polymeric strands 63a is between about 2 and 6 (in some embodiments, 2 and 4) times greater than the speed of polymeric ribbons 61a. To make a polymeric netting as shown in FIG. 7, third cavity 1312c is unused, but this cavity could be used to introduce another polymeric composition in polymeric netting 80.

A modification of the shim sequence shown in FIGS. 21A and 21B may be useful for providing polymeric nettings that are similar to those shown in FIG. 7 but have polymeric ribbons in which more polymer is extruded from cavity 1312b to at least one of the bottom edges 66 or top edges 68 instead of at the central portion 64a.

Figure 22:
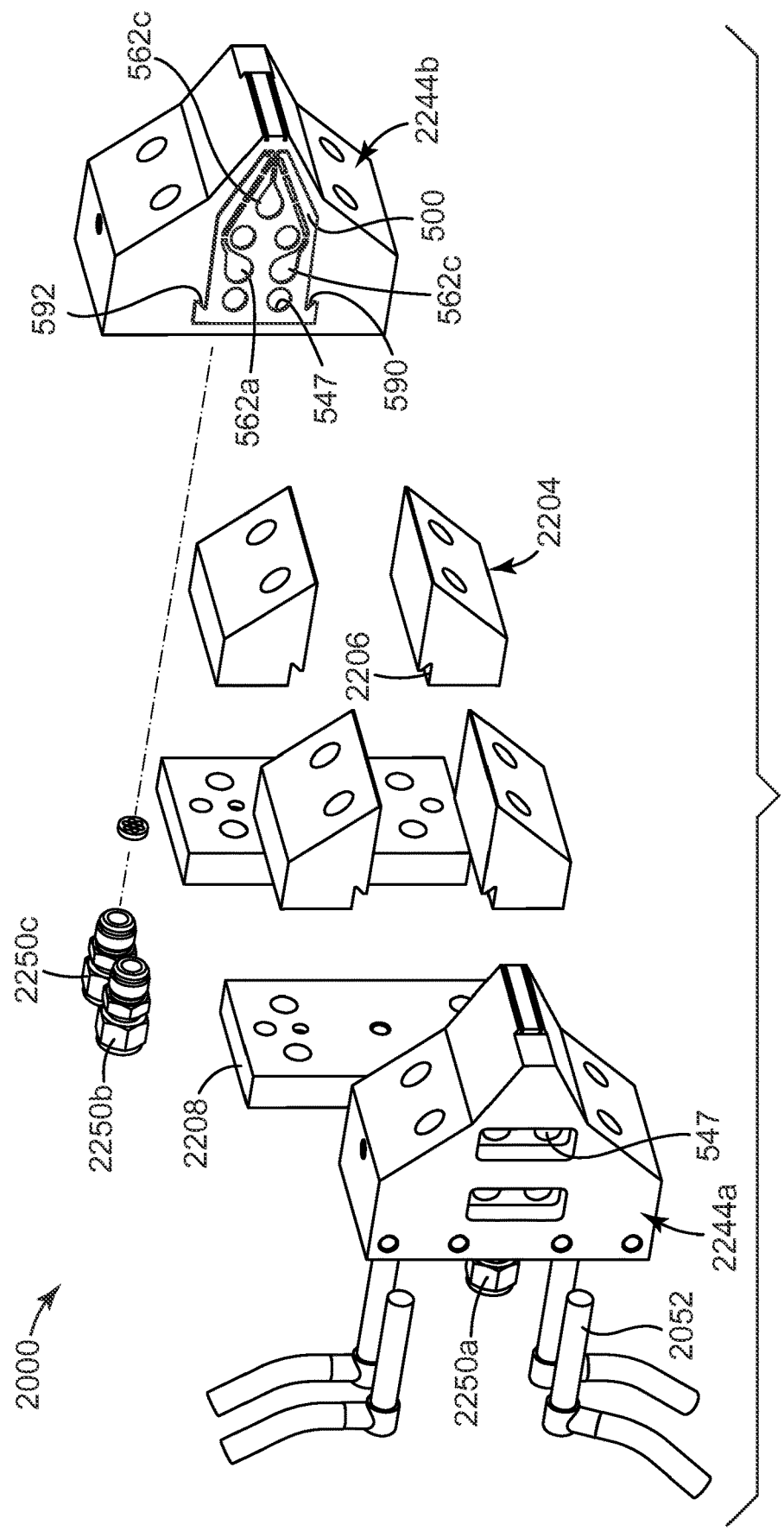
FIG. 22 is an exploded perspective view of an example of a mount suitable for an extrusion die composed of multiple repeats of the sequence of shims shown in FIG. 12A, 15A, 18A, 21A, or 27A.
Figure 23:
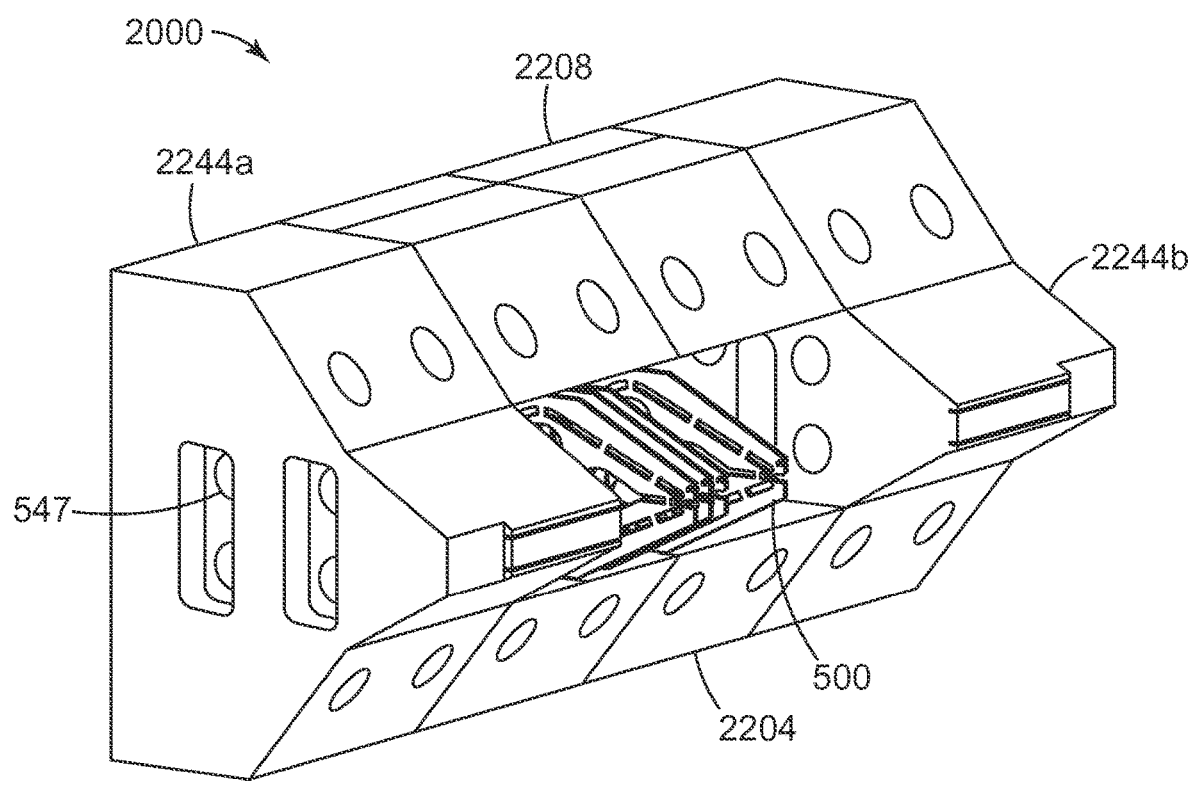
FIG. 23 is a perspective view of the mount of FIG. 22 in an assembled state.

An exploded perspective view of an embodiment of a mount suitable for an extrusion die composed of multiple repeats of the sequence of shims is illustrated in FIGS. 22-23. In one or more embodiments of extrusion dies described herein, there will be a large number of very thin shims (typically several thousand shims; in some embodiments, at least 1000, 2000, 3000, 4000, 5000, 6000, 7000, 8000, 9000, or even at least 10,000), of diverse types (e.g., shims 100, 200, and 300), compressed between two end blocks (e.g., 2244a and 2244b). Conveniently, through bolts can be used to assemble the shims to the end blocks 2244a and 2244b, passing through holes 547 in the shims Inlet fittings 2250a, 2250b, and 2250c are provided on end blocks 2244a and 2244b respectively to introduce the materials to be extruded into extrusion die 2000. In one or more embodiments, inlet fittings 2250a, 2250b, and 2250c are connected to melt trains of conventional type. In one or more embodiments, cartridge heaters 2052 are inserted into receptacles in extrusion die 2000 to maintain the materials to be extruded at a desirable temperature while in the die. The ordinary artisan may perceive alternatives for assembling the extrusion die other than that shown in the illustrated embodiment. In one or more embodiments, the assembled shims (conveniently bolted between the end blocks) further include a manifold body (not shown) for supporting the shims. The manifold body has at least one (or more (e.g., two or three, four, or more)) manifold therein, the manifold having an outlet. An expansion seal (e.g., made of copper or alloys thereof) is disposed so as to seal the manifold body and the shims, such that the expansion seal defines a portion of at least one of the cavities (in one or more embodiments, a portion of all the cavities), and such that the expansion seal allows a conduit between the manifold and the cavity.

Compression blocks 2204 have a notch 2206 that conveniently engages the shoulders on the shims (e.g., shoulders 590 and 592 on shim 500). When mount 2000 is completely assembled, compression blocks 2204 are attached by, e.g., machine bolts to backplates 2208. Referring now to FIG. 23, a perspective view of mount 2000 of FIG. 22 is illustrated in a partially assembled state. A few shims (e.g., shim 500) are in their assembled positions to show how they fit within mount 2000, but most of the shims that would make up an assembled die have been omitted for visual clarity.

In any of the shims and sequences described herein, the shims can have thicknesses in the range from 50 micrometers to 500 micrometers, although thicknesses outside of this range may also be useful. For wider fluid passageways and orifices, several smaller thickness shims may be stacked together, or single shims of the desired passageway width may be used. The shims are typically metal, e.g., stainless steel. To reduce size changes with heat cycling, metal shims are typically heat-treated. The shims can be made by conventional techniques, including wire electrical discharge and laser machining Often, a plurality of shims are made at the same time by stacking a plurality of sheets and then creating the desired openings simultaneously. Variability of the flow channels is preferably within 0.025 mm (1 mil), more preferably, within 0.013 mm (0.5 mil). The shims are tightly compressed to prevent gaps between the shims and polymer leakage. For example, 12 mm (0.5 inch) diameter bolts are typically used and tightened, at the extrusion temperature, to their recommended torque rating. Also, the shims are aligned to provide uniform extrusion out the extrusion orifice, as misalignment can lead to strands extruding at an angle out of the die that inhibits desired bonding of the net. As described herein, to aid in alignment, an indexing groove can be cut into the shims to receive an alignment key. Also, a vibrating table can be useful to provide a smooth surface alignment of the extrusion tip.

Typically, the fluid passageways have heights in a range from 50 micrometers to 3 mm, and lengths less than 5 mm (with generally a preference for smaller lengths for decreasingly smaller passageway thicknesses), although heights and lengths outside of these ranges may also be useful. The height of the first dispensing orifices may be in a range from 50 micrometers to 3 millimeters (mm). In one or more embodiments, the height of the first dispensing orifices is greater than 750 micrometers. In one or more of these embodiments, the height of the first dispensing orifices is in a range from greater than 750 micrometers to 3 mm (e.g., 0.775 mm to 3 mm or 0.8 mm to 2.6 mm). In one or more embodiments, the height of at least one of the first dispensing orifices or the second dispensing orifices is less than 750 micrometers. In one or more of these embodiments, the height of the first dispensing orifices and second dispensing orifices is in a range from 0.1 mm to less than 750 micrometers (e.g., 0.3 mm to 0.745 mm or 0.5 mm to 0.745 mm).

In one or more embodiments of the dies useful for extruding a polymer, each of the first and the second dispensing orifices have a width, and each of the first and the second dispensing orifices is separated by at least the width of the respective dispensing orifice and up to 2 times the width of the respective dispensing orifice. When the dispensing orifices have different widths, the separation between the first and second orifices may be at least the width of the wider opening and up to 2 times the width of the wider opening. The spacing between orifices should be sufficient to maintain a distance between adjacent strands as they exit the die. This spacing accommodates die swell at the dispensing tip. If the spacing between orifices is too great, the strands and ribbons after extrusion at different speeds will not repeatedly collide with each other and will not form the repeating bonds of the polymeric netting In general, it has been observed that the rate of strand bonding is proportional to the extrusion speed of the polymeric strands or ribbons that are extruded at the faster speed. Further, it has been observed that this bonding rate can be increased, for example, by increasing the polymer flow rate for a given orifice size, or by decreasing the orifice area for a given polymer flow rate. It has also been observed that the distance between bonds is inversely proportional to the rate of strand bonding, and proportional to the speed that the net is drawn away from the die. Thus, it is believed that the distance between bonds and the net basis weight can be independently controlled by design of the orifice cross sectional area, the takeaway speed, and the extrusion rate of the polymer. For example, relatively high basis weight nettings, with a relatively short bond pitch can be made by extruding at a relatively high polymer flow rate, with a relatively low netting takeaway speed, using a die with a relatively small second orifice area.

In one or more embodiments, it may be useful to have the number of polymeric ribbons per centimeter of cross direction width vary across the width of the polymeric netting. One way of achieving this is to apply a spreading force to at least a portion of the polymeric netting, such as by running the web over a bowed roller, diverging rails, or diverging disks. Once spread, attaching polymeric netting to another layer (e.g., a carrier or a layer in an absorbent article as described herein) can be useful for maintaining the web in this spread open condition. Spreading in the cross direction causes the openings in the polymeric netting to become larger in the cross direction with the original dimension of the individual openings in the machine direction defined by the average machine direction spacing of contacts between the polymeric ribbons and the polymeric strands. In one or more embodiments, the polymeric netting can be stretched in the machine direction or in both a cross direction and the machine direction to create larger openings and/or to reduce the weight and cost of the polymeric netting on a per unit area basis. Monoaxial stretching in the machine direction, which is the lengthwise direction of the polymeric ribbons and polymeric strands, can be performed by propelling the web over rolls of increasing speed. A versatile stretching method that allows for monoaxial, sequential biaxial, or simultaneous biaxial stretching of a thermoplastic web employs a flat film tenter apparatus. Such an apparatus grasps the web using a plurality of clips, grippers, or other edge-grasping means along opposing edges of the thermoplastic web in such a way that monoaxial, sequential biaxial, or simultaneous biaxial stretching in the desired direction is obtained by propelling the grasping means at varying speeds along divergent rails. Increasing clip speed in the machine direction generally results in machine-direction stretching. Monoaxial and biaxial stretching can be accomplished, e.g., by the methods and apparatuses disclosed in U.S. Pat. No. 7,897,078 to Petersen et al. and the references cited therein. Flat film tenter stretching apparatuses are commercially available, for example, from Brückner Maschinenbau GmbH, Siegsdorf, Germany.

Although in the embodiments shown in FIGS. 9-21, the first and second dispensing orifices are collinear, this is not a requirement. In one or more embodiments, the first dispensing orifices are collinear with each other, and the second dispensing orifices are collinear with each other, but the first and second dispensing orifices do not overlap. When the first and second dispensing orifices do not overlap with each other, it may be desirable to extrude the strands horizontally.

While the embodiments of the extrusion die and method described herein in connection with FIGS. 9-21 supply polymeric ribbons and polymeric strands of a polymer netting from separate cavities, other embodiments include providing an extrusion die including a plurality of shims positioned adjacent to one another, the shims together defining a cavity, the extrusion die having a plurality of first dispensing orifices in fluid communication with the cavity and a plurality of second dispensing orifices in fluid communication with the cavity, such that the first and second dispensing orifices are alternated. In these embodiments, polymeric ribbons are dispensed from the first dispensing orifices at a first speed while simultaneously polymeric strands are dispensed from the second dispensing orifices at a second speed, where the second speed is at least 2 (in some embodiments, in a range from 2 to 6 or 4 to 6) times the first speed. Since there is only one cavity, the polymeric ribbons and polymeric strands in the resulting netting are made from the same composition. To prepare a polymeric netting from an extrusion die having only one cavity, a shim sequence such as that shown in FIGS. 44-48 in PCT Patent Publication No. WO 2013/028654 to Ausen et al. may be useful, with the modification that the shims providing the first dispensing orifices providing the polymeric ribbons have an aspect ratio of at least 5:1 and may lack a restriction set back from the dispensing orifice.

The polymeric compositions useful in the polymeric nettings and methods described herein in any of their embodiments may be the same or different. In some embodiments, the polymeric ribbons and polymeric strands include different polymeric compositions. These nettings can be prepared, e.g., by extrusion using any embodiments of the method described herein by using different polymeric compositions in the first and second cavities. The different polymeric compositions in the polymeric ribbons and polymeric strands may be selected for their surface properties or their bulk properties (e.g., tensile strength, elasticity, microstructure, color, refractive index, etc.). Furthermore, polymeric compositions can be selected to provide specific functional or aesthetic properties in the polymeric netting such as hydrophilicity/hydrophobicity, elasticity, softness, hardness, stiffness, bendability, or colors. The term "different" in terms of polymeric compositions can also refer to at least one of (a) a difference of at least 2% in at least one infrared peak, (b) a difference of at least 2% in at least one nuclear magnetic resonance peak, (c) a difference of at least 2% in the number average molecular weight, or (d) a difference of at least 5% in polydispersity.

In one or more embodiments of the method disclosed herein, polymers used to make the polymeric ribbons and polymeric strands are selected to be compatible with each other such that the polymeric ribbons and polymeric strands bond together at bond regions. Bonding generally refers to melt-bonding, and the bonds between polymer strands and polymer ribbons can be considered to be melt-bonded. The bonding occurs in a relatively short period of time (typically less than 1 second). The bond regions on the major surface of the polymeric ribbons, as well as the polymeric strands, typically cool through air and natural convection and/or radiation. In selecting polymers for the polymeric ribbons and polymeric strands, in one or more embodiments, it may be desirable to select polymers of bonding strands that have dipole interactions (or H-bonds) or covalent bonds. Bonding between strands has been observed to be improved by increasing the time that the polymeric ribbons and polymeric strands are molten to enable more interaction between polymers. Bonding of polymers has generally been observed to be improved by reducing the molecular weight of at least one polymer and or introducing an additional co-monomer to improve polymer interaction and/or reduce the rate or amount of crystallization.

Examples of polymeric materials from which the polymeric netting can be made include thermoplastic polymers. Suitable thermoplastic polymers for the polymeric nettings include polyolefin homopolymers such as polyethylene and polypropylene, copolymers of ethylene, propylene and/or butylene; copolymers containing ethylene such as ethylene vinyl acetate and ethylene acrylic acid; ionomers based on sodium or zinc salts of ethylene methacrylic acid or ethylene acrylic acid; polyvinyl chloride; polyvinylidene chloride; polystyrenes and polystyrene copolymers (styrene-maleic anhydride copolymers, styrene acrylonitrile copolymers); nylons; polyesters such as poly(ethylene terephthalate), polyethylene butyrate and polyethylene napthalate; polyamides such as poly(hexamethylene adipamide); polyurethanes; polycarbonates; poly(vinyl alcohol); ketones such as polyetheretherketone; polyphenylene sulfide; polyacrylates; cellulosics; fluoroplastics; polysulfones; silicone polymers; and mixtures thereof. The die and method according to the present disclosure may also be useful for co-extruding polymeric materials that can be crosslinked (e.g., by heat or radiation). When a heat curable resin is used, the die can be heated to start the cure so as to adjust the viscosity of the polymeric material and/or the pressure in the corresponding die cavity. In some embodiments, at least one of the polymeric ribbons or polymeric strands is made from a polyolefin (e.g., polyethylene, polypropylene, polybutylene, ethylene copolymers, propylene copolymers, butylene copolymers, and copolymers and blends of these materials).

In one or more embodiments, the polymeric ribbons are elastic, the polymeric strands are elastic, or both the polymeric ribbons and polymeric strands are elastic. For example, the second polymeric composition may include thermoplastic elastomers such as ABA block copolymers, polyurethane elastomers, polyolefin elastomers (e.g., metallocene polyolefin elastomers), polyamide elastomers, ethylene vinyl acetate elastomers, polyvinyl ethers, acrylics, especially those having long chain alkyl groups, poly-alpha-olefins, asphaltics, silicones, polyester elastomers, and natural rubber. An ABA block copolymer elastomer generally is one where the A blocks are polystyrenic, and the B blocks are conjugated dienes (e.g., lower alkylene dienes). The A block is generally formed predominantly of substituted (e.g., alkylated) or unsubstituted styrenic moieties (e.g., polystyrene, poly(alphamethylstyrene), or poly(t-butylstyrene)), having an average molecular weight from about 4,000 to 50,000 grams per mole. The B block(s) is generally formed predominantly of conjugated dienes (e.g., isoprene, 1,3-butadiene, or ethylene-butylene monomers), which may be substituted or unsubstituted, and has an average molecular weight from about 5,000 to 500,000 grams per mole. The A and B blocks may be configured, e.g., in linear, radial, or star configurations. An ABA block copolymer may contain multiple A and/or B blocks, which blocks may be made from the same or different monomers. A typical block copolymer is a linear ABA block copolymer, where the A blocks may be the same or different, or a block copolymer having more than three blocks, predominantly terminating with A blocks. Multi-block copolymers may contain, for example, a certain proportion of AB diblock copolymer, which tends to form a more tacky elastomeric film segment. Other elastic polymers can be blended with block copolymer elastomers, and various elastic polymers may be blended to have varying degrees of elastic properties.

Many types of thermoplastic elastomers are commercially available, including those from BASF, Florham Park, N.J., under the trade designation "STYROFLEX," from Kraton Polymers, Houston, Tex., under the trade designation "KRATON," from Dow Chemical, Midland, Mich., under the trade designation "PELLETHANE," "ENGAGE," "INFUSE," "VERSIFY," or "NORDEL," from DSM, Heerlen, Netherlands, under the trade designation "ARNITEL," from E. I. duPont de Nemours and Company, Wilmington, Del., under the trade designation "HYTREL," from ExxonMobil, Irving, Tex. under the trade designation "VISTAMAXX," and more.

Mixtures of any of the above-mentioned polymers may be useful in the polymeric nettings disclosed herein. For example, a polyolefin may be blended with an elastomeric polymer to lower the modulus of the polymeric composition, which may be desirable for certain applications. Such a blend may or may not be elastic.

In some embodiments, polymeric materials from which polymeric netting can be made include a colorant (e.g., pigment and/or dye) for functional (e.g., optical effects) and/or aesthetic purposes (e.g., each has different color/ shade). Suitable colorants are those known in the art for use in various polymeric materials. Exemplary colors imparted by the colorant include white, black, red, pink, orange, yellow, green, aqua, purple, and blue. In some embodiments, it is desirable to have a certain degree of opacity for one or more of the polymeric materials. The amount of colorant(s) to be used in specific embodiments can be readily determined by those skilled in the (e.g., to achieve desired color, tone, opacity, transmissivity, etc.).

The shape of the individual polymeric ribbons and polymeric strands in a polymeric netting disclosed herein can depend on a variety of factors. As described herein, the polymeric strands, which are lower in height than the polymeric ribbons, may exit the die at a faster rate than the polymeric ribbons and may be oscillating. Therefore, in some embodiments, the polymeric ribbons may be substantially straight, for example, when no extension force is placed on the polymeric netting as shown, e.g., in FIGS. 31A, 32A, and 33A. However, depending on the difference in height between the polymeric ribbons and strands, the placement of the polymeric strands on the major surface of the polymeric ribbons, and the modulus of the materials from which the polymeric ribbons and polymeric strands are made, both the polymeric ribbons and polymeric strands may occupy a sinusoidal path in the lengthwise direction as shown, e.g., in FIG. 2. In some embodiments, the polymeric ribbons may exit the die at a faster rate than the polymeric strands and may be oscillating. In these embodiments, the polymeric strands may appear substantially straight, for example, when no extension force is placed on the polymeric netting.

In one or more embodiments, a single strand of the polymeric strands or a single ribbon of the polymeric ribbons in the netting may include different polymeric compositions. For example, one or more of the polymeric strands in the polymeric netting may have a core made of one polymeric composition and a sheath of a different polymeric composition. Such nets can be extruded as described in PCT Patent Publication No. WO 2013/032683 to Ausen et al. Nettings in which their opposing major surfaces are made from different polymeric compositions are described in co-pending Application Ser. No. 61/779,997, filed Mar. 13, 2013.

As described herein in connection with FIG. 8, in one or more embodiments, the polymeric ribbons each have a center line bisecting the major surface and first and second edges symmetrically disposed on opposite sides of the center line, wherein the first edges of the polymeric ribbons include a different composition than the second edges of the polymeric ribbons. In the illustrated embodiment, the polymeric strands also have a center line bisecting a major surface and first and second edges symmetrically disposed on opposite sides of the center line, where the first edges of the polymeric strands include a different composition than the second edges of the polymeric strands. A polymeric netting such as that indicated by polymeric netting 90 in FIG. 8 can conveniently be made, for example, using a shim sequence 3000 shown in FIGS. 27A and 27B. FIGS. 27A and 27B show a perspective assembly of a sequence of shims including shims 3100, 3200, and 3300, described herein.

Figure 24:
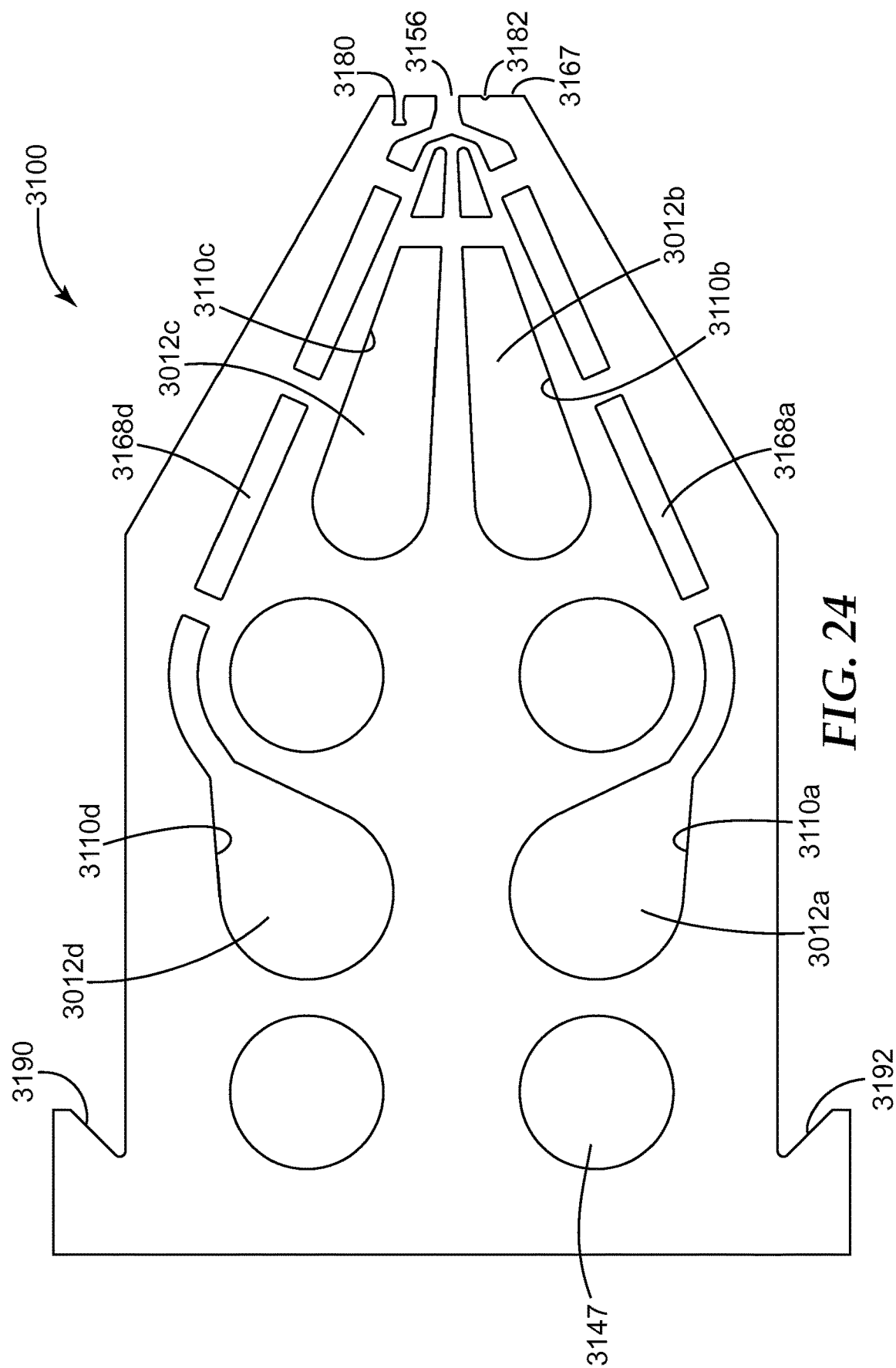
FIG. 24 is a plan view of an embodiment of a shim suited to form a sequence of shims useful for making a polymeric netting as shown, for example, in FIG. 8.

Referring now to FIG. 24, a plan view of shim 3100 is illustrated. Shim 3100 has first aperture, 3110*a*, second aperture 3110*b*, a third aperture 3110*c*, and a fourth aperture 3110*d*. When shim 3100 is assembled with others as shown in FIGS. 27A and 27B, first aperture 3110*a* will help define first cavity 3012*a*, second aperture 3110*b* will help define second cavity 3012*b*, third aperture 3110*c* will help define third cavity 3012*c*, and fourth aperture 3110*d* will help define fourth cavity 3012*d*. As will be discussed with more particularity herein, molten polymer in cavities 3012*a* and 3012*d* can be extruded into polymeric ribbons 91 having two layers 91*a* and 91*b*, and molten polymer in cavities 3012*b* and 3012*c* can be extruded into polymeric strands 93 having two layers 93*a* and 93*b* as shown in FIG. 8.

Shim 3100 has several holes 3147 to allow the passage of, e.g., bolts to hold shim 3100 and others to be described herein into an assembly. Shim 3100 has dispensing opening 3156 in dispensing surface 3167. It might appear that there are no paths from apertures 3110*a* and 3110*d* to dispensing opening 3156, via, e.g., passageways 3168*a* and 3168*d*, but the flows have routes 3068*a* and 3068*d* in the perpendicular-to-the-plane-of-the-shim dimension when the sequence of FIG. 27A, for example, is completely assembled. Similar to shim 100, dispensing surface 3167 of shim 3100 has indexing groove 3180, identification notch 3182, and shoulders 3190 and 3192.

Figure 25:
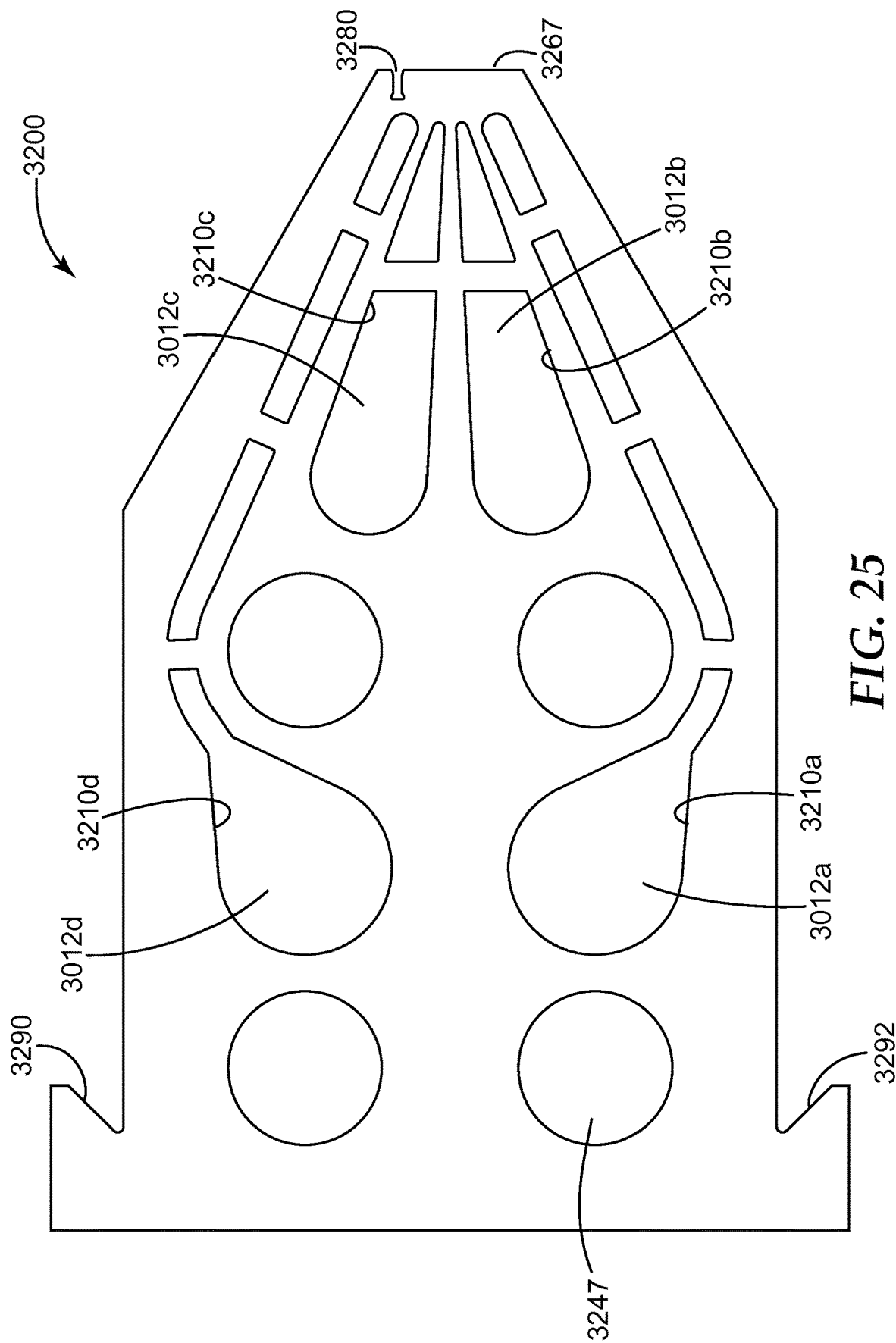
FIG. 25 is a plan view of another embodiment of a shim suited to form a sequence of shims useful for making a polymeric netting as shown, e.g., in FIG. 8.

Referring now to FIG. 25, a plan view of shim 3200 is illustrated. Shim 3200 has first aperture, 3210*a*, second aperture 3210*b*, third aperture 3210*c*, and fourth aperture 3210*d*. When shim 3200 is assembled with others as shown in FIGS. 27A and 27B, first aperture 3210*a* will help define first cavity 3012*a*, second aperture 3210*b* will help define second cavity 3012*b*, third aperture 3210*c* will help define third cavity 3012*c*, and fourth aperture 3210*d* with help define fourth cavity 3012*d*. Analogous to shim 3100, shim 3200 has dispensing surface 3267, and in this particular embodiment, dispensing surface 3267 has indexing groove 3280. Also analogous to shim 3100, shim 3200 has shoulders 3290 and 3292. There is no passage from any of the cavities to dispensing surface 3267 since this shim creates a non-dispensing area along the width of the die. Referring again to FIG. 8, shim(s) 3200 are useful for separating shims 3100 producing polymeric ribbons 91 from shims 3300 producing polymeric strands 93.

Figure 26:
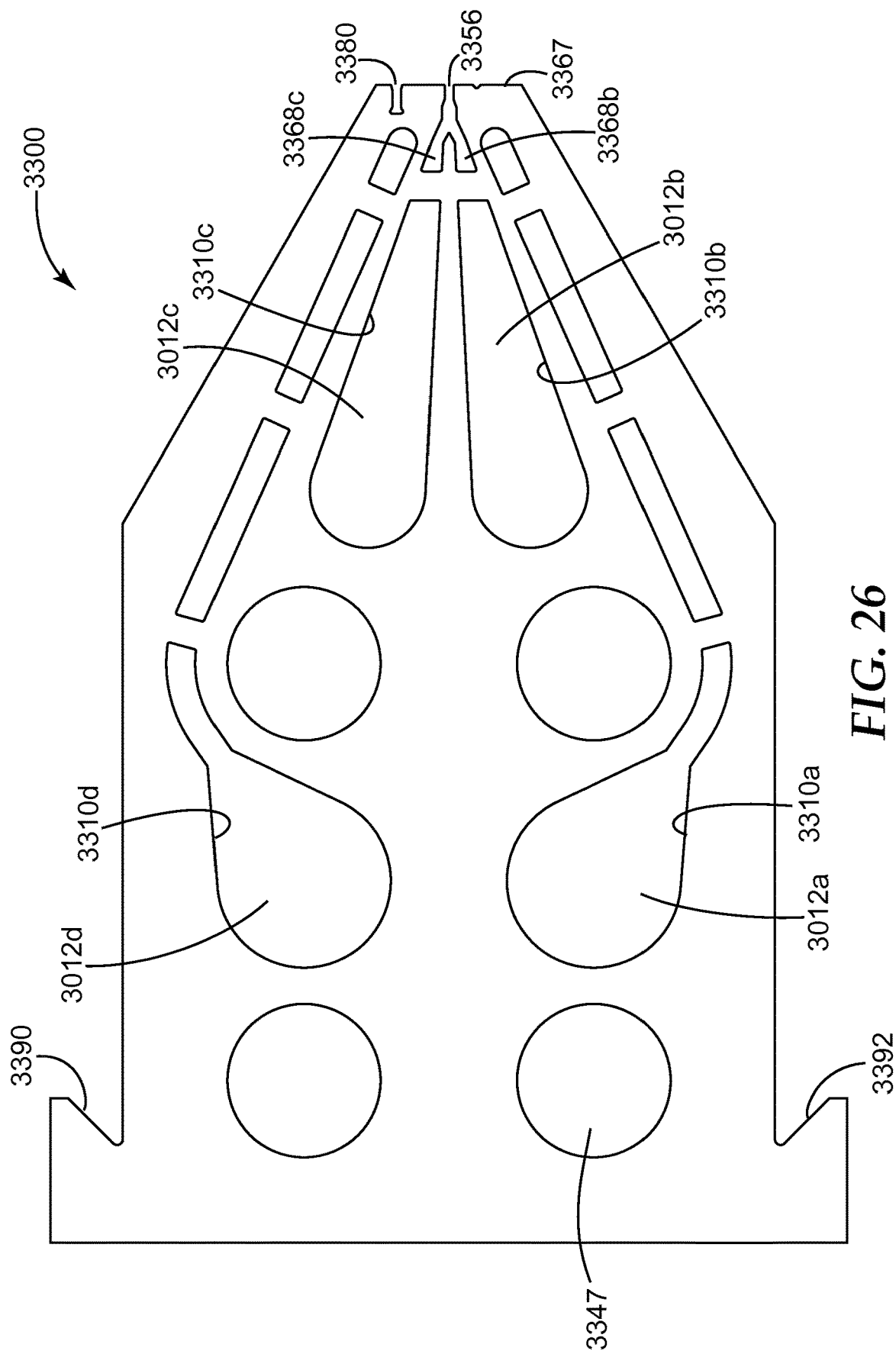
FIG. 26 is a plan view of yet another embodiment of a shim suited to form a sequence of shims useful for a polymeric netting as shown, e.g., in FIG. 8.
Figure 27:
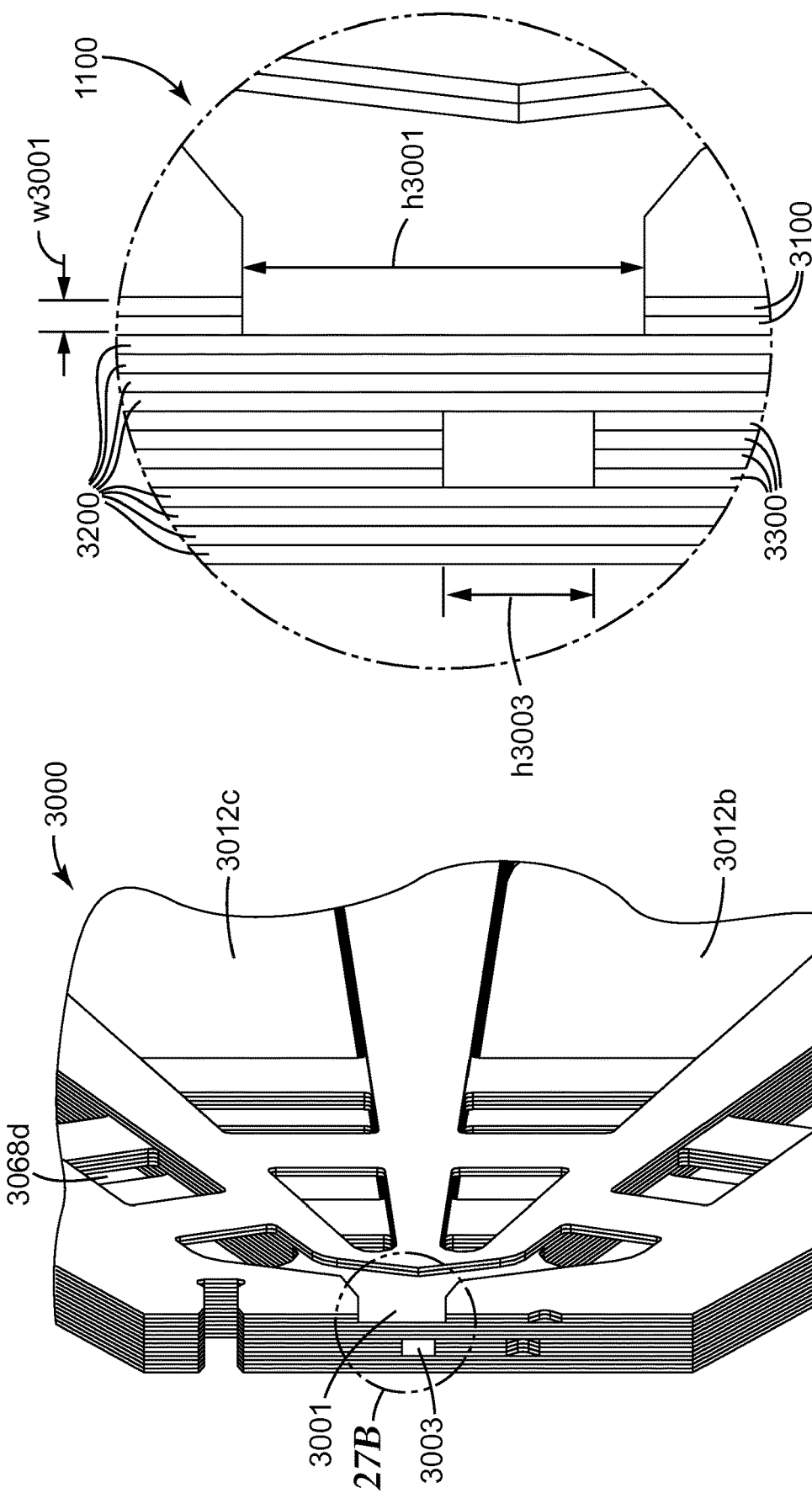
FIG. 27A is a perspective drawing of a sequence of shims employing the shims of FIGS. 24-26 configured to form a portion of a polymeric netting as shown, e.g., in FIG. 8.
FIG. 27B is an expanded view of the section referenced as "27B" in FIG. 27A.

Referring now to FIG. 26, a plan view of shim 3300 is illustrated. Shim 3300 has first aperture 3310*a*, second aperture 3310*b*, third aperture 3310*c*, and fourth aperture 3310d. When shim 3300 is assembled with others as shown in FIGS. 27A and 27B, first aperture 3310a will help define first cavity 3012a, second aperture 3310b will help define second cavity 3012b, third aperture 3310c will help define third cavity 3012c, and fourth aperture 3310d with help define fourth cavity 3012d. Analogous to shim 3100, shim 3300 has dispensing surface 3367, and in this particular embodiment, dispensing surface 3367 has indexing groove 3280 and identification notch 3282. Also analogous to shim 3100, shim 3300 has shoulders 3390 and 3392. Shim 3300 has dispensing opening 3356 in dispensing surface 3367. It might appear that there are no paths from apertures 3010b and 3010c to dispensing opening 3356, via, for example, passageway 3368b and 3368c, respectively, but the flows have routes in the perpendicular-to-the-plane-of-the-shim dimension when the sequence of FIG. 27A, for example, is completely assembled.

Referring now to FIGS. 27A and 27B, a perspective assembly drawing of a sequence of shims, collectively 3000, employing the shims of FIGS. 24-26 so as to produce polymeric netting 90 shown in FIG. 8 is shown. More particularly, proceeding from left to right in FIG. 27B, sequence 3000 includes four instances of shim 3200, four instances of shim 3300 that can extrude polymeric strands 93, four instances of shim 3200, and two instances of shim 3100 that can extrude polymeric ribbons 91. Dispensing orifices 3001 and 3003 are separated by shims 3200, which causes the separation of polymeric ribbons 91 from polymeric strands 93 in the polymeric netting 90. The first dispensing orifices 3001 each have a height h3001 to width w3001 aspect ratio of at least three to one (in some embodiments, at least 5:1, 8:1, 10:1, 11:1, 15:1, 20:1, 30:1, or 40:1). In FIG. 27B, the width of the first dispensing orifices can be considered to be the width of two shims 3100. As in the embodiment shown in FIG. 12B, the height h3001 of the first dispensing orifices 3001 is at least 2, 2.5, 3, 5, 10, or 20 times larger than the height h3003 of the second dispensing orifices. In this embodiment, at least the first dispensing orifices 3001 are defined by an array of first vestibules, and the die includes a first fluid passageway 3168a between the first cavity 3012a and one of the first vestibules, and a fourth passageway 3168d extending from the fourth cavity 3012d to the same vestibule, such that the area where the first fluid passageway 3168a enters the first vestibules is below the area where the fourth fluid passageway 3168d enters the first vestibules. The extrusion die also includes fluid passageways extending from one of the cavities with the die to the second dispensing orifices. In the illustrated embodiment, the second dispensing orifices 3003 are defined by an array of second vestibules, and the die includes a second fluid passageway 3168b between the second cavity 3012b and one of the second vestibules, and a third passageway 3168c extending from a third cavity 3012c to the same vestibule, such that the area where the second fluid passageway 3168b enters the second vestibules is below the area where the third fluid passageway 3168c enters the second vestibules.

In other embodiments in which the first edges of the polymeric ribbons include a different composition than the second edges of the polymeric ribbons, the polymeric netting can be surface treated with a surfactant (e.g., in an amount between about 0.05 and 0.5 weight percent). If a surfactant is used, it can be an internal additive in a polymeric composition that migrates to the surface, or a surfactant can be applied to the web by any conventional means (e.g., spraying, printing, dipping, or brush coating). Polymer compositions (e.g., those providing second portions 91b and 93b shown in FIG. 8) may be selected to be hydrophilic or to include a surfactant, or a surfactant can be applied to a major surface of the polymeric netting to impart a desired level of wettability and hydrophilicity to at least a portion of the polymeric netting for certain applications.

In any of the aforementioned embodiments of the polymeric netting according to and/or made from the method according to the present disclosure, the distance between bonds can be in a range from 0.5 mm to 20 mm (in some embodiments, in a range from 0.5 mm to 10 mm). Also, in any of the aforementioned embodiments, the polymeric netting according to the present disclosure or made from the methods disclosed herein can have a basis weight in a range from 5 g/m² to 750 g/m² (in some embodiments, 5 g/m² to 400 g/m² or 10 g/m² to 200 g/m²). In some embodiments, the polymeric netting disclosed herein in any of the aforementioned embodiments has a thickness up to 4 mm (in some embodiments, up to 3.5 mm, 3 mm, 2 mm, 1 mm, 0.75 mm, or less than 0.75 mm; in a range from 10 micrometers to 4 mm, 10 micrometers to 3.5 mm, 10 micrometers to 3 mm, 10 micrometers to 2 mm, 10 micrometers to 1 mm, 10 micrometers to 750 micrometers, 10 micrometers to less than 750 micrometers, 10 micrometers to 749 micrometers, 10 micrometers to 700 micrometers, or 10 micrometers to 650 micrometers.

Figure 28:
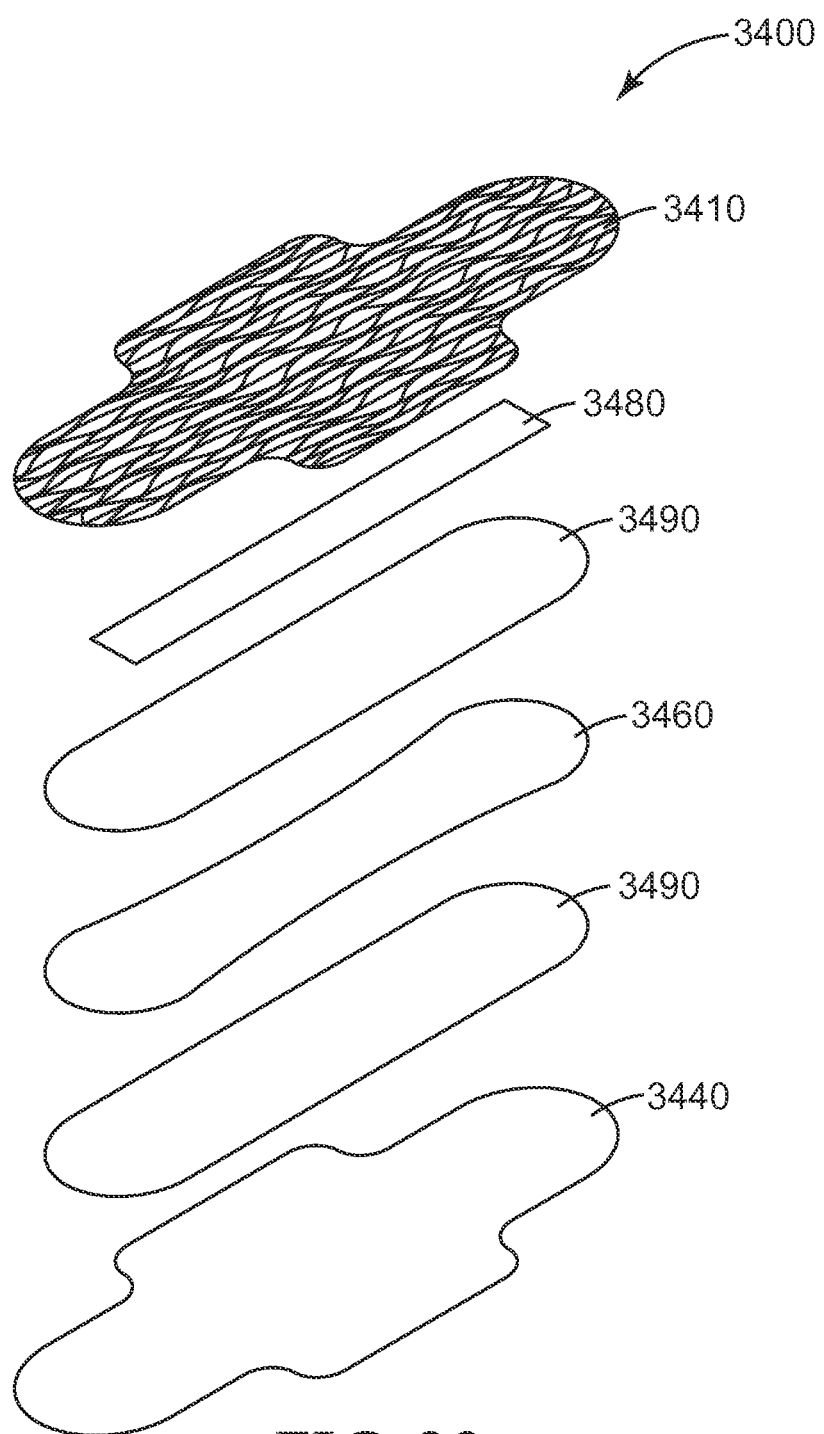
FIG. 28 is a schematic exploded view of an example of an absorbent article according to the present disclosure.

The polymeric netting according to and/or made according to the present disclosure is useful, for example, in absorbent articles. Accordingly, the present disclosure provides an absorbent article including a polymeric netting according to the present disclosure. Personal care absorbent articles, such as diapers, training pants, adult incontinence garments, and feminine hygiene pads (e.g., sanitary napkins and pantyliners) and wound care absorbent articles (e.g., wound dressings and bandages) are often constructed using a skin-facing fluid pervious topsheet, a garment-facing fluid impervious backsheet, and an absorbent core positioned therebetween. An exploded schematic view of an example of an embodiment of an absorbent article 3400 according to the present disclosure is shown in FIG. 28. In absorbent articles according to the present disclosure, the absorbent core 3460 is typically interposed between the polymeric netting and the backsheet 3440. The polymeric netting can be useful, for example as at least one of a topsheet 3410 or acquisition/distribution layer 3480. In the illustrated embodiment, the polymeric netting forms topsheet 3410. When used as an acquisition/distribution layer 3480, the polymeric netting may also be located between the absorbent core 3460 and the backsheet 3440 or within the absorbent core 3460 (e.g., between two tissue sheets 3490).

Polymeric netting according to the present disclosure advantageously can be used as a topsheet in an absorbent article. Referring to FIG. 28, the topsheet 3410 is the layer against the user's skin and so the first layer in contact with liquid or other exudate from the user. The topsheet desirably serves several purposes including keeping the absorbent material contained within the article, allowing fluids to rapidly pass through to the absorbent core, providing a skin friendly, comfortable contact surface for the skin contacted by the article, keeping the skin clean and dry, and helping to prevent absorbed fluid from coming into contact with the skin. When used as a topsheet 3410 for hygiene articles, the polymeric netting may have a configuration as shown in any one of FIGS. 1-4 and 8, for example. In these configurations, the polymeric ribbons 1 each have a center line 4 bisecting the first major surface 2 and first and second edges 6, 8 symmetrically disposed on opposite sides of the center line 4, wherein the polymeric strand 3 is bonded to the first major surface 2 at a location closer to the first edges 6 than the second edges 8. In other words, referring to FIG. 3, the polymeric strands 33 are all disposed toward the same first edges of the polymeric ribbons 31, 41 so that both the polymeric ribbons and polymeric strands can contact absorbent 47. This configuration also provides greater surface area on one side of the polymeric netting 40 for adhesive bonding the netting to the absorbent. However, in other embodiments, the configuration shown in FIGS. 5-7 may be useful.

In any of the configurations shown in FIGS. 1-7, the Examples below indicate that in some embodiments, the polymeric netting can have at least one of the following features: capable of rapid fluid uptake, directs the fluid in the machine direction of the material, offers a high degree of resistance to rewet, presents a dry to the touch skin facing surface after exposure to fluids, and due to the flexibility of the ribbon like element provides a cleansing action to the skin, driven by natural body motions, resulting in cleaner and drier skin for the wearer of an absorbent hygiene article utilizing this new topsheet material.

In an absorbent article 3400 according to the present disclosure as illustrated in FIG. 28, the backsheet 3440, sometimes referred to as the outer cover, is the farthest layer from the user. The backsheet is typically formed of a thin thermoplastic film (e.g., polyethylene film) which is substantially impermeable to liquid. The backsheet functions to prevent body exudates absorbed by the absorbent core from wetting or soiling the wearer's clothing, bedding, or other materials contacting the absorbent article. A variety of materials for the backsheet may be suitable in an absorbent article according to the present disclosure. For example, the backsheet may include a polyethylene film (e.g., having an initial thickness of about 0.5 mil (0.012 millimeter) to about 5.0 mil (0.12 millimeter)), a woven or nonwoven fibrous web constructed or treated to impart the desired level of liquid impermeability, a laminate of a woven or nonwoven fabric and thermoplastic film, or a vapor or gas permeable microporous "breathable" material that is substantially impermeable to liquid. Films useful as backsheets, for example, may be embossed and/or matte finished to provide a more aesthetically pleasing appearance.

In an absorbent article according to the present disclosure, the absorbent core (e.g., 3460 as shown in FIG. 28) typically includes a natural, synthetic, or modified natural organic polymer that can absorb and hold liquids (e.g., aqueous liquids). In one or more embodiments, the polymer is crosslinked. The term "crosslinked" refers to any means for effectively rendering normally water-soluble materials substantially water insoluble but swellable. Such absorbent materials are usually designed to quickly absorb liquids and hold them, usually without release. The size and the absorbent capacity of the absorbent core are typically compatible with the size of the intended wearer and the liquid loading imparted by the intended use of the absorbent article. Various absorbents may be useful, e.g., a cellulosic material (e.g., wood pulp fluff), hydrophilic, synthetic meltblown fibers, superabsorbent polymer (SAP), an acrylic foam absorbent (e.g., foams described in U.S. Pat. No. 5,817,704 to Shiveley et al. and the references cited therein, prepared, e.g., by polymerization of high internal phase emulsions), and any combination thereof. Absorbent materials may be zoned and their compositions chosen to move liquids away from the original location of the incoming insult to more remote storage locations. In some embodiments, the absorbent core can include one or more substantially hydrophilic tissue sheets 3490 to help maintain the integrity, for example, of the structure of the absorbent core. The tissue sheet(s), which may be one tissue sheet wrapped around to provide two major facing surfaces of the absorbent core, can include absorbent cellulosic material (e.g., creped wadding or a high wet-strength tissue). In one or more embodiments, the tissue sheet can be configured to rapidly distribute liquid over the absorbent core. In these embodiments, the tissue sheet may be considered a distribution layer, which moves fluid from the point of initial deposition to the location where storage is desired.

Some absorbent articles include an acquisition layer 3480, which can be useful for quickly accepting an incoming insult and either absorb, hold, channel, or otherwise manage the liquid so that it does not leak outside the article. The acquisition layer may also be referred to, for example, as a surge layer, intake layer, transfer layer, or transport layer. An acquisition layer is generally capable of handling an incoming insult of between about 60 and 100 milliliters (mL) at an insult volumetric flow rate of from about 5 to 20 mL/second, for infants, for example. An acquisition layer is generally subjacent the topsheet at the surface opposite the user's skin. Various woven and nonwoven webs and foams can be used to construct an acquisition layer. Acquisition layers may be composed of a substantially hydrophobic material, and the hydrophobic material may optionally be treated with a surfactant or otherwise processed to impart a desired level of wettability and hydrophilicity. In some embodiments, acquisition layer 3480 can have a generally uniform thickness and cross-sectional area. The polymeric netting according to the present disclosure may be useful as an acquisition layer in combination with a conventional topsheet (e.g., a nonwoven or an apertured film as described herein) as a topsheet in combination with a conventional acquisition layer, or in some embodiments as a replacement for both a conventional topsheet and acquisition layer. In other words, when the polymeric netting according to the present disclosure is used as a topsheet, the need for the acquisition layer may be eliminated.

Suitable conventional attachment techniques may be useful for assembling an absorbent article according to the present disclosure. When used as a topsheet 3410, the polymeric netting according to the present disclosure may be attached to the absorbent core 3460 or the acquisition layer 3480 (if used) using at least one of adhesive bonding (e.g., using water-based, solvent-based, or thermally activated adhesives), thermal bonding, ultrasonic bonding, needling, or pin aperturing. When used as an acquisition layer 3480, the polymeric netting according to the present disclosure can be attached to both the conventional topsheet and the absorbent core 4060 also using any one of these methods. If adhesive bonding is used, the amount of adhesive add-on should be sufficient to provide the desired level(s) of bonding, without excessively restricting the flow of liquid into the absorbent core 4060.

When used as a topsheet in an absorbent article, the polymeric netting can overcome disadvantages of conventional topsheet materials. For diapers, incontinence articles, and feminine hygiene pads the conventional types of topsheet, generally fall into two main groups: nonwovens and apertured films. Nonwovens have the advantage of being soft and cloth-like in feel. Nonwovens can be made hydrophilic (e.g., by treating with surfactant) to allow rapid fluid transport through the nonwoven to the absorbent. Such hydrophilic materials tend to cause user to feel wetness possibly due to small amounts of fluid being retained in the nonwoven. Retained fluid in the nonwoven also makes the fluid more visible, which is undesirable. Some hydrophilic nonwovens also have a tendency to direct fluids toward the lateral edges of the pad, potentially contributing to side leakage. To achieve the goals of softness and dry feel in nonwoven topsheets, sometimes the nonwoven is made of hydrophobic fibers. The use of hydrophobic fibers typically results in improved dry feel, but hydrophobic nonwovens may not allow rapid fluid transport into the pad. Sometimes hydrophobic nonwovens can cause fluid to pool on the surface of the pad, which can also result in leakage. An advantage of using apertured films as topsheets for absorbent articles is that they provide a relatively clean and dry surface as exudates passes through the film layer and into the interior of the pad. A drawback of such film-based topsheets is that they do not provide the degree of softness and comfort that a nonwoven topsheet provides.

In use as an absorbent article, the structure of the polymeric netting according to the present disclosure, with its polymeric ribbons separated from each other by polymeric strands that are significantly shorter, creates a plurality of air flow channels along the lengths of the polymeric ribbons and that allow air to circulate between the absorbent and the skin of the wearer even while the first edges of the polymeric ribbons, distal from the absorbent, are in contact with the skin of the wearer. These channels, which are absent from conventional topsheet materials, can provide a feeling of dryness and comfort. The first edges of the polymeric ribbons, which extend above the height of the polymeric strands, are free to flex and bend in response to any lateral forces exerted on them (e.g., through movement of the user). The flexibility of the polymeric ribbons adds to a feeling of softness against the user's skin. It is also believed that the ability of the polymeric ribbons to bend allows them to provide a cleansing action when the absorbent article is shifted slightly in its position relative to the user's skin. When the first edges of the polymeric ribbons contact the user's skin, small movements of the user (e.g., walking) can cause the polymeric ribbons to bend which may allow the polymeric ribbons to come into contact with a drop of liquid on a user's skin and draw it down to contact the absorbent. In this way, the polymeric ribbons serve as miniature squeegees for removing liquid from the skin.

Also, as shown in Table 1 in the Examples below, the structure of the polymeric netting according to one or more embodiments of the present disclosure, with its polymeric ribbons separated from each other by polymeric strands that are significantly shorter, allows fluid to be distributed in an absorbent article in the longitudinal direction to a much greater extent than in a conventional pad. Better distribution of fluid can prevent leakage in an absorbent article.

With the polymeric nettings according to the present disclosure and/or made according to a method disclosed herein, it may be useful to have the polymeric ribbons spread apart from one another to a greater extent in one portion of the absorbent article than in the other (e.g., using the methods described herein.) Attaching the spread polymeric netting to the absorbent or another layer of the article is useful for holding the web in this spread open condition. Spreading in certain locations allows the performance of the polymeric netting to be tailored to provide, for example, a different uptake rate and other performance characteristics near the lateral centerline of the article than near the lateral edges of the article. However, in some embodiments it may be desired to spread the web in the cross direction uniformly across the entire width of the polymeric netting.

The polymeric compositions selected for the polymeric ribbons and polymeric strands when the polymeric netting is used in an absorbent article may be hydrophobic or hydrophilic as desired. Additional material modifiers (e.g. surfactants) can be added to at least one of the polymeric ribbons or polymeric strands to change their hydrophilicity or tailor how a liquid interacts with the polymeric netting. For example, the polymeric ribbons may be made relatively hydrophilic for quicker fluid penetration through the polymeric netting while the polymeric strands may be made hydrophobic to minimize rewet. Or various constructions of the polymeric netting such as those shown in FIGS. 6 and 8 can be useful for tailoring the hydrophilicity of the polymeric netting. For example, in FIG. 6, if polymeric netting 70 is positioned on an absorbent such that polymeric ribbons 71 are extending away from the absorbent and polymeric ribbons 81 are in contact with the absorbent, polymeric ribbons 71 may be made hydrophilic to draw fluid into the absorbent, and polymeric ribbons 81 may be made hydrophobic to minimize rewet. In FIG. 8, if polymeric netting 90 is positioned on an absorbent such that the second portions of the polymeric ribbons and polymeric strands 91*b* and 93*b* are in contact with the absorbent, the first portions 91*a* of at least the polymeric ribbons may be made hydrophilic to draw fluid into the absorbent, and at least one of the second portions 91*b*, 93*b* of the polymeric ribbons or polymeric strands may be made hydrophobic to minimize rewet. In some embodiments, it may also be desirable to have the opposite pattern of hydrophilicity, for example, in which the polymeric ribbons or portions thereof that extend away from the absorbent and toward the skin are more hydrophobic than the polymeric ribbons, strands, or portions thereof positioned on the absorbent. Variations of these techniques may be useful to provide gradients of hydrophilicity in the polymeric netting. These gradients of hydrophilicity and hydrophobicity may also be useful in other applications for the polymeric nettings described herein, for example, that do not include an absorbent.

Polymeric netting according to the present disclosure may also be useful, for example, as part of a cleaning device, such as a wipe or a sponge. The cleansing action provided by the polymeric ribbons described herein in connection with absorbent articles may also make polymeric nettings disclosed herein useful for cleaning hard surfaces. Cleaning sheets can in many circumstances be too flat over the surface being cleaned and therefore only the leading edge of the cleaning sheet will load with material. A variety of techniques have been disclosed to raise portions of the cleaning sheet or to have recessed portions of the cleaning sheet to more effectively get dirt, dust and debris to capture and retain across the working surface. See, e.g., U.S. Pat. No. 7,757,334 to Patel et al. and U.S. Patent Publication Nos. 2007-0136967 to Tochacek et al. and 2009-0144923 to Tuman et al. It is believed that the first edges of the polymeric ribbons can be useful at the working surface of a cleaning wipe or sponge to scoop up debris during use, and the channels in the polymeric netting structure can help deliver the debris to a retaining surface within the wipe or sponge.

Figure 29:
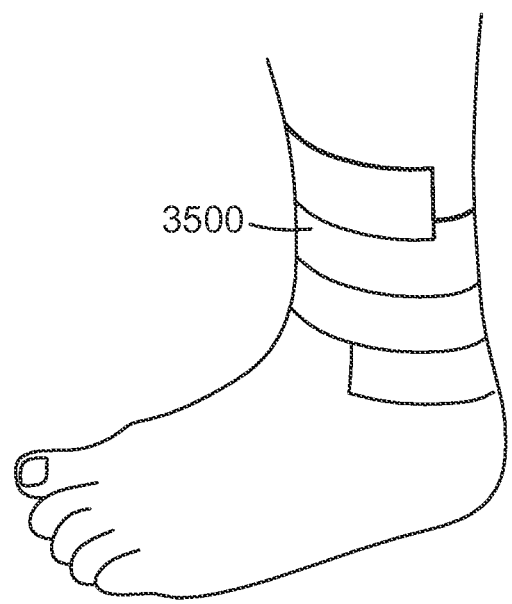
FIG. 29 is a perspective view of a foot showing an embodiment of the polymeric netting according to the present disclosure used as a wrap.

Polymeric nettings according to the present disclosure are also useful, for example, as elastic wraps. Such wraps can be useful, for example, in medical and athletic applications. For example, a polymeric netting according to the present disclosure can be useful in compression therapy, in which the application of external pressure to vascular elements increases interstitial pressure. The resulting improvement in venous return and alleviation of various symptoms (e.g., venous ulcerations and edema) makes compression therapy a useful treatment in venous and lymphatic disease, for example. Polymeric netting according to the present disclosure in use as a wrap 3500 is illustrated in FIG. 29. The net structure of wrap 3500 allows for two-way stretching and high breathability. The wrap may be secured using any conventional fastener (e.g., adhesive or mechanical fasteners).

Polymeric nettings useful as wraps may have any of the configurations shown in FIGS. 1 to 8. In use as a wrap, when the polymeric ribbons in the polymeric nettings disclosed herein in any of their embodiments are positioned in contact with the wearer's skin, the portions of the polymeric ribbons that extend above the height of the polymeric strands are free to flex and bend in response to any lateral forces exerted on the tops of these ribbons. In other words, the polymeric ribbons ends of the polymeric ribbons are free to bend over the polymeric strands. Because of this movement, it is believed that micromuscular movements during wear are more comfortable than with the elastic wraps that do not have this deflection behavior. The deflection of the polymeric ribbons makes the compression wrap feel soft and spongy to the touch.

Furthermore, when the polymeric nettings disclosed herein in any of their embodiments are used as wraps, the polymeric ribbons on one major surface of the netting may be interleaved with polymeric ribbons on the opposite surface of the polymeric netting when the polymeric netting is in a wrapped configuration. Depending on the materials that are used in the netting, these interleaved ribbons may exhibit adhesion to each other and may assist with the fastening of the wrap around the wearer. The constructions of FIGS. 5 and 6 (e.g., Examples 2 to 4) may exhibit this behavior, for example.

In embodiments in which the polymeric ribbons and polymeric strands are different colors, polymeric nettings useful as wraps, for example, can have unique aesthetic appeal. For example, FIG. 29 is a perspective view of a foot showing an embodiment of the polymeric netting according to the present disclosure used as a wrap. Using different colors in the polymeric ribbons from the polymeric strands can result in an iridescence in which the color of the wrap appears to be different depending upon the angle of viewing. Thus, in one or more embodiments, polymeric nettings according to the present disclosure useful as wraps have polymeric ribbons that are a different color from the polymeric strands. When different polymeric ribbons 31 and 41 or 71 and 81 shown in FIGS. 3 and 6, for example, are present in the polymeric netting, it may be useful for the different polymeric ribbons to be different colors.

In the embodiment shown in FIG. 6, for example, three different colors of polymer may be used to make polymeric ribbons 71, polymeric strands 73, and polymeric ribbons 81. When the polymeric ribbons 71 are viewed at an angle, the polymeric netting 70 may appear to be predominantly the color of ribbons 71. When the polymeric ribbons 81 are viewed at an angle, the polymeric netting 70 may appear to be predominantly the color of ribbons 81, and when the polymeric netting is viewed straight on (e.g., as in the configuration schematically shown in FIG. 6) all three colors may be visible.

In some applications, the polymeric netting according to the present disclosure and/or made according to a method disclosed herein can be used, for example, to provide spacers between filtering layers for filtration packs and/or to provide rigidity and support for filtration media. In some embodiments, several layers of the polymeric netting are used, where each layer is positioned to provide optimal filtering. Also, in some embodiments, the elastic feature of some polymeric nettings disclosed herein can accommodate expansion of the filter as the filter fills up.

In addition to the applications described above, polymeric nettings according to the present disclosure and/or made according to the methods disclosed herein may be useful in a variety of other applications, including harness straps and face seals for respirators, as a surface layer for surgical drapes and gowns, cast padding, tapes (including for medical applications), pest control articles (e.g., mosquito nettings), geotextile applications (e.g., erosion control textiles), water/vapor management in clothing, reinforcement for nonwoven articles (e.g., paper towels), self-bulking articles (e.g., for packaging) where the polymeric netting thickness is increased by stretching polymeric nettings with polymeric ribbons and polymeric strands having very different moduli or elasticities, floor coverings (e.g., rugs and temporary mats), grip supports (e.g., for tools and athletic articles), and pattern-coated adhesives.

In one or more embodiments, the polymeric netting according to and/or made according to the present disclosure is joined to a carrier for ease of handling or for making a laminate for a selected application. The polymeric netting may be joined to a carrier, for example, by lamination (e.g., extrusion lamination), adhesives (e.g., pressure sensitive adhesives), or other bonding techniques (e.g., ultrasonic bonding, compression bonding, or surface bonding).

The carrier may be continuous (i.e., without any through-penetrating holes) or discontinuous (e.g. comprising through-penetrating perforations or pores). The carrier may include a variety of suitable materials including woven webs, non-woven webs (e.g., spunbond webs, spunlaced webs, airlaid webs, meltblown web, and bonded carded webs), textiles, plastic films (e.g., single- or multilayered films, coextruded films, laterally laminated films, or films including foam layers), and combinations thereof. In some embodiments, the carrier is a fibrous material (e.g., a woven, nonwoven, or knit material). Examples of materials for forming thermoplastic films or thermoplastic fibers for a fibrous carrier include polyolefins (e.g., polyethylene, polypropylene, polybutylene, ethylene copolymers, propylene copolymers, butylene copolymers, and copolymers and blends of these polymers), polyesters, and polyamides. The fibers may also be multi-component fibers, for example, having a core of one thermoplastic material and a sheath of another thermoplastic material. In some embodiments, the carrier includes multiple layers of nonwoven materials with, for example, at least one layer of a meltblown nonwoven and at least one layer of a spunbonded nonwoven, or any other suitable combination of nonwoven materials. For example, the carrier may be a spunbond-meltbond-spunbond, spunbond-spunbond, or spunbond-spunbond-spunbond multilayer material. Or, the carrier may be a composite web including a nonwoven layer and a dense film layer. Useful carriers may have any suitable basis weight or thickness that is desired for a particular application. For a fibrous carrier, the basis weight may range, e.g., from at least about 5, 8, 10, 20, 30, or 40 grams per square meter, up to about 400, 200, or 100 grams per square meter. The carrier may be up to about 5 mm, about 2 mm, or about 1 mm in thickness and/or at least about 0.1, about 0.2, or about 0.5 mm in thickness.

In one or more embodiments where the polymeric netting is made from a thermoplastic, the thermoplastic can be joined to a fibrous web carrier using surface bonding or loft-retaining bonding techniques. The term "surface-bonded" when referring to the bonding of fibrous materials means that parts of fiber surfaces of at least portions of fibers are melt-bonded to at least a portion of the polymeric netting, in such a manner as to substantially preserve the original (pre-bonded) shape of the polymeric netting, and to substantially preserve at least some portions of the polymeric netting in an exposed condition, in the surface-bonded area. Quantitatively, surface-bonded fibers may be distinguished from embedded fibers in that at least about 65% of the surface area of the surface-bonded fiber is visible above the polymeric netting in the bonded portion of the fiber. Inspection from more than one angle may be necessary to visualize the entirety of the surface area of the fiber. The term "loft-retaining bond" when referring to the bonding of fibrous materials means a bonded fibrous material includes a loft that is at least 80% of the loft exhibited by the material prior to, or in the absence of, the bonding process. The loft of a fibrous material as used herein is the ratio of the total volume occupied by the web (including fibers as well as interstitial spaces of the material that are not occupied by fibers) to the volume occupied by the material of the fibers alone. If only a portion of a fibrous web has the polymeric netting bonded thereto, the retained loft can be easily ascertained by comparing the loft of the fibrous web in the bonded area to that of the web in an unbonded area. It may be convenient in some circumstances to compare the loft of the bonded web to that of a sample of the same web before being bonded, for example, if the entirety of fibrous web has the polymeric netting bonded thereto. In some of these embodiments, the joining includes impinging heated gaseous fluid (e.g., ambient air, dehumidified air, nitrogen, an inert gas, or other gas mixture) onto a first surface of the fibrous web carrier while it is moving; impinging heated fluid onto a major surface of the polymeric netting while the continuous web is moving; and contacting the first surface of the fibrous web with the polymeric netting so that the first surface of the fibrous web is melt-bonded (e.g., surface-bonded or bonded with a loft-retaining bond) to the polymeric netting. Impinging heated gaseous fluid onto the first surface of the fibrous web and impinging heated gaseous fluid on a major surface of the polymeric netting may be carried out sequentially or simultaneously. Further methods and apparatuses for joining a continuous web to a fibrous carrier web using heated gaseous fluid may be found in U.S. Patent Publication Nos. 2011/0151171 and 2011/0147475 to Biegler et al.

In one or more embodiments where the polymeric netting is joined to a carrier, one or more zones of the carrier may include one or more elastically extensible materials extending in at least one direction when a force is applied and returning to approximately their original dimension after the force is removed. In some embodiments, at least the portion of the carrier joined to the multiple strands of the backing or loop material is not stretchable. In some embodiments, the portion of carrier joined to the multiple strands will have up to a 10 (in some embodiments, up to 9, 8, 7, 6, or 5) percent elongation in the CD. In some embodiments, such constructions may be subjected to mechanical activation (e.g., ring rolling) to render them elastomeric. In some embodiments, the carrier may be extensible but nonelastic. In other words, the carrier may have an elongation of at least 5, 10, 15, 20, 25, 30, 40, or 50 percent but substantially no recovery from the elongation (e.g., up to 10 or 5 percent recovery). Suitable extensible carriers may include nonwovens (e.g., spunbond, spunbond meltblown spunbond, or carded nonwovens). In some embodiments, the nonwoven may be a high elongation carded nonwoven (e.g., HEC). In some embodiments, the carrier is not pleated.

Respirators

Figure 36:
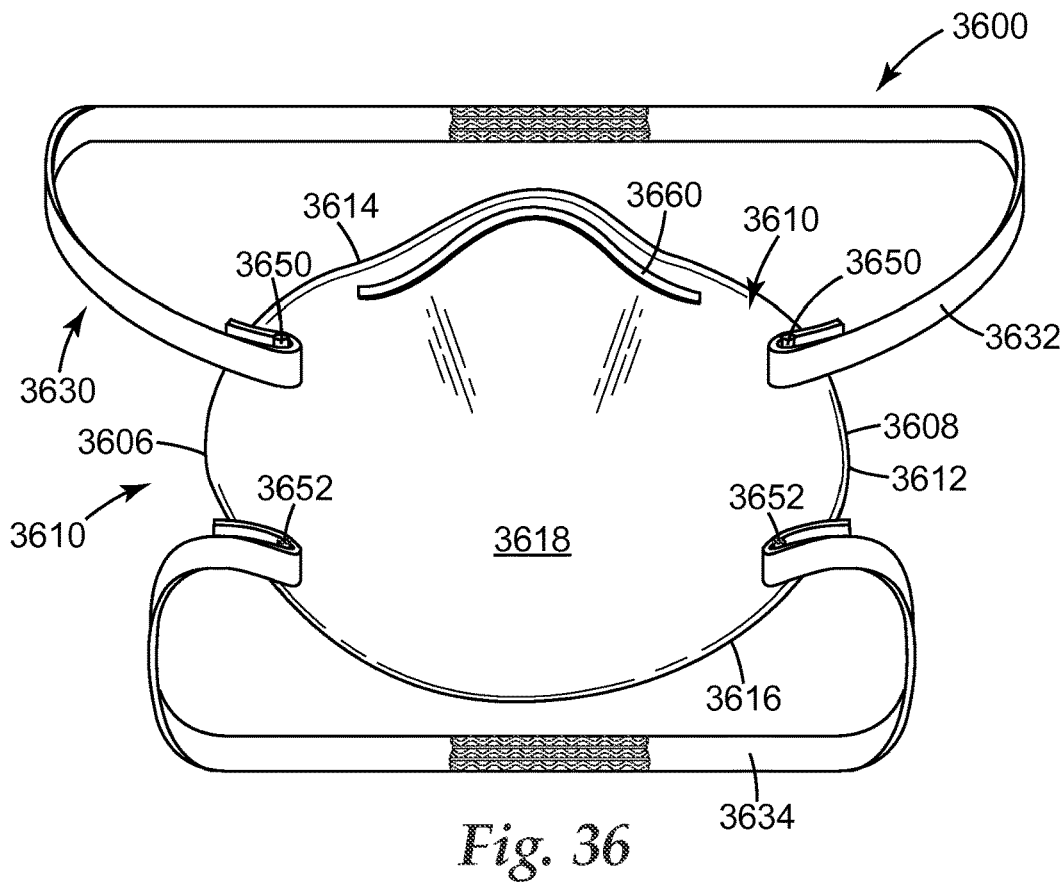
FIG. 36 is a schematic front view of one embodiment of a respirator.

As mentioned herein, the various embodiments of polymeric nettings of the present disclosure can be utilized in many different applications. For example, in one or more embodiments, a polymeric netting can be utilized with a respirator. For example, FIG. 36 is a schematic front view of a respirator 3600. The respirator 3600 can include any suitable respirator, e.g., a filtering face-piece respirator. Further, in one or more embodiments, the respirator 3600 can be a preformed respirator or a flat fold respirator as is further described herein.

The respirator 3600 can include a mask body 3610 and a harness 3630. The mask body 3610 can include an exterior surface 3618 and an interior surface (e.g., interior surface 3719 of respirator 3700 of FIG. 37). The mask body 3610 can also include a perimeter 3612 that includes an upper perimeter segment 3614 and a lower perimeter segment 3616.

The mask body 3610 may be of a curved, hemispherical, cup-shape such as shown in FIG. 36. See also U.S. Pat. No. 4,536,440 to Berg and U.S. Pat. No. 4,807,619 to Dyrud et al. The mask body 3610 also may take on other shapes as so desired. For example, the mask body 3610 can be a cup-shaped mask having a construction as shown in U.S. Pat. No. 4,827,924 to Japuntich. The mask body 3610 also may be a part of a flat-folded respirator such as disclosed in U.S. Pat. Nos. 6,722,366 and 6,715,489 to Bostock; D459,471 and D458,364 to Curran et al.; D448,472 and D443,927 to Chen; and U.S. Patent Publication No. 2008/0271737 to Facer et al. See also U.S. Pat. Nos. 4,419,993; 4,419,994; 4,300,549; 4,802,473; and Re. 28,102.

The harness 3630 can include one or more straps 3632, 3634 that, in one or more embodiments, can be joined to the mask body 3610 on opposing sides of the mask body at attachment points 3650 and 3652.

The one or more straps 3632, 3634 can be made of any suitable material or combination of materials. For example, in one or more embodiments, the one or more straps 3632, 3634 can include a polymeric netting. Straps can include any suitable polymeric netting described herein, e.g., polymeric netting 10 of FIG. 1. For example, in reference to netting 10 of FIG. 1, the polymeric netting can include polymeric ribbons 1 and polymeric strands 3. Each of the polymeric ribbons and strands 1, 3 have a length (not shown in FIG. 1 but would extend into the plane of the figure), width (e.g., width w1 of ribbons 1 and width w3 of strands 3), and height (e.g., height h1 of ribbons 1 and h3 of strands 3), where the length is the longest dimension, the width is the shortest dimension, and the height is the dimension transverse to the length and the width.

The polymeric ribbons 1 of the polymeric netting 10 can include any suitable height to width aspect ratio described herein. For example, in one or more embodiments, one or more of the polymeric ribbons 1 can include a height to width aspect ratio of at least 5 to 1. Further, the polymeric ribbons 1 can be bonded to the polymeric strands 1 in any suitable location. In one or more embodiments, a major surface 2 of one or more polymeric ribbons 1 can be intermittently bonded to only one polymeric strand 3. And one or more ribbons 1 of the polymeric netting 10 can have a height that is at least 2 times greater than a height of one or more polymeric strands 3 as is further described herein.

The straps 3632, 3634 of the harness 3630 can have any suitable thickness. In one or more embodiments, one or both of straps 3632, 3634 can have a thickness of no greater than 5 mm. In one or more embodiments, one or both of the straps 3632, 3634 can have a thickness of no greater than 2 mm. In general, the polymeric ribbons 1 of the polymeric netting 10 can provide a thickness to the straps 3632, 3634 such that in one or more embodiments the straps may be easier to grasp, e.g., by a user wearing gloves. In one or more embodiments, a thickness of the straps 3632, 3634 can be increased without substantially increasing the amount of material used to manufacture the straps; therefore, a high thickness, low basis weight strap can be fabricated that is thicker and yet can also have a moderate retraction force.

Further, in one or more embodiments, the straps 3632, 3634 can have any suitable width. For example, in one or more embodiments, the width of one or both of the straps can be at least 1/32 inches. In one or more embodiments, the width of one or both of the straps can be no greater than 1 inch.

The straps 3632, 3634 engage the mask body 3610 on first and second sides 3606, 3608, respectively, of the mask body 3610 at attachment points 3650 and 3652. The straps 3632, 3634 may engage the mask body directly by being secured thereto through use of staples or other suitable mechanical fasteners. Alternatively, the straps 3632, 3634 can be physically or chemically secured to the mask body 3610 through use of bonds, including welds or adhesive attachment. Ultrasonic welding may be used, for example, to secure the straps to the mask body 3610. When the straps 3632, 3634 are welded to the mask body 3610, the polymeric netting in the straps can melt to form solid non-porous plastic that mates with the polymeric material that includes the mask body. Typically the polymeric material in the ribbons and/or strands of the polymeric netting melts into or merges with the polymeric material in the fibers of the layer(s) that are included in the mask body.

The mask body 3610 also may have a nose clip 3660 secured thereto, which allows the wearer to conform the mask body to the wearer's nose in a sinus region 3604. If desired, an exhalation valve (not shown) may be secured to the mask body 3610 to assist in the rapid displacement or purging of exhaled air from the interior gas space. The exhalation valve is commonly attached to the mask body 3610 at a central location. When the respirator 3600 is a filtering face-piece respirator like the respirator illustrated in FIG. 36, the mask body 3610 may include a filtering structure that includes one or more layers of filter media, shaping layers, and/or cover webs, e.g., filtering structure 4070 illustrated in FIG. 40 and further described herein. A respirator having this construction may be assembled as described U.S. Pat. No. 7,131,442 to Kronzer et al.

The first and second straps 3632, 3634 of the harness 3630 can include any suitable polymeric netting described herein. In one or more embodiments, the straps 3632, 3634 can include one, two, three, or more layers of polymeric netting. For example, one or both of the straps 3632, 3634 can include first and second layers of polymeric netting material juxtaposed in an adjoining fashion. The layers can be combined together in the die as a melt. The layers generally may have some natural affinity to each other, such that the intermixing and bonding between materials at the interface during the melt state holds the layers together. The two flow streams of the two layers may meet together inside the die and exit as a two-layered stranded product. Thus, the first and second layers of the netting can be secured directly to each other. Alternatively, other layer(s) may be inserted between the two layers so that they are disposed therebetween in the final product. The first netting layer can be provided with a first color that is different from the color of the second netting layer. The use of different colors can add an aesthetic effect to the strap and may also allow the user to more easily detect if the strap is in a twisted condition. As shown, the netting layers can be secured to one another such that the array of polymeric strands in each of the layers corresponds to one another when viewed from a plane projected onto a major surface of the strap. The straps 3632, 3634 can be constructed to be sufficiently porous such that the straps are air permeable from a first major surface to a second major surface. The straps 3632, 3634 can have a series of openings or spaces between the ribbons and strands (e.g., ribbons 1 and strands 3 of polymeric netting 10 of FIG. 1) through which air can pass.

Figure 40:
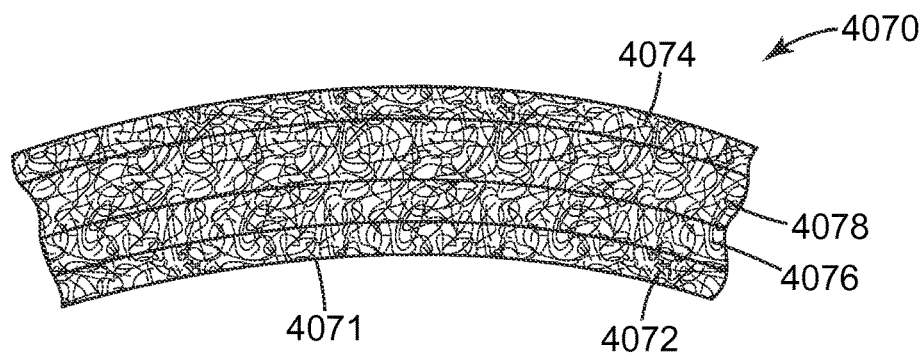
FIG. 40 is a schematic cross-section view of one embodiment of a filtering structure of a respirator.

The filtering structure that is used in connection with respirators suitable for use in connection with the present disclosure may take on a variety of different shapes and configurations. As shown in FIG. 40, the filtering structure 4070 may have a plurality of layers, including a fibrous filtration layer 4078 and one or more fibrous cover webs 4072, 4074. When the respirator is a molded mask, the mask body may also include a shaping layer 4076. See, e.g., U.S. Pat. No. 6,923,182 to Angadjivand et al.; U.S. Pat. No. 7,131,442 to Kronzer et al.; U.S. Pat. Nos. 6,923,182 and 6,041,782 to Angadjivand et al.; U.S. Pat. No. 4,807,619 to Dyrud et al.; and U.S. Pat. No. 4,536,440 to Berg. The filtering structure removes contaminants from the ambient air and may also act as a barrier layer that precludes liquid splashes from entering the mask interior. The outer cover web can act to stop or slow any liquid splashes, and the inner filtering structure may then contain them if there is penetration past the other layers. The filtering structure can be of a particle capture or gas and vapor type filter. The filtering structure may include multiple layers of similar or dissimilar filter media and one or more cover webs as the application requires. If the respirator contains a fluid impermeable mask body that has one or more filter cartridges attached to it. See, e.g., U.S. Pat. No. 6,874,499 to Viner et al.; U.S. Pat. No. 6,277,178 and D613,850 to Holmquist-Brown et al.; RE39, 493 to Yuschak et al.; D652,507, D471,627, and D467,656 to Mittelstadt et al.; and D518,571 to Martin. The filtering structure may be disposed within the filtering cartridge. Filtering structures located in filter cartridges do not need shaping layers to support them.

FIG. 40 shows the filtering structure 4070 in cross-section. The filtering structure 4070 may include one or more cover webs 4072 and 4074, a shaping layer 4076, and a filtration layer 4078. The cover webs 4072, 4074 may be located on the outer sides of the filtering structure 4078 to capture any fibers that could come loose therefrom. Typically, the cover webs 4072, 4074 are made from a selection of fibers that provide a comfortable feel, particularly on the side 4071 of the filtering structure 4070 that makes contact with the wearer's face. The constructions of various filter layers, shaping layers, and cover webs that may be used in conjunction with a filtering structure used in a respirator of the present disclosure are described herein in more detail.

Filtration Layer

Filters that may be beneficially employed in a respirator of the present disclosure are generally low in pressure drop (for example, less than about 195 to 295 Pascals at a face velocity of 13.8 centimeters per second) to minimize the breathing work of the mask wearer. Filtration layers additionally are flexible and have sufficient shear strength so that they generally retain their structure under the expected use conditions. Examples of particle capture filters include one or more webs of fine inorganic fibers (such as fiberglass) or polymeric synthetic fibers. Synthetic fiber webs may include electret-charged polymeric microfibers that are produced from processes such as meltblowing. Polyolefin microfibers formed from polypropylene that has been electrically charged provide particular utility for particulate capture applications.

The filtration layer is typically chosen to achieve a desired filtering effect. The filtration layer generally will remove a high percentage of particles and/or or other contaminants from the gaseous stream that passes through it. For fibrous filter layers, the fibers selected depend upon the kind of substance to be filtered and, typically, are chosen so that they do not become bonded together during the manufacturing operation. As indicated, the filtration layer may come in a variety of shapes and forms and typically has a thickness of about 0.2 millimeters (mm) to 1 centimeter (cm), more typically about 0.3 mm to 0.5 cm, and it could be a generally planar web or it could be corrugated to provide an expanded surface area. See, e.g., U.S. Pat. Nos. 5,804,295 and 5,656,368 to Braun et al. The filtration layer also may include multiple filtration layers joined together by an adhesive or any other techniques. Essentially any suitable material that is known (or later developed) for forming a filtering layer may be used as the filtering material. Webs of melt-blown fibers, such as those taught in Wente, Van A., *Superfine Thermoplastic Fibers*, 48 Indus. Engn. Chem., 1342 et seq. (1956), especially when in a persistent electrically charged (electret) form are especially useful (see, e.g., U.S. Pat. No. 4,215,682 to Kubik et al.). These melt-blown fibers may be microfibers that have an effective fiber diameter less than about 20 micrometers (μm) (referred to as BMF for "blown microfiber"), typically about 1 to 12 μm. Effective fiber diameter may be determined according to Davies, C. N., *The Separation Of Airborne Dust Particles*, Institution Of Mechanical Engineers, London, Proceedings 1B, 1952. Particularly preferred are BMF webs that contain fibers formed from polypropylene, poly(4-methyl-1-pentene), and combinations thereof. Electrically charged fibrillated-film fibers as taught in U.S. Patent Re. 31,285 to van Turnhout also may be suitable, as well as rosin-wool fibrous webs and webs of glass fibers or solution-blown, or electrostatically sprayed fibers, especially in microfiber form. Electric charge can be imparted to the fibers by contacting the fibers with water as disclosed in U.S. Pat. No. 6,824,718 to Eitzman et al.; U.S. Pat. No. 6,783,574 to Angadjivand et al.; U.S. Pat. No. 6,743,464 to Insley et al.; U.S. Pat. Nos. 6,454,986 and 6,406,657 to Eitzman et al.; and U.S. Pat. Nos. 6,375,886 and 5,496,507 to Angadjivand et al. Electric charge also may be imparted to the fibers by corona charging as disclosed in U.S. Pat. No. 4,588,537 to Klasse et al., or by tribocharging as disclosed in U.S. Pat. No. 4,798,850 to Brown. Also, additives can be included in the fibers to enhance the filtration performance of webs produced through the hydrocharging process (see U.S. Pat. No. 5,908,598 to Rousseau et al.). Fluorine atoms, in particular, can be disposed at the surface of the fibers in the filter layer to improve filtration performance in an oily mist environment. See, e.g., U.S. Pat. Nos. 6,398,847 B1, 6,397,458 B1, and 6,409,806 B1 to Jones et al. Typical basis weights for electret BMF filtration layers are about 10 to 100 grams per square meter ($g/m^2$). When electrically charged according to techniques described in, e.g., the '507 Angadjivand et al. Patent, and when including fluorine atoms as mentioned in the Jones et al. Patents, the basis weight may be about 20 to 40 $g/m^2$ and about 10 to 30 $g/m^2$, respectively. Additionally, sorptive materials such as activated carbon may be disposed between the fibers and/or various layers that include the filtering structure. Further, separate particulate filtration layers may be used in conjunction with sorptive layers to provide filtration for both particulates and vapors. The sorbent component may be used for removing hazardous or odorous gases from the breathing air. Sorbents may include powders or granules that are bound in a filter layer by adhesives, binders, or fibrous structures. See, e.g., U.S. Pat. No. 6,334,671 to Springett et al. and U.S. Pat. No. 3,971,373 to Braun. A sorbent layer can be formed by coating a substrate, such as fibrous or reticulated foam, to form a thin coherent layer. Sorbent materials may include activated carbons that are chemically treated or not, porous alumna-silica catalyst substrates, and alumna particles. An example of a sorptive filtration structure that may be conformed into various configurations is described in U.S. Pat. No. 6,391,429 to Senkus et al.

Cover Web(s)

The cover webs also may have filtering abilities, although typically not nearly as good as the filtering layer and/or may serve to make a filtering face-piece respirator more comfortable to wear. The cover webs may be made from non-woven fibrous materials such as spun bonded fibers that contain, e.g., polyolefins, and polyesters. See, e.g., U.S. Pat. No. 6,041,782 to Angadjivand et al.; U.S. Pat. No. 4,807,619 to Dyrud et al.; and U.S. Pat. No. 4,536,440 to Berg. When a wearer inhales, air is drawn through the mask body, and airborne particles become trapped in the interstices between the fibers, particularly the fibers in the filter layer.

The inner cover web can be used to provide a smooth surface for contacting the wearer's face. Further, the outer cover web, in addition to providing splash fluid protection, can be used for entrapping loose fibers in the mask body and for aesthetic reasons. The cover web typically does not provide any substantial filtering benefits to the filtering structure, although it can act as a pre-filter when disposed on the exterior of (or upstream to) the filtration layer. To obtain a suitable degree of comfort, an inner cover web can have a comparatively low basis weight and can be formed from comparatively fine fibers. More particularly, the cover web may be fashioned to have a basis weight of about 5 to 50 $g/m^2$ (typically 10 to 30 $g/m^2$), and the fibers may be less than 3.5 denier (typically less than 2 denier, and more typically less than 1 denier but greater than 0.1 denier). Fibers used in the cover web often have an average fiber diameter of about 5 to 24 micrometers, typically of about 7 to 18 micrometers, and more typically of about 8 to 12 micrometers. The cover web material may have a degree of elasticity (typically, but not necessarily, 100 to 200% at break) and may be plastically deformable.

Suitable materials for the cover web may be blown microfiber (BMF) materials, particularly polyolefin BMF materials, e.g., polypropylene BMF materials (including polypropylene blends and also blends of polypropylene and polyethylene). And exemplary process for producing BMF materials for a cover web is described in U.S. Pat. No. 4,013,816 to Sabee et al. The web may be formed by collecting the fibers on a smooth surface, typically a smooth-surfaced drum or a rotating collector. See, e.g., U.S. Pat. No. 6,492,286 to Berrigan et al. Spun-bond fibers also may be used.

A typical cover web may be made from polypropylene or a polypropylene/polyolefin blend that contains 50 weight percent or more polypropylene. These materials have been found to offer high degrees of softness and comfort to the wearer and also, when the filter material is a polypropylene BMF material, to remain secured to the filter material without requiring an adhesive between the layers. Polyolefin materials that are suitable for use in a cover web may include, for example, a single polypropylene, blends of two polypropylenes, and blends of polypropylene and polyethylene, blends of polypropylene and poly(4-methyl-1-pentene), and/or blends of polypropylene and polybutylene. One example of a fiber for the cover web is a polypropylene BMF made from the polypropylene resin "Escorene 3505G" from Exxon Corporation, providing a basis weight of about 25 g/m² and having a fiber denier in the range 0.2 to 3.1 (with an average, measured over 100 fibers of about 0.8). Another suitable fiber is a polypropylene/polyethylene BMF (produced from a mixture comprising 85 percent of the resin "Escorene 3505G" and 15 percent of the ethylene/alpha-olefin copolymer "Exact 4023" also from Exxon Corporation) providing a basis weight of about 25 g/m² and having an average fiber denier of about 0.8. Suitable spunbond materials are available under the trade designations "Corosoft Plus 20," "Corosoft Classic 20" and "Corovin PP S 14," from Corovin GmbH of Peine, Germany, and a carded polypropylene/viscose material available, under the trade designation "370/15," from J. W. Suominen O Y of Nakila, Finland. Cover webs typically have very few fibers protruding from the web surface after processing and therefore have a smooth outer surface. Examples of cover webs that may be used in a respirator of the present disclosure are described, e.g., in U.S. Pat. No. 6,041,782 to Angadjivand; U.S. Pat. No. 6,123,077 to Bostock et al.; and PCT Publication No. WO 96/28216A to Bostock et al.

In one or more embodiments, one or both of the inner cover web and outer cover web can include a polymeric netting. Any suitable polymeric netting described herein can be utilized for one or both cover webs. The netting may be made from a variety of polymeric materials. Polymers suitable for netting formation are thermoplastic materials. Examples of thermoplastic polymers that can be used to form polymer netting of the present invention include polyolefins (e.g., polypropylene and polyethylene), polyethylene-vinyl acetate (EVA), polyvinyl chloride, polystyrene, nylons, polyesters (e.g., polyethylene terephthalate), and elastomeric polymers, (e.g., ABA block copolymers, polyurethanes, polyolefin elastomers, polyurethane elastomers, metallocene polyolefin elastomers, polyamide elastomers, ethylene vinyl acetate elastomers, and polyester elastomers). Blends of two or more materials also may be used in the manufacture of nettings. Examples of such blends include polypropylene/EVA and polyethylene/EVA. Polypropylene may be preferred for use in the polymeric netting since melt-blown fibers are regularly made from polypropylene. Use of similar polymers enables proper welding of the support structure to the filtering structure.

Shaping Layer

The shaping layer(s) may be formed from at least one layer of fibrous material that can be molded to the desired shape with the use of heat and that retains its shape when cooled. Shape retention is typically achieved by causing the fibers to bond to each other at points of contact between them, for example, by fusion or welding. Any suitable material known for making a shape-retaining layer of a direct-molded respiratory mask may be used to form the mask shell, including, for example, a mixture of synthetic staple fiber, e.g., crimped, and bicomponent staple fiber. Bicomponent fiber is a fiber that includes two or more distinct regions of fibrous material, typically distinct regions of polymeric materials. Typical bicomponent fibers include a binder component and a structural component. The binder component allows the fibers of the shape-retaining shell to be bonded together at fiber intersection points when heated and cooled. During heating, the binder component flows into contact with adjacent fibers. The shape-retaining layer can be prepared from fiber mixtures that include staple fiber and bicomponent fiber in a weight-percent ratios that may range, for example, from 0/100 to 75/25. In one or more embodiments, the material includes at least 50 weight-percent bicomponent fiber to create a greater number of intersection bonding points, which, in turn, increase the resilience and shape retention of the shell.

Suitable bicomponent fibers that may be used in the shaping layer include, for example, side-by-side configurations, concentric sheath-core configurations, and elliptical sheath-core configurations. One suitable bicomponent fiber is the polyester bicomponent fiber available, under the trade designation "KOSA T254" (12 denier, length 38 mm), from Kosa of Charlotte, N.C., U.S.A., which may be used in combination with a polyester staple fiber, for example, that is available from Kosa under the trade designation "T259" (3 denier, length 38 mm) and possibly also a polyethylene terephthalate (PET) fiber, for example, that available from Kosa under the trade designation "T295" (15 denier, length 32 mm). Alternatively, the bicomponent fiber may include a generally concentric sheath-core configuration having a core of crystalline PET surrounded by a sheath of a polymer formed from isophthalate and terephthalate ester monomers. The latter polymer is heat softenable at a temperature lower than the core material. Polyester has advantages in that it can contribute to mask resiliency and can absorb less moisture than other fibers.

Alternatively, the shaping layer can be prepared without bicomponent fibers. For example, fibers of a heat-flowable polyester can be included together with, e.g., stapled, crimped, fibers in a shaping layer so that, upon heating of the web material, the binder fibers can melt and flow to a fiber intersection point where it forms a mass that upon cooling of the binder material, creates a bond at the intersection point. Staple fibers (for the shaping component) that are pre-treated with Ammonium Polyphosphate type intumescent FR agents may be used in connection with the present disclosure in addition to or in lieu of a spray-application of the agent. Having the staple fibers contain, or, otherwise being treated with, the agent and then formed into a shell (using binder fibers to hold it together) would be another pathway to employ the agents.

When a fibrous web is used as the material for the shape-retaining shell, the web can be conveniently prepared on a "Rando Webber" air-laying machine (available from Rando Machine Corporation, Macedon, N.Y.) or a carding machine. The web can be formed from bicomponent fibers or other fibers in conventional staple lengths suitable for such equipment. To obtain a shape-retaining layer that has the required resiliency and shape-retention, the layer can have a basis weight of at least about 100 g/m², although lower basis weights are possible. Higher basis weights, for example, approximately 150 or more than 200 g/m², may provide greater resistance to deformation and greater resiliency and may be more suitable if the mask body is used to support an exhalation valve. Together with these minimum basis weights, the shaping layer typically has a maximum density of about 0.2 g/cm² over the central area of the mask. Typically, the shaping layer would have a thickness of about 0.3 to 2.0, more typically about 0.4 to 0.8 millimeters. Examples of shaping layers suitable for use in the present disclosure are described, e.g., U.S. Pat. No. 5,307,796 to Kronzer et al.; U.S. Pat. No. 4,807,619 to Dyrud et al.; and U.S. Pat. No. 4,536,440 to Berg. Staple fibers (for the shaping component) that are pre-treated with Ammonium Polyphosphate type intumescent FR agents may be used in connection with the present disclosure in addition to or in lieu of a spray-application of the agent. Having the staple fibers contain, or, otherwise being treated with, the agent and then formed into a shell (using binder fibers to hold it together) would be another pathway to employ the agents.

Respirator Componentry

The strap(s) that are used in the respirator harness can be expanded to greater than twice its total length and can be returned to its relaxed state many times throughout the useful life of the respirator. The strap also could possibly be increased to three or four times its relaxed state length and can be returned to its original condition without any damage thereto when the tensile forces are removed. In one or more embodiments, the elastic limit thus is not less than two, three, or four times the relaxed-state length of the strap(s). Typically, the strap(s) are about 20 to 30 cm long, 3 to 20 mm wide, and about 0.3 to 1 mm thick. The strap(s) may extend from the first side of the respirator to the second side as a continuous strap or the strap may have a plurality of parts, which can be joined together by further fasteners or buckles. For example, the strap may have first and second parts that are joined together by a fastener that can be quickly uncoupled by the wearer when removing the mask body from the face. Alternatively, the strap may form a loop that is placed around the wearer's ears. See, e.g., U.S. Pat. No. 6,394,090 to Chen et al. Examples of fastening or clasping mechanism that may be used to joint one or more parts of the strap together is shown, e.g., in U.S. Pat. No. 6,062,221 to Brostrom et al. and U.S. Pat. No. 5,237,986 to Seppala; and in EP Patent Publication No. 1,495,785A1 to Chen. The harness also may include a reusable carriage, one or more buckles, and/or a crown member to support the respirator on a person's head. See, e.g., U.S. Pat. Nos. 6,732,733 and 6,457,473 to Brostrom et al.; and U.S. Pat. Nos. 6,591,837 and 6,715,490 to Byram. Although a filtering face-piece respirator has been illustrated in showing the present disclosure, the respirator may include a compliable rubber-type mask that has one or more filter cartridges attached to it. See, e.g., U.S. Patent Nos. RE 39,493 to Yuschak et al. and U.S. Pat. No. 7,650,884 to Flannigan et al. Or it could be a full face respirator. See, e.g., U.S. Pat. No. 8,067,110 to Rakow et al.; U.S. Pat. No. 7,594,510 to Betz et al.; and D421,118 and D378,610 to Reischel et al.

As indicated, an exhalation valve may be attached to the mask body to facilitate purging exhaled air from the interior gas space. The use of an exhalation valve may improve wearer comfort by rapidly removing the warm moist exhaled air from the mask interior. See, e.g., U.S. Pat. Nos. 7,188,622; 7,028,689, and 7,013,895 to Martin et al.; U.S. Pat. Nos. 7,428,903; 7,311,104; 7,117,868; 6,854,463; 6,843,248; and U.S. Pat. No. 5,325,892 to Japuntich et al.; U.S. Pat. Nos. 7,302,951 and 6,883,518 to Mittelstadt et al.; and RE 37,974 to Bowers. Essentially any exhalation valve that provides a suitable pressure drop and that can be properly secured to the mask body may be used in connection with the present disclosure to rapidly deliver exhaled air from the interior gas space to the exterior gas space.

A nose clip that is used with filtering face-piece respirators of the present disclosure may be essentially any additional part that assists in improving the fit over the wearer's nose. Because the wearer's face exhibits a major change in contour in the nose region, a nose clip may be used to better assist in achieving the appropriate fit in this location. The nose clip may include, for example, a pliable dead soft band of metal such as aluminum, which can be shaped to hold the mask in a desired fitting relationship over the nose of the wearer and where the nose meets the cheek. The nose clip may be linear in shape when viewed from a plane projected onto the mask body when in its folded or partially folded condition. Alternatively, the nose clip can be an M-shaped nose clip, an example of which is shown in U.S. Pat. No. 5,558,089 and Des. 412,573 to Castiglione. Other exemplary nose clips are described in U.S. patent application Ser. No. 12/238,737 (filed Sep. 26, 2008); U.S. Patent Publication No. 2007-0044803A1 (filed Aug. 25, 2005); and U.S. Patent Publication No. 2007-0068529A1 (filed Sep. 27, 2005).

Face Seal

Figure 37:
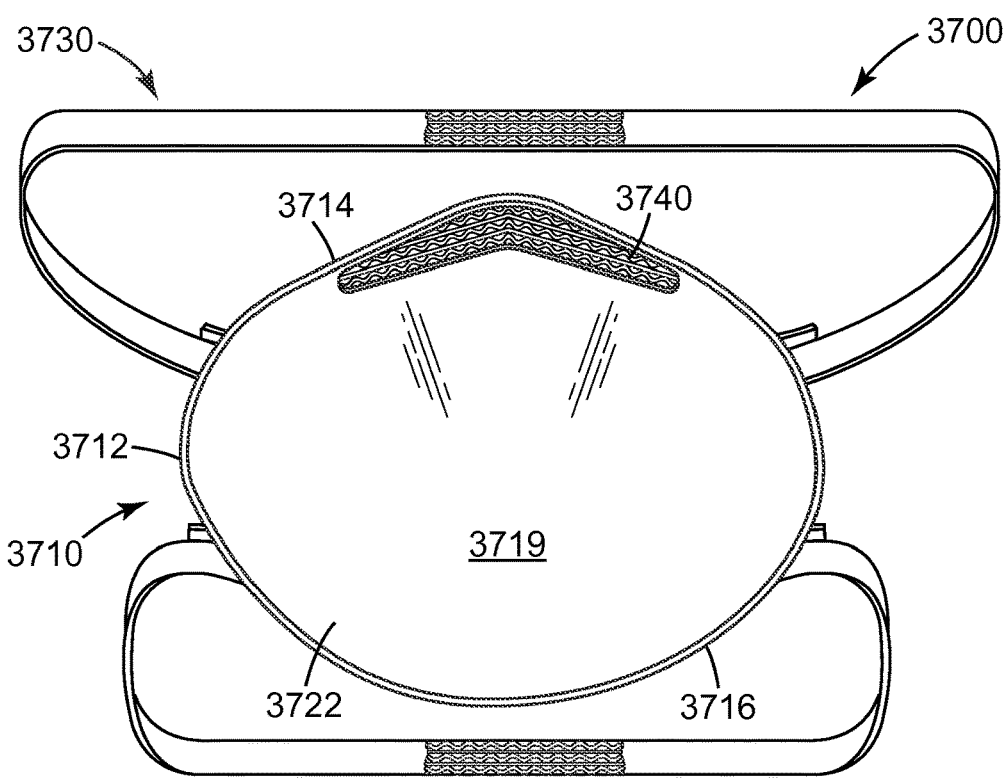
FIG. 37 is a schematic rear view of another embodiment of a respirator.

In one or more embodiments, the respirators described herein can also include a face seal. For example, FIG. 37 is a schematic rear view of an interior surface 3719 of a respirator 3700. All of the design considerations and possibilities regarding the respirator 3600 of FIG. 36 apply equally to the respirator 3700 of FIG. 37. Respirator 3700 includes a mask body 3710 and a harness 3730 attached to the mask body as is further described herein.

Respirator 3700 also includes a face seal 3740 disposed adjacent at least a portion of a perimeter 3712 of the mask body 3710. As used herein, the term "adjacent at least a portion of a perimeter" means that the face seal is disposed closer to at least a portion of the perimeter of the mask body then to a central region of the mask body. In the embodiment illustrated in FIG. 37, the face seal 3740 is disposed adjacent an upper perimeter segment 3714 of perimeter 3712. In one or more alternative embodiments, the face seal 3740 can be disposed along or adjacent a lower perimeter segment 3716. In one or more embodiments, the face seal 3740 can be disposed adjacent any portion of the perimeter 3712 of mask body 3710. In one or more embodiments, the face seal 3740 can be disposed adjacent the entire perimeter 3712 of the mask body 3710 as is further described herein.

The face seal 3740 can be any suitable size or dimension and take any suitable shape. In the embodiment illustrated in FIG. 37, the face seal 3740 has taken an elongated shape that extends along the upper perimeter segment 3714 and follows a shape or curve of the upper perimeter segment. In one or more alternative embodiments, the face seal 3740 can take a wedge shape as is further described herein.

The face seal 3740 is configured to contact a face of a wearer and provide a seal between the face and the mask body 3710 of the respirator 3700. The face seal 3740 can be configured to contact any portion of a face of a wearer. For example, in the embodiment illustrated in FIG. 37, the face seal 3740 is configured to contact a sinus region of a face of a wearer. In one or more embodiments, the face seal 3740 can provide a seal between the mask body 3710 and the nose of a wearer.

The face seal 3740 can include any suitable material or combination of materials. In one or more embodiments, the face seal 3740 includes a polymeric netting. Any suitable polymeric netting described herein can be utilized for the face seal 3740, e.g., polymeric netting 10 of FIG. 1.

The face seal 3740 can be attached to the mask body 3710 using any suitable technique or combination of techniques. In one or more embodiments, the face seal 3740 can be adhered to the mask body. In one or more alternative embodiments, the face of 3740 can be welded to the mask body 3710 as is further described herein regarding attachment of one or more straps to a mask body. Further, in one more alternative embodiments, the face seal 3740 can be attached to the mask body using staples, screws, or any other suitable fastening means.

Further, the face seal 3740 can be attached to any suitable portion of the mask body 3710. For example, the face seal 3740 can be attached to the interior surface 3719 of the mask body 3710. Alternatively, the face seal 3740 can be attached to the perimeter 3712 of the mask body 3710. In one or more alternative embodiments, the face seal 3740 can be attached to an exterior surface (e.g. exterior surface 3618 of respirator 3600 of FIG. 36) and folded over the upper perimeter segment 3714 such that it is configured to contact a sinus region of a wearer.

As is further described herein, the polymeric netting that can be included in the face seal 3740 can exhibit two or more contrasting colors. For example, in reference to polymeric netting 10 of FIG. 1, the ribbons 1 can exhibit a first color and the strands 3 can exhibit a second color. When compressed, the ribbons 1 can obscure at least some of the strands 3 from view such that the color of the ribbons is visible in the compressed regions but the color of the strands is not visible in such regions. In one or more embodiments, this visual effect can provide an indication to a wearer which portions of the face seal are sealed against the face and which portions are not sealed. These unsealed portions can indicate to a wearer that the respirator is not fully engaged with or sealed against the face, and an adjustment of, e.g., the nose clip is needed to properly seal the mask against the face.

The polymeric netting utilized for the face seals of the present disclosure can be positioned in any suitable location relative to the mask body 3710. In one or more embodiments, the polymeric netting can be positioned on the mask body 3710 such that the ribbons 1 are substantially parallel to perimeter 3712 of the mask body. As used herein, the term "substantially parallel to the perimeter" means that one or more ribbons 1 extend along a direction that forms an angle of less than 10° with a tangent to the perimeter 3712 adjacent to the one or more ribbons. Alternatively, the polymeric netting 3740 is disposed such that a distance from at least one ribbon 1 of the netting is at a substantially constant distance from the perimeter 3712 of the mask body 3710 that is adjacent the polymeric ribbon. AS used herein, the term "substantially constant distance" means that the distance between the ribbon 1 and the adjacent perimeter portion varies by no more than 10%.

In general, one or more embodiments of the polymeric netting described herein (e.g. polymeric netting 10 of FIG. 1) can be breathable in a direction substantially parallel to the height of the ribbons. For example, polymeric netting 30 of FIG. 3 can, in one or more embodiments, be permeable along a z-direction because the strands 33 that oscillate between ribbons 31 can be formed such that openings are positioned between the ribbons and strands. In one or more embodiments, the polymeric netting can be substantially impermeable to air along a direction parallel to a thickness of the ribbons. For example, as shown in FIG. 3, the polymeric netting 30 can be substantially impermeable to air along the x-direction.

By positioning the polymeric netting such that the ribbons are substantially parallel to the perimeter of the mask body 3710, the ribbons provide a barrier to ambient air such that the mask body is sealed against a face of a wearer. The seal can be further enhanced because of the flexibility of the ribbons. For example, when a wearer positions respirator 3700 on the face, the harness 3730 can firmly fix the respirator against the face such that the ribbons are compressed or deflected. This deflection can further seal the mask body 3710 against the face of the wearer and prevent ambient air from entering the mask body 3710 along the perimeter 3712. Because of the openings formed between the ribbons and the strands, the face seal can be permeable in a direction parallel to the height of the ribbons (i.e., the z-direction as shown in FIG. 3), allowing the face seal 3740 to be at least partially permeable to air or other fluids. This permeability along the z-direction can enhance comfort to a wearer and prevent moisture from being trapped between the face seal 3740 and the face. Further, in one or more embodiments, the polymeric netting utilized for face seal 3740 can also provide channels in a direction parallel to the length of the ribbons (i.e., the y-direction as shown in FIG. 3, which is a direction orthogonal to the Figure) such that moisture can be transported away from the face of a wearer along the channels.

Figure 38:
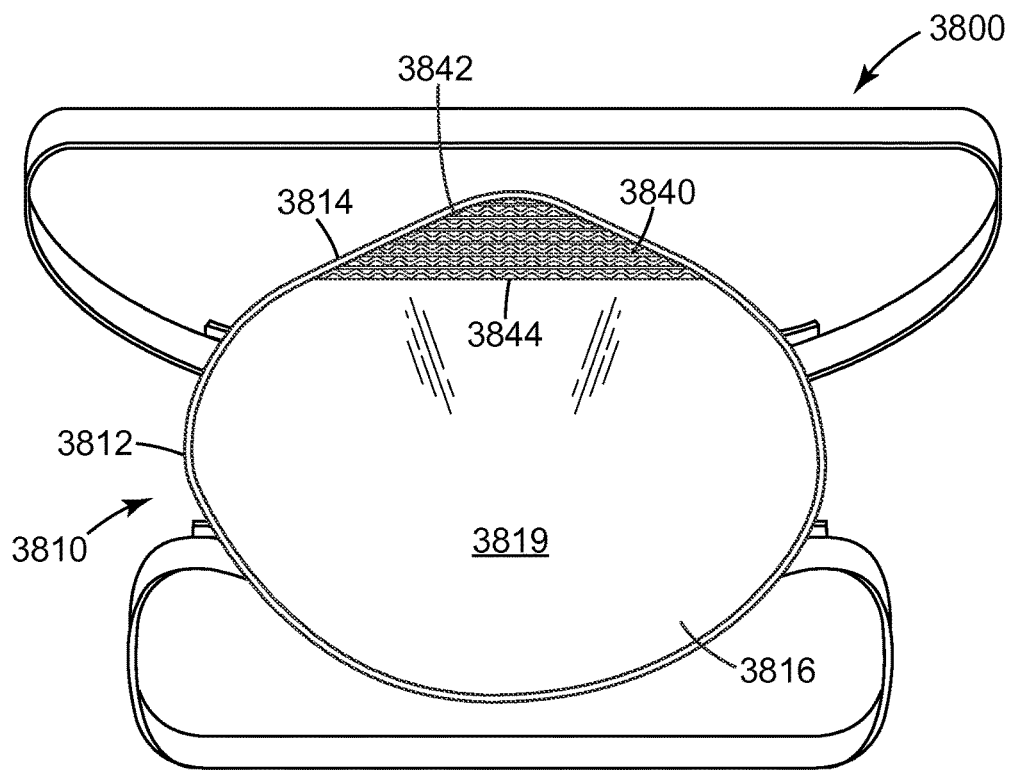
FIG. 38 is a schematic rear view of another embodiment of a respirator.

As mentioned herein, the face seals of the respirators described herein can take any suitable shape. For example, FIG. 38 is a schematic rear view of a respirator 3800. All of the design considerations and possibilities regarding the respirator 3600 of FIG. 36 and the respirator 3700 of FIG. 37 apply equally to the respirator 3800 of FIG. 38.

The respirator 3800 includes a face seal 3840 attached to a mask body 3810 adjacent an upper perimeter segment 3814 of perimeter 3812 of mask body 3810. In the illustrated embodiment, the face seal 3840 has taken a wedge shape having a first edge 3842 and a second edge 3844. The first edge 3842 is disposed adjacent the upper perimeter segment 3814 and generally takes the shape of or follows the shape or curve of the upper perimeter segment. And the second edge 3844 of the face seal 3840 has taken a linear shape.

Face seal 3840 can be attached in any suitable location on the mask body 3810. For example, the face seal 3840 can be attached to the upper perimeter segment 3814 of the perimeter 3812 such that it extends in a plane parallel to a plane that contains the perimeter 3812 of the mask body 3810. In one or more embodiments, the face seal 3840 can be attached to a portion of the perimeter 3812 and a portion of the interior surface 3819 of the mask body 3810.

Figure 39:
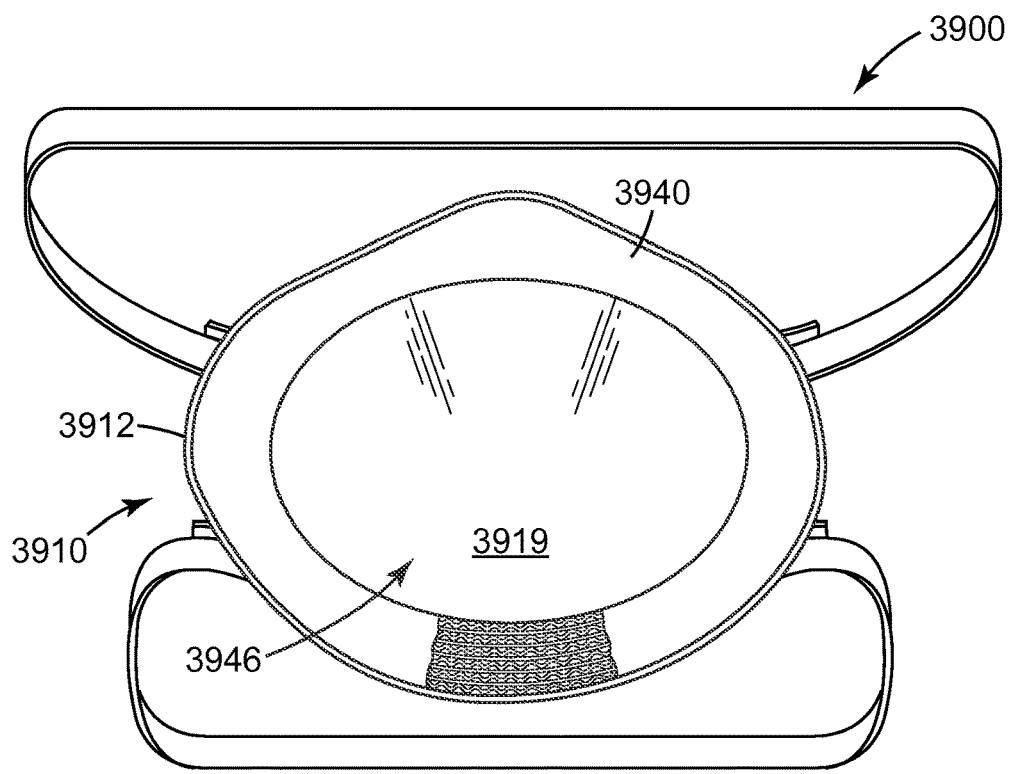
FIG. 39 is a schematic rear view of another embodiment of a respirator.

In one or more alternative embodiments, a face seal can be disposed adjacent the entire perimeter of a mask body. For example, FIG. 39 is a schematic rear view of another embodiment of a respirator 3900. All of the design considerations and possibilities regarding the respirator 3600 of FIG. 36 and the respirator 3700 of FIG. 37 apply equally to the respirator 3900 of FIG. 39. The respirator 3900 includes a mask body 3910 and a face seal 3940 that is disposed adjacent the entirety of perimeter 3912 of the mask body 3910. The face seal 3940 can take any suitable shape. In one or more embodiments, the face seal 3940 can take the shape of the perimeter 3912 of the mask body 3910. The face seal 3940 can also include an opening 3946 to allow a face of a wearer to be positioned within an interior space of the mask body 3910 adjacent an interior surface 3919 of the mask body. The opening 3946 can be any suitable size to accommodate the face of the wearer. The face seal 3940 can be configured to contact the face of a wearer and seal the respirator 3900 against the face.

In one or more embodiments, the various embodiments of face seals described herein can include a polymeric netting that exhibits a percent recovery after stress has been applied to the polymeric netting and then released. Polymeric netting that exhibits a greater percent recovery may provide a more effective seal between a respirator and a face of a wearer. In one or more embodiments, the polymeric netting may include a percent recovery of at least 90%. In one or more embodiments, the polymeric netting may include a percent recovery in a range of 90% to 100%.

Further, in one or more embodiments, the polymeric nettings of the present disclosure can exhibit an improved deformation recovery time, i.e., the time that it takes for the polymeric netting to recover at least 90% from the original deformation once the load has been released. Polymeric nettings that exhibit a faster recovery time may in one or more embodiments provide a more effective seal between a respirator and a face of a wearer. For example, in certain environments, portions of a perimeter of a respirator may become separated from the face of a wearer due to the wearer's face moving relative to the perimeter of the respirator. In such circumstances, the face seal may become disengaged from the face of the wearer and then reengaged in a different location on the face. The face seal may, therefore, be repositioned against a different portion of the face of the wearer that may have a different contour or shape. A polymeric netting that exhibits a faster recovery time may provide a more effective seal between the respirator and the face of the wearer by being capable of quickly taking on or conforming to a new portion or contour of the face of the wearer. In one or more embodiments, the polymeric netting may include a deformation recovery time of less than 60 seconds, 30 seconds, 20 seconds, 15, seconds, 10 seconds, etc.

Any suitable material or combination of materials can be used to form the polymeric netting that can be utilized for one or more straps of the harnesses described herein and/or one or more face seals. For example, the polymeric netting can include a saturated SEBS block copolymer such as Kraton G 1643, 6843, or 1657; saturated SEBS block copolymers blended with, e.g., mineral oil, Vistamaxx, high melt flow index polypropelyne; unsaturated SBS based formulas containing SBS (e.g., Vector 2518), poly (alpha methyl styrene), ethylene-vinyl acetate copolymer (EVA), mineral oil; expancel to create extrudable foam and additives to create a hydrophobic and hydrophilic material as in co-extrusion of a polymeric ribbon; and combinations thereof.

Hearing Protectors

The various embodiments of polymeric nettings described herein can be utilized in many different applications. For example, in one or more embodiments, a polymeric netting can be utilized in a hearing protector that includes two ear cups designed to cover the ears of a wearer. The hearing protector can, in one or more embodiments, include sealing rings that are secured along peripheries of the ear cups. These sealing rings can include any suitable embodiment of polymeric netting, e.g., polymeric netting 10 of FIG. 1.

Figure 41:
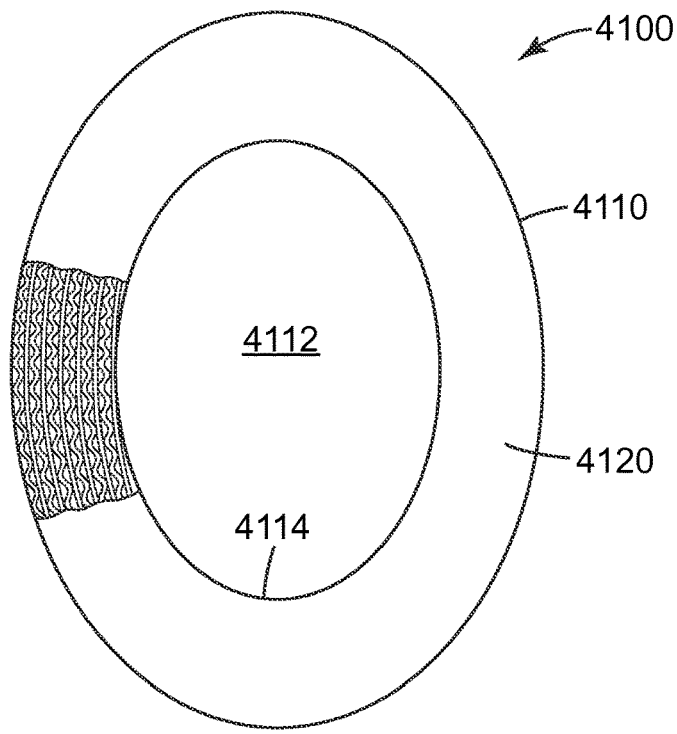
FIG. 41 is a schematic plan view of one embodiment of a hearing protector.

For example, FIG. 41 is a schematic plan view of one embodiment of a hearing protector that displays an oval outer contour 4110. This contour 4110 is the outer contour of sealing ring 4100, which is secured along a periphery of an ear cup (not shown). The outer contour of the sealing ring 4100 can take any suitable shape, e.g., oval, but its detailed configuration may vary considerably from a substantially more circular shape to a considerably more flattened elongate oval configuration. As illustrated in FIG. 41, the sealing ring 4100 includes a central region 4112 that is defined by an inner contour 4114. The sealing ring 4100 can include a polymeric netting 4120. Any suitable polymeric netting can be utilized with sealing ring 4100, e.g., polymeric netting 10 of FIG. 1. In one or more embodiments, the polymeric netting 4120 can be disposed such that ribbons of the polymeric netting form a number of circumferential ribbons disposed in a radial direction with inter-spacing outside one another.

Figure 42:
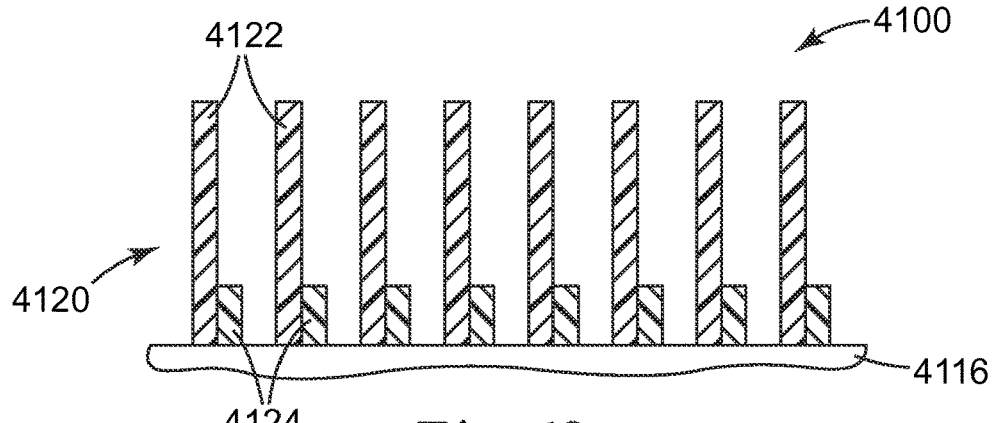
FIG. 42 is a schematic cross-section view of the hearing protector of FIG. 41.

For example, FIG. 42 is a schematic cross-section view of a portion of the sealing ring 4100 of FIG. 41. The polymeric netting 4120 includes ribbons 4122 and strands 4124. The polymeric netting 4120 is disposed on substrate or mounting plate 4116 that can also be annular and substantially planar. The mounting plate 4116 can be manufactured from any suitable material or combination of materials, e.g., configurationally stable material, e.g., injection molded plastic material. In one or more embodiments, the mounting plate 4116 can include one or more fixing elements (not shown) for attaching the sealing ring 4100 to an ear cup.

Some Embodiments of the Disclosure

In a first embodiment, the present disclosure provides a respirator that includes polymeric netting comprising polymeric ribbons and polymeric strands, each of the polymeric ribbons and strands having a length and width, wherein the length is the longest dimension and the width is the shortest dimension, wherein the polymeric ribbons have a height-to-width aspect ratio of at least five to one, a major surface that is intermittently bonded to only one polymeric strand, and a height that is at least two times greater than a height of the one polymeric strand.

In a second embodiment, the present disclosure provides the respirator of the first embodiment, wherein the polymeric ribbons each have a center line bisecting the major surface and first and second edges symmetrically disposed on opposite sides of the center line, wherein the major surface is intermittently bonded to only one polymeric strand at a location closer to the first edge than the second edge.

In a third embodiment, the present disclosure provides the polymeric netting of the first or second embodiment, wherein the polymeric ribbons each have a center line bisecting the major surface and first and second edges symmetrically disposed on opposite sides of the center line, wherein the polymeric netting has first and second opposing major surfaces transverse to the major surfaces of the polymeric ribbons, wherein the first major surface of the polymeric netting includes the first edges of the polymeric ribbons, and wherein the second major surface includes the second edges of the polymeric ribbons and portions of at least some of the polymeric strands.

In a fourth embodiment, the present disclosure provides the polymeric netting of the first embodiment, wherein the polymeric ribbons each have a center line bisecting the major surface, and wherein the major surface is intermittently bonded to only one polymeric strand at a location including the center line.

In a fifth embodiment, the present disclosure provides the polymeric netting of the first or fourth embodiment, wherein the polymeric ribbons and polymeric strands are vertically centered.

In a sixth embodiment, the present disclosure provides the polymeric netting of the first, second, fourth, or fifth embodiment, wherein the polymeric ribbons each have a center line bisecting the major surface and first and second edges symmetrically disposed on opposite sides of the center line, wherein the polymeric netting has first and second opposing major surfaces transverse to the major surfaces of the polymeric ribbons, wherein the first major surface of the polymeric netting includes the first edges of the polymeric ribbons, and wherein the second major surface includes the second edges of the polymeric ribbons, and wherein neither the first nor second major surfaces include a portion of the polymeric strands.

In a seventh embodiment, the present disclosure provides the polymeric netting of the first embodiment, wherein the polymeric ribbons each have a center line bisecting the major surface and first and second edges symmetrically disposed on opposite sides of the center line, wherein the major surface of a first portion of the polymeric ribbons is bonded to only one polymeric strand at a location closer to the first edge than the second edge and the major surface of a second portion of the polymeric ribbons is bonded to only one polymeric strand at a location closer to the second edge than the first edge.

In an eighth embodiment, the present disclosure provides the polymeric netting of the first, fourth, or seventh embodiment, wherein the polymeric ribbons each have a center line bisecting the major surface and first and second edges symmetrically disposed on opposite sides of the center line, wherein the polymeric netting has first and second opposing major surfaces transverse to the major surfaces of the polymeric ribbons, wherein the first major surface of the polymeric netting includes the first edges of a first portion of the polymeric ribbons, wherein the second major surface includes the second edges of the polymeric ribbons, wherein the first portion of the polymeric ribbons does not extend to the second major surface, and wherein the second portion of the polymeric ribbons does not extend to the first major surface.

In a ninth embodiment, the present disclosure provides the polymeric netting of any one of the first to eighth embodiments, wherein the polymeric ribbons each have a center line bisecting the major surface and first and second edges symmetrically disposed on opposite sides of the center line, wherein the first edges of the polymeric ribbons include a different composition than the second edges of the polymeric ribbons.

In a tenth embodiment, the present disclosure provides the polymeric netting of any one of the first to ninth embodiments, wherein the polymeric ribbons and polymeric strands alternate in at least a portion of the polymeric netting.

In an eleventh embodiment, the present disclosure provides the polymeric netting of any one of the first to tenth embodiments, wherein the polymeric strands and polymeric ribbons do not intersect each other.

In a twelfth embodiment, the present disclosure provides the polymeric netting of any one of the first to eleventh embodiments, wherein the height-to-width aspect ratio of at least some of the polymeric ribbons is greater than 7 to 1.

In a thirteenth embodiment, the present disclosure provides the polymeric netting of any one of the first to twelfth embodiments, wherein the height of at least some of the polymeric ribbons is greater than 750 micrometers.

In a fourteenth embodiment, the present disclosure provides the polymeric netting of any one of the first to twelfth embodiments, wherein the height of at least some of the polymeric ribbons is less than 750 micrometers.

In a fifteenth embodiment, the present disclosure provides the polymeric netting of any one of the first to fourteenth embodiments, wherein at least some of the polymeric ribbons have a different color than at least some of the polymeric strands.

In a sixteenth embodiment, the present disclosure provides the polymeric netting of any one of the first to fifteenth embodiments, wherein at least some of the polymeric ribbons have a different polymeric composition than at least some of the polymeric strands.

In a seventeenth embodiment, the present disclosure provides the polymeric netting of any one of the first to sixteenth embodiments, wherein the polymeric ribbons are elastic, the polymeric strands are elastic, or both the polymeric ribbons and the polymeric strands are elastic.

In an eighteenth embodiment, the present disclosure provides the polymeric netting of any one of the first to seventeenth embodiments, wherein the polymeric ribbons are substantially straight.

In a nineteenth embodiment, the present disclosure provides the polymeric netting of any one of the first to eighteenth embodiments, wherein the polymeric ribbons do not have a uniform height.

In a twentieth embodiment, the present disclosure provides an absorbent article having a fluid intake surface including the polymeric netting of any one of the first to nineteenth embodiments.

In a twenty-first embodiment, the present disclosure provides the absorbent article of the twentieth embodiment, wherein the fluid intake surface is a topsheet, and wherein the absorbent article further includes a liquid impermeable backsheet and an absorbent core between the topsheet and the backsheet.

In a twenty-second embodiment, the present disclosure provides an absorbent article including a polymeric netting, a liquid impermeable backsheet, and an absorbent core, wherein the polymeric netting includes polymeric ribbons and polymeric strands, each of the polymeric ribbons and strands having a length and width, wherein the length is the longest dimension and the width is the shortest dimension, wherein the polymeric ribbons have a height-to-width aspect ratio of at least three to one, a major surface that is intermittently bonded multiple times to a polymeric strand, and a height that is greater than a height of the one polymeric strand, and wherein the absorbent core is between the polymeric netting and the backsheet, wherein the polymeric netting is between the absorbent core and the backsheet, or wherein the polymeric netting is within the absorbent core.

In a twenty-third embodiment, the present disclosure provides the absorbent article of the twenty-second embodiment, wherein the polymeric netting is a topsheet.

In a twenty-fourth embodiment, the present disclosure provides the absorbent article of the twenty-second embodiment, wherein the polymeric netting is an acquisition layer between a topsheet and the absorbent core.

In a twenty-fifth embodiment, the present disclosure provides the absorbent article of any one of the twenty-second to twenty-fourth embodiments, wherein the polymeric ribbons each have a center line bisecting the major surface and first and second edges symmetrically disposed on opposite sides of the center line, wherein the major surface is intermittently bonded to only one polymeric strand at a location closer to the first edge than the second edge.

In a twenty-sixth embodiment, the present disclosure provides the absorbent article of any one of the twenty-second to twenty-fifth embodiments, wherein the polymeric ribbons each have a center line bisecting the major surface and first and second edges symmetrically disposed on opposite sides of the center line, wherein the polymeric netting has first and second opposing major surfaces transverse to the major surfaces of the polymeric ribbons, wherein the first major surface of the polymeric netting includes the first edges of the polymeric ribbons, and wherein the second major surface includes the second edges of the polymeric ribbons and portions of at least some of the polymeric strands.

In a twenty-seventh embodiment, the present disclosure provides the absorbent article of any one of the twenty-second to twenty-fifth embodiments, wherein the polymeric ribbons each have a center line bisecting the major surface, and wherein the major surface is intermittently bonded to only one polymeric strand at a location including the center line.

In a twenty-eighth embodiment, the present disclosure provides the absorbent article of any one of the twenty-second to twenty-fourth or twenty-seventh embodiments, wherein the polymeric ribbons and polymeric strands are vertically centered.

In a twenty-ninth embodiment, the present disclosure provides the absorbent article of any one of the twenty-second to twenty-fourth, twenty-seventh, or twenty-eighth embodiment, wherein the polymeric ribbons each have a center line bisecting the major surface and first and second edges symmetrically disposed on opposite sides of the center line, wherein the polymeric netting has first and second opposing major surfaces transverse to the major surfaces of the polymeric ribbons, wherein the first major surface of the polymeric netting includes the first edges of the polymeric ribbons, and wherein the second major surface includes the second edges of the polymeric ribbons, and wherein neither the first nor second major surfaces include a portion of the polymeric strands.

In a thirtieth embodiment, the present disclosure provides the absorbent article of any one of the twenty-second to twenty-fourth embodiments, wherein the polymeric ribbons each have a center line bisecting the major surface and first and second edges symmetrically disposed on opposite sides of the center line, wherein the major surface of a first portion of the polymeric ribbons is bonded to only one polymeric strand at a location to the first edge than the second edge and the major surface of a second portion of the polymeric ribbons is bonded to only one polymeric strand at a location closer to the second edge than the first edge.

In a thirty-first embodiment, the present disclosure provides the absorbent article of any one of the twenty-second to twenty-fourth or thirtieth embodiments, wherein the polymeric ribbons each have a center line bisecting the major surface and first and second edges symmetrically disposed on opposite sides of the center line, wherein the polymeric netting has first and second opposing major surfaces transverse to the major surfaces of the polymeric ribbons, wherein the first major surface of the polymeric netting includes the first edges of a first portion of the polymeric ribbons, wherein the second major surface includes the second edges of the polymeric ribbons, wherein the first portion of the polymeric ribbons does not extend to the second major surface, and wherein the second portion of the polymeric ribbons does not extend to the first major surface.

In a thirty-second embodiment, the present disclosure provides the absorbent article of any one of the twenty-second to thirty-first embodiments, wherein the polymeric ribbons each have a center line bisecting the major surface and first and second edges symmetrically disposed on opposite sides of the center line, wherein the first edges of the polymeric ribbons include a different composition than the second edges of the polymeric ribbons.

In a thirty-third embodiment, the present disclosure provides the absorbent article of any one of the twenty-second to thirty-second embodiments, wherein the polymeric ribbons and polymeric strands alternate in at least a portion of the polymeric netting.

In thirty-fourth embodiment, the present disclosure provides the absorbent article of any one of the twenty-second to thirty-third embodiments, wherein the polymeric strands and polymeric ribbons do not intersect each other.

In a thirty-fifth embodiment, the present disclosure provides the absorbent article of any one of the twenty-second to thirty-fourth embodiments, wherein the height-to-width aspect ratio of at least some of the polymeric ribbons is at least 5 to 1.

In a thirty-sixth embodiment, the present disclosure provides the absorbent article of any one of the twenty-second to thirty-fifth embodiments, wherein the height of at least some of the polymeric ribbons is greater than 750 micrometers.

In a thirty-seventh embodiment, the present disclosure provides the absorbent article of any one of the twenty-second to thirty-fifth embodiments, wherein the height of at least some of the polymeric ribbons is less than 750 micrometers.

In a thirty-eighth embodiment, the present disclosure provides the absorbent article of any one of the twenty-second to thirty-seventh embodiments, wherein at least some of the polymeric ribbons have a different color than at least some of the polymeric strands.

In a thirty-ninth embodiment, the present disclosure provides the absorbent article of any one of the twenty-second to thirty-eighth embodiments, wherein at least some of the polymeric ribbons have a different polymeric composition than at least some of the polymeric strands.

In a fortieth embodiment, the present disclosure provides the absorbent article of any one of the twenty-second to thirty-ninth embodiments, wherein the polymeric ribbons are elastic, the polymeric strands are elastic, or both the polymeric ribbons and the polymeric strands are elastic.

In forty-first embodiment, the present disclosure provides the absorbent article of any one of the twenty-second to fortieth embodiments, wherein the polymeric ribbons are substantially straight.

In a forty-second embodiment, the present disclosure provides the absorbent article of any one of the twenty-second to forty-first embodiments, wherein the polymeric ribbons do not have a uniform height.

In a forty-third embodiment, the present disclosure provides an extrusion die including at least one cavity, a dispensing surface, and fluid passageways between the at least one cavity and the dispensing surface, wherein the dispensing surface has an array of first dispensing orifices separated by an array of second dispensing orifices, wherein the first dispensing orifices, second dispensing orifices, and any other dispensing orifices are arranged in a single row across the dispensing surface, wherein the first and second dispensing orifices each have a top edge, a bottom edge, a height that is the distance between the top edge and the bottom edge, and a width, wherein the first dispensing orifices each have a height-to-width aspect ratio of at least five to one, and wherein the height of the first dispensing orifices is at least three times larger than the height of the second dispensing orifices.

In a forty-fourth embodiment, the present disclosure provides the extrusion die of the forty-third embodiment, wherein the fluid passageways are provided by a plurality of sequences of shims, wherein each sequence includes at least one first shim that provides a fluid passageway.

In a forty-fifth embodiment, the present disclosure provides the extrusion die of the forty-third embodiment, wherein the extrusion die includes at least a first and second cavity, first fluid passageways between the first cavity and the first dispensing orifices, and second fluid passageways between the second cavity and the second dispensing orifices.

In a forty-sixth embodiment, the present disclosure provides the extrusion die of the forty-fifth embodiment, wherein the fluid passageways are provided by a plurality of sequences of shims, wherein each sequence includes at least one first shim that provides the first fluid passageway, and at least one second shim that provides the second fluid passageway.

In a forty-seventh embodiment, the present disclosure provides the extrusion die of any one of the forty-third to forty-sixth embodiments, wherein at least the first dispensing orifices are defined by an array of first vestibules, the die further including a third cavity, a first fluid passageway between the first cavity and one of the first vestibules, a third passageway extending from the third cavity to the same vestibule, such that the area where the third fluid passageway enters the first vestibule is below the area where the first fluid passageway enters the first vestibule.

In a forty-eighth embodiment, the present disclosure provides the extrusion die of the forty-seventh embodiment, wherein the fluid passageways are provided by a plurality of sequences of shims, wherein each sequence includes at least one first shim that provides the first fluid passageway, and at least one third shim that provides the third fluid passageway.

In a forty-ninth embodiment, the present disclosure provides the extrusion die of any one of the forty-third to forty-eighth embodiments, wherein the second dispensing orifices are vertically aligned closer to the bottom edges than the top edges of the first dispensing orifices.

In a fiftieth embodiment, the present disclosure provides the extrusion die of any one of the forty-third to forty-eighth embodiments, wherein the first and second dispensing orifices are vertically centered.

In a fifty-first embodiment, the present disclosure provides the extrusion die of any one of the forty-third to forty-eighth embodiments, wherein the second dispensing orifices are vertically aligned, and wherein a first portion of the first dispensing orifices have their bottom edges closer to the second dispensing orifices than their top edges, and wherein a second portion of the first dispensing orifices have their top edges closer to the second dispensing orifices than their bottom edges.

In a fifty-second embodiment, the present disclosure provides the extrusion die of any one of the forty-third to fifty-first embodiments, wherein the height-to-width aspect ratio of at least some of the first dispensing orifices is at least 11 to 1.

In a fifty-third embodiment, the present disclosure provides the extrusion die of any one of the forty-third to fifty-second embodiments, wherein the first dispensing orifices do not have a uniform height.

In a fifty-fourth embodiment, the present disclosure provides a method of making a polymeric netting, the method including:
providing the extrusion die of any one of the forty-third to fifty-second embodiments; and dispensing polymeric ribbons from the first dispensing orifices at a first speed while simultaneously dispensing polymeric strands from the second dispensing orifices at a second speed to provide the polymeric netting, wherein the first speed is at least twice the second speed, or wherein the second speed is at least twice the first speed.

In a fifty-fifth embodiment, the present disclosure provides a method of making a polymeric netting, the method including:
providing an extrusion die including at least one cavity, a dispensing surface, and fluid passageways between the at least one cavity and the dispensing surface, wherein the dispensing surface has an array of first dispensing orifices separated by an array of second dispensing orifices, wherein the first and second dispensing orifices each have a top edge, a bottom edge, a height that is the distance between the top edge and the bottom edge, and a width, wherein the first dispensing orifices each have a height-to-width aspect ratio of at least five to one, and wherein the height of the first dispensing orifices is at least two times larger than the height of the second dispensing orifices;
dispensing polymeric ribbons from the first dispensing orifices at a first speed while simultaneously dispensing polymeric strands from the second dispensing orifices at a second speed to provide the polymeric netting, wherein the second speed is at least twice the first speed.

In a fifty-sixth embodiment, the present disclosure provides the method of the fifty-fifth embodiment, wherein the fluid passageways are provided by a plurality of sequences of shims, wherein each sequence includes at least one first shim that provides a fluid passageway.

In a fifty-seventh embodiment, the present disclosure provides the method of the fifty-fifth embodiment, wherein the extrusion die includes at least a first and second cavity, first fluid passageways between the first cavity and the first dispensing orifices, and second fluid passageways between the second cavity and the second dispensing orifices.

In a fifty-eighth embodiment, the present disclosure provides the method of the fifty-seventh embodiment, wherein the fluid passageways are provided by a plurality of sequences of shims, wherein each sequence includes at least one first shim that provides the first fluid passageway, and at least one second shim that provides the second fluid passageway.

In a fifty-ninth embodiment, the present disclosure provides the method of the fifty-fifth or fifty-seventh embodiment, wherein at least the first dispensing orifices are defined by an array of first vestibules, the die further including a third cavity, a first fluid passageway between the first cavity and one of the first vestibules, a third passageway extending from the third cavity to the same vestibule, such that the area where the third fluid passageway enters the first vestibule is above or below the area where the first fluid passageway enters the first vestibule.

In a sixtieth embodiment, the present disclosure provides the method of the fifty-ninth embodiment, wherein the fluid passageways are provided by a plurality of sequences of shims, wherein each sequence includes at least one first shim that provides the first fluid passageway, and at least one third shim that provides the third fluid passageway.

In a sixty-first embodiment, the present disclosure provides the method of any one of the fifty-fifth to sixtieth embodiments, wherein the polymeric ribbons are substantially straight.

In a sixty-second embodiment, the present disclosure provides the method of any one of the fifty-fifth to sixty-first embodiments, wherein the polymeric strands oscillate to at least partially alternately bond to two adjacent polymeric ribbons.

In a sixty-third embodiment, the present disclosure provides the method of any one of the fifty-fifth to sixty-second embodiments, wherein the polymeric strands and polymeric ribbons do not intersect each other.

In a sixty-fourth embodiment, the present disclosure provides the method of any one of the fifty-fifth to sixty-third embodiments, wherein the height-to-width aspect ratio of at least some of the first dispensing orifices is at least 11 to 1.

In a sixty-fifth embodiment, the present disclosure provides the method of any one of the fifty-fifth to sixty-fourth embodiments, wherein the height of at least some of the polymeric ribbons is greater than 750 micrometers.

In a sixty-sixth embodiment, the present disclosure provides the method of any one of the fifty-fifth to sixty-fourth embodiments, wherein the height of at least some of the polymeric ribbons is less than 750 micrometers.

In a sixty-seventh embodiment, the present disclosure provides the method of any one of the fifty-fifth to sixty-sixth embodiments, wherein at least some of the polymeric ribbons have a different color than at least some of the polymeric strands.

In a sixty-eighth embodiment, the present disclosure provides the method of any one of the fifty-fifth to sixty-seventh embodiments, wherein at least some of the polymeric ribbons have a different polymeric composition than at least some of the polymeric strands.

In a sixty-ninth embodiment, the present disclosure provides the method of any one of the fifty-fifth to sixty-eighth embodiments, wherein the polymeric ribbons are elastic, the polymeric strands are elastic, or both the polymeric ribbons and the polymeric strands are elastic.

In a seventieth embodiment, the present disclosure provides the method of any one of the fifty-fifth to sixty-ninth embodiments, wherein the second dispensing orifices are vertically aligned closer to the bottom edges than the top edges of the first dispensing orifices.

In a seventy-first embodiment, the present disclosure provides the method any one of the fifty-fifth to seventieth embodiments, wherein the polymeric ribbons each have a center line bisecting the major surface and first and second edges symmetrically disposed on opposite sides of the center line, wherein the major surface is intermittently bonded to only one polymeric strand at a location between the center line and the first edge.

In a seventy-second embodiment, the present disclosure provides the method of the seventieth or seventy-first embodiment, wherein the polymeric ribbons each have a center line bisecting the major surface and first and second edges symmetrically disposed on opposite sides of the center line, wherein the polymeric netting has first and second opposing major surfaces transverse to the major surfaces of the polymeric ribbons, wherein the first major surface of the polymeric netting includes the first edges of the polymeric ribbons, and wherein the second major surface includes the second edges of the polymeric ribbons and portions of at least some of the polymeric strands.

In a seventy-third embodiment, the present disclosure provides the method of any one of the fifty-fifth to sixty-ninth embodiments, wherein the first and second dispensing orifices are vertically centered.

In a seventy-fourth embodiment, the present disclosure provides the method of any one of the fifty-fifth to sixty-ninth and seventy-third embodiments, wherein the polymeric ribbons each have a center line bisecting the major surface, and wherein the major surface is intermittently bonded to only one polymeric strand at a location including the center line.

In a seventy-fifth embodiment, the present disclosure provides the method of the seventy-third or seventy-fourth embodiment, wherein the polymeric ribbons and polymeric strands are vertically centered.

In a seventy-sixth embodiment, the present disclosure provides the method of any one of the fifty-fifth to sixty-ninth and seventy-third to seventy-fifth embodiments, wherein the polymeric ribbons each have a center line bisecting the major surface and first and second edges symmetrically disposed on opposite sides of the center line, wherein the polymeric netting has first and second opposing major surfaces transverse to the major surfaces of the polymeric ribbons, wherein the first major surface of the polymeric netting includes the first edges of the polymeric ribbons, and wherein the second major surface includes the second edges of the polymeric ribbons, and wherein neither the first nor second major surfaces include a portion of the polymeric strands.

In a seventy-eighth embodiment, the present disclosure provides the method of any one of the fifty-fifth to sixty-ninth embodiments, wherein the second dispensing orifices are vertically aligned, and wherein a first portion of the first dispensing orifices have their bottom edges closer to the second dispensing orifices than their top edges, and wherein a second portion of the first dispensing orifices have their top edges closer to the second dispensing orifices than their bottom edges.

In a seventy-ninth embodiment, the present disclosure provides the method of the seventy-eighth embodiment, wherein the first dispensing orifices alternate between top edges substantially aligned with the top edges of the second dispensing orifices and bottom edges substantially aligned with the bottom edges of the second dispensing orifices.

In an eightieth embodiment, the present disclosure provides the method of any one of the fifty-fifth to sixty-ninth, seventy-eighth or seventy-ninth embodiments, wherein the polymeric ribbons each have a center line bisecting the major surface and first and second edges symmetrically disposed on opposite sides of the center line, wherein the major surface of a first portion of the polymeric ribbons is bonded to only one polymeric strand at a location between the center line and the first edge and the major surface of a second portion of the polymeric ribbons is bonded to only one polymeric strand at a location between the center line at the second edge.

In an eighty-first embodiment, the present disclosure provides the method of any one of the fifty-fifth to sixty-ninth and seventy-eighth to eightieth embodiments, wherein the polymeric ribbons each have a center line bisecting the major surface and first and second edges symmetrically disposed on opposite sides of the center line, wherein the polymeric netting has first and second opposing major surfaces transverse to the major surfaces of the polymeric ribbons, wherein the first major surface of the polymeric netting includes the first edges of a first portion of the polymeric ribbons, wherein the second major surface includes the second edges of the polymeric ribbons, wherein the first portion of the polymeric ribbons does not extend to the second major surface, and wherein the second portion of the polymeric ribbons does not extend to the first major surface.

In an eighty-second embodiment, the present disclosure provides the polymeric netting of any one of the first to nineteenth embodiments joined to a carrier.

In an eighty-third embodiment, the present disclosure provides the polymeric netting of any one of the first to nineteenth embodiments for use as an elastic wrap.

In order that this disclosure can be more fully understood, the following examples are set forth. It should be understood that these examples are for illustrative purposes only, and are not to be construed as limiting this disclosure in any manner. All parts and percentages are by weight unless otherwise indicated.

EXAMPLES

Example 1

A co-extrusion die as generally depicted in FIGS. 22 and 23 and assembled with a multi shim repeating pattern of extrusion orifices as generally illustrated in FIGS. 12A and 12B was prepared. The thickness of the shims in the repeat sequence was 4 mils (0.102 mm). These shims were formed from stainless steel, with perforations cut by a wire electron discharge machining Referring to FIG. 11, the height of dispensing orifices 356 of shims 300 were cut to 100 mils (2.54 mm). Referring to FIG. 9, the height of the dispensing orifice 156 of shims 100 were cut to 30 mils (0.762 mm). The shims were stacked in a repeating sequence 100, 100, 200, 200, 300, 300, 200, 200. As assembled the width of the dispensing openings 1001 and 1003 were each 0.203 mm, and the land spacings between openings were 0.203 mm. The extrusion orifices were aligned in a collinear, alternating arrangement, and resulting dispensing surface was as shown in FIG. 12B. The total width of the shim setup was about 13 cm. (5 inches).

The inlet fittings on the two end blocks were each connected to three conventional single-screw extruders. Each extruder feeding cavities 1012a and 1012c were loaded with polypropylene homopolymer (obtained under the trade designation "1024PP" from Exxon Mobil, Irving, Tex.).

The flow rate of the polymer exiting openings 1003 was 1.7 kg/hr, and flow rate of the polymer exiting openings 1001 was 1.9 kg/hr. The melt was extruded vertically into an extrusion quench takeaway. The quench takeaway speed was 5.2 m/min, and the melt drop distance was 3 cm. The extrusion temperature was 218° C. The polymer exiting openings 1003 was oscillating. The quench roll was a smooth temperature controlled chrome plated 20-cm diameter steel roll. The quench temperature, which was 10° C., was controlled with internal water flow. The web path wrapped 180 degrees around the chrome steel roll and then to a windup roll.

Figure 30:
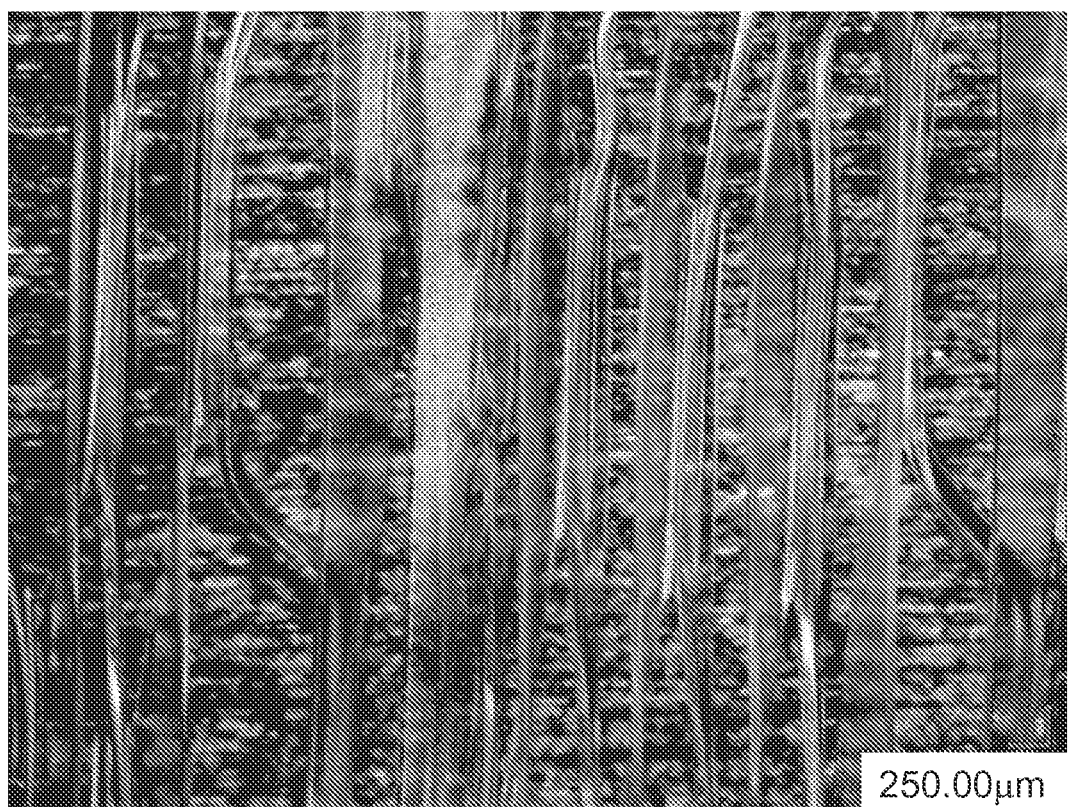
FIG. 30 is a photograph of a top view of the polymeric netting of Example 1.

A photograph of the polymeric netting obtained is shown in FIG. 30. Using an optical microscope at 30× magnification, the polymeric strand width and height were determined to be 80 micrometers and 373 micrometers respectively, and the polymeric ribbon width and height were determined to be 80 micrometers and 600 micrometers, respectively. The basis weight of the polymeric netting was measured by weighing three 2 inch by 10 inch (5.1 cm by 25.4 cm) pieces of the netting with an analytical balance and averaging the values. The basis weight of the polymeric netting was found to be 125 g/m², and its overall caliper was 600 micrometers.

The top sheet was removed from a 270 mm by 90 mm pad obtained from First Quality Retail Services, Macon, Ga., under the trade designation "OPTIONS ULTRA THINS", and the top sheet was replaced with a piece of the polymeric netting described above. The piece of the polymeric netting had dimensions of approximately 260 mm by 90 mm. The polymeric netting was placed on top of the acquisition/distribution layer without adhesive.

Example 1b

A piece of the polymeric netting (approximately 260 mm by 90 mm) made as described in Example 1 was soaked in a solution made from 90 grams of water and 10 grams of surfactant obtained from Dow Chemical Company, Midland, Mich., under the trade designation "TRITON X-100". After completely submerging the polymeric netting, it was immediately removed from the solution, and the excess liquid was allowed to drip off. The sample was placed on an aluminum tray and dried for two hours at 50° C. in a batch oven. The top sheet was removed from a 270 mm by 90 mm pad obtained from First Quality Retail Services under the trade designation "OPTIONS ULTRA THINS", and the top sheet was replaced with the soaked and dried polymeric netting. The polymeric netting was placed on top of the acquisition/distribution layer without adhesive.

Example 1c

The top sheet was removed from a 270 mm by 90 mm pad obtained from First Quality Retail Services under the trade designation "OPTIONS ULTRA THINS", and the acquisition/distribution was removed and replaced with a piece of the polymeric netting made as described in Example 1. The piece of the polymeric netting had dimensions of approximately 165 mm by 50 mm. The polymeric netting was placed on top of the absorbent without adhesive, and the original topsheet was positioned on top of the polymeric netting without adhesive.

Example 2

A co-extrusion die as generally depicted in FIGS. 22 and 23 and assembled with a multi shim repeating pattern of extrusion orifices as generally illustrated in FIGS. 15A and 15B, with the modification that one shim 500 was used instead of two, was prepared. The thickness of the shims in the repeat sequence was 4 mils (0.102 mm) for shims 400 and 200. The thickness of the shims in the repeat sequence was 8 mils (0.203 mm) for shims 500. These shims were formed from stainless steel, with perforations cut by a wire electron discharge machining Referring to FIG. 14, the height of the dispensing openings 556 of shims 500 were cut to 100 mils (2.54 mm). Referring to FIG. 13, the height of the dispensing openings 456 of shims 400 were cut to 20 mils (0.508 mm). The shims were stacked in a repeating sequence 400, 400, 400, 400, 200, 200, 200, 200, 500, 200, 200, 200, 200. As assembled the width of the dispensing openings 1103 and 1101 were 0.406 mm and 0.203 mm, respectively, and the land spacings between openings were 0.406 mm. The extrusion orifices were aligned in a collinear, alternating arrangement, and resulting dispensing surface was as shown in FIG. 15B. The total width of the shim setup was about 15 cm.

The inlet fittings on the two end blocks were each connected to three conventional single-screw extruders. Each extruder feeding cavities 1112a and 1112b were loaded with styrene-ethylene/butylene-styrene block copolymer elastomer (obtained under the trade designation "MD6751" from Kraton, Belpre, Ohio) dry blended with 3% yellow and green colorant masterbatch, respectively (yellow colorant obtained under the trade designation "PANTONE YELLOW" from Americhem, Cuyahoga Falls, Ohio, green obtained under the trade designation "PAN3385C MINT GREEN" from Clariant, Minneapolis, Minn.).

The flow rate of the yellow polymer exiting openings 1103 was 3.74 kg/hr, and flow rate of the green polymer exiting openings 1101 was 2.95 kg/hr. The melt was extruded vertically into an extrusion quench takeaway. The quench takeaway speed was 1.54 m/min, and the melt drop distance was 4 cm. The extrusion temperature was 232° C. The polymer exiting openings 1103 was oscillating. The quench roll was a smooth, temperature-controlled chrome plated 20-cm diameter steel roll. The quench temperature, which was 10° C., was controlled with internal water flow. The web was further cooled on the quench roll with compressed air flow through four 2.5-inch (6.35 cm) Loc-Line® Swivel Nozzle 75 (Lockwood Products, INC, Lake Oswego, Oreg.). The web path wrapped 180 degrees around the chrome steel roll and then to a windup roll.

Figure 31A:
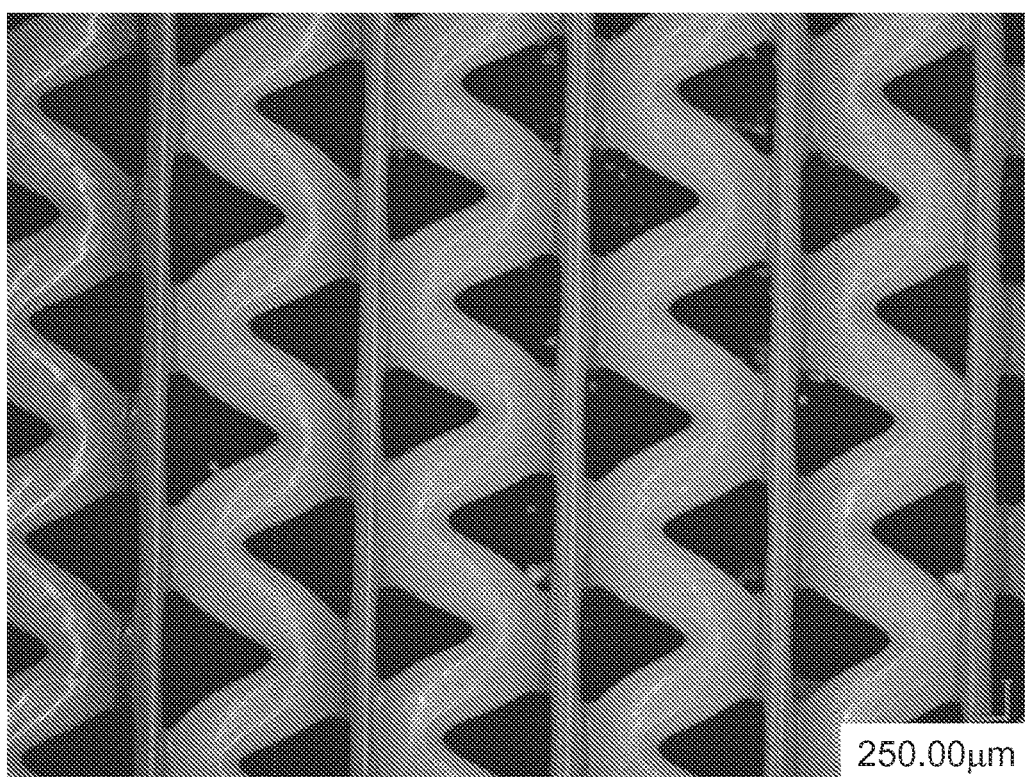
FIGS. 31A and 31B are photographs of top and side views, respectively, of the polymeric netting of Example 2.
Figure 31B:
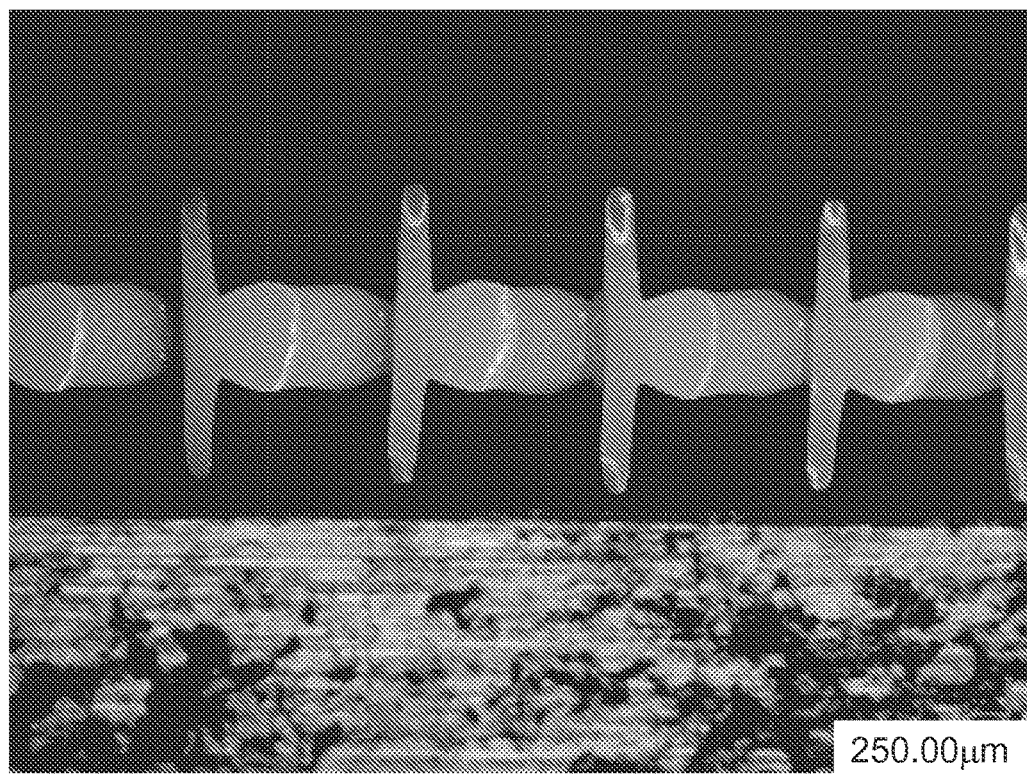

Photographs of the polymeric netting obtained are shown in FIGS. 31A and 31B. Using an optical microscope at 30× magnification, the polymeric strand width and height were determined to be 426 micrometers and 773 micrometers, respectively, and the polymeric ribbon width and height were determined to be 229 micrometers and 2066 micrometers, respectively. The basis weight of the polymeric netting was measured as described in Example 1 and found to be 568 g/m$^2$, and its overall caliper was 2066 micrometers.

Example 3

A co-extrusion die as generally depicted in FIGS. 22 and 23 and assembled with a multi shim repeating pattern of extrusion orifices as generally illustrated in FIGS. 21A and 21B, with the modification that one shim 500 was used instead of two, was prepared. The thickness of the shims in the repeat sequence was 4 mils (0.102 mm) for shims 800 and 200. The thickness of the shims in the repeat sequence was 8 mils (0.203 mm) for shims 500. The thickness of the shims in the repeat sequence was 2 mils (0.051 mm) for shims 900. These shims were formed from stainless steel, with perforations cut by a wire electron discharge machining Referring to FIG. 14, the height of the dispensing openings 556 of shims 500 were cut to 100 mils (2.54 mm). Referring to FIG. 19, the height of the dispensing openings 856 of shims 800 were cut to 15 mils (0.381 mm). The shims were stacked in a repeating sequence 800, 800, 800, 200, 200, 200, 900, 500, 900, 200, 200, 200. As assembled the width of the dispensing openings 1303 and 1301 were 0.305 mm and 0.203 mm, respectively, and the land spacings between openings were 0.305 mm. The extrusion orifices were aligned in a collinear, alternating arrangement, and resulting dispensing surface was as shown in FIG. 21B. The total width of the shim setup was about 10 cm.

The inlet fittings on the two end blocks were each connected to three conventional single-screw extruders. Each extruder feeding cavities 1312a and 1312b were loaded with styrene-ethylene/butylene-styrene block copolymer elastomer (obtained under the trade designation "MD6752" from Kraton, Belpre, Ohio) dry blended with 3% pink or black colorant masterbatch, respectively, (pink and black obtained under the trade designation "PAN813C NEON PINK" and "PANTONE BLACK C" from Clariant, Minneapolis, Minn.).

The flow rate of the pink polymer exiting openings 1303 was 2.04 kg/hr, and flow rate of the black polymer exiting openings 1301 was 3.61 kg/hr. The melt was extruded vertically into an extrusion quench takeaway. The quench takeaway speed was 1.67 m/min, and the melt drop distance was 4 cm. The extrusion temperature was 232° C. The polymer exiting openings 1303 was oscillating. The quench roll was a smooth, temperature-controlled chrome plated 20-cm diameter steel roll. The quench temperature, which was 10° C., was controlled with internal water flow. The web was further cooled on the quench roll with compressed air flow through four 2.5-inch (6.35 cm) Loc-Line® Swivel Nozzle 75 (Lockwood Products, INC, Lake Oswego, Oreg.). The web path wrapped 180 degrees around the chrome steel roll and then to a windup roll.

Figure 32A:
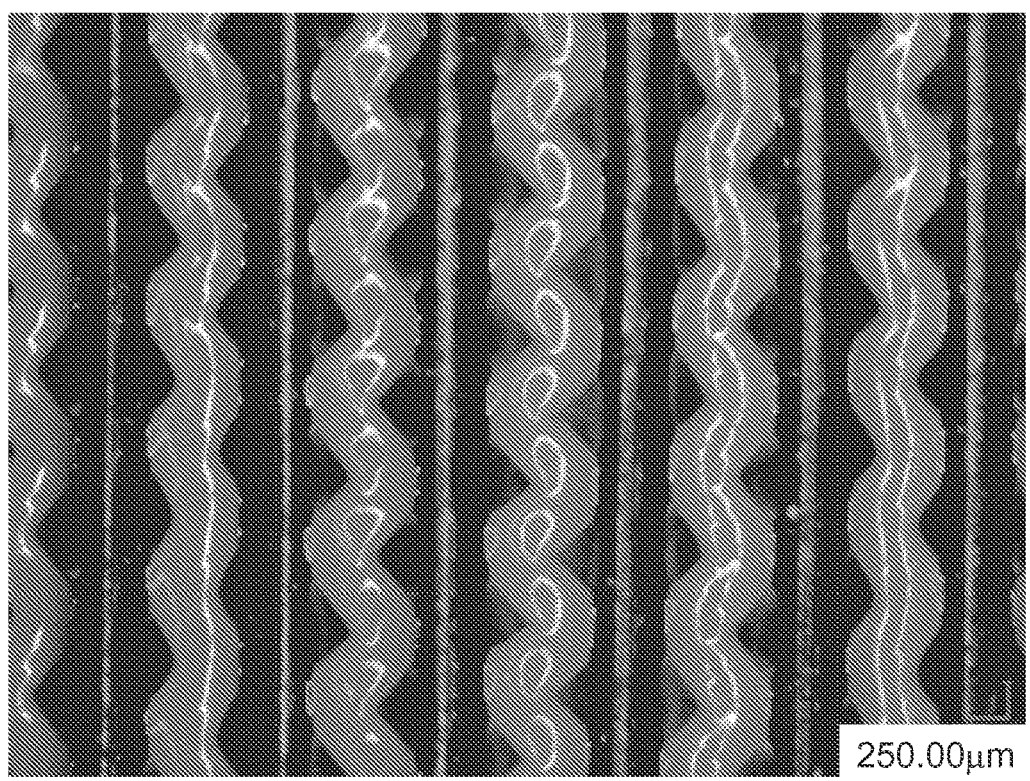
FIGS. 32A and 32B are photographs of top and side views, respectively, of the polymeric netting of Example 3.
Figure 32B:
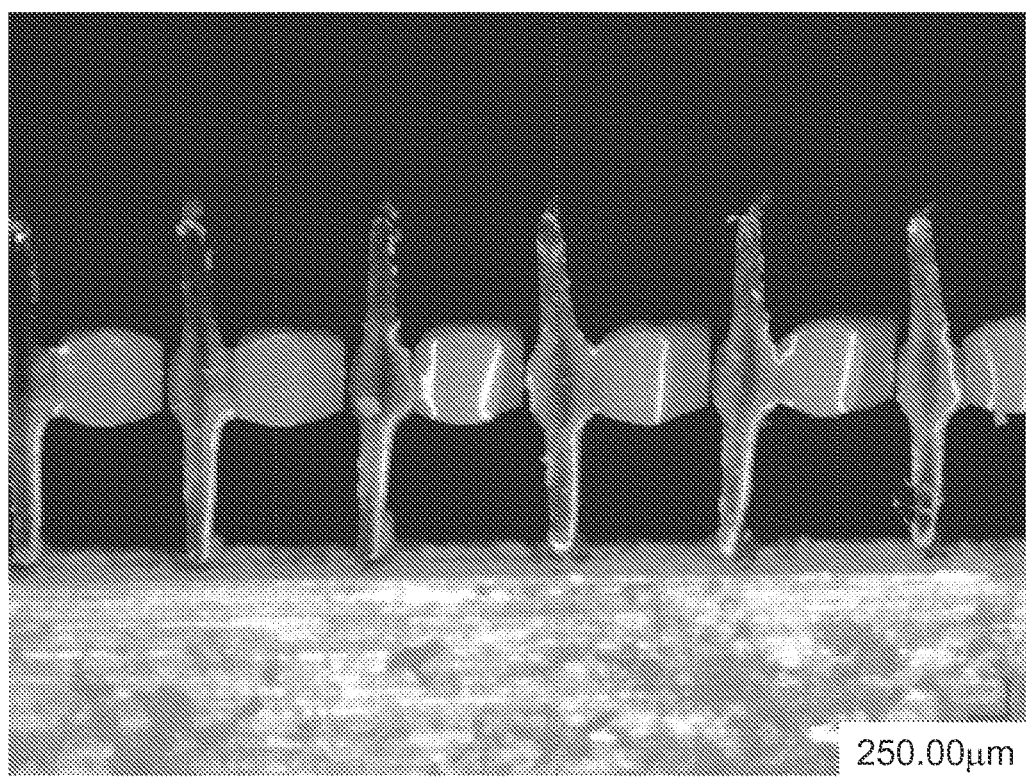

Photographs of the polymeric netting obtained are shown in FIGS. 32A and 32B. Using an optical microscope at 30× magnification, the polymeric strand width and height were determined to be 476 micrometers and 614 micrometers, respectively, and the polymeric ribbon width and height were determined to be 189 micrometers and 2365 micrometers, respectively. The basis weight of the polymeric netting was measured as described in Example 1 and found to be 649 g/m$^2$, and its overall caliper was 2365 micrometers.

Example 4

A co-extrusion die as generally depicted in FIGS. 22 and 23 and assembled with a multi shim repeating pattern of extrusion orifices as generally illustrated in FIGS. 18A and 18B was prepared. The thickness of the shims in the repeat sequence was 4 mils (0.102 mm) for shims 700, 200, 600, and 300. These shims were formed from stainless steel, with perforations cut by a wire electron discharge machining Referring to FIGS. 11 and 17, the heights of the dispensing openings 356 and 756 of shims 300 and 700 were both cut to 100 mils (2.54 mm). The height of the dispensing opening 656 of shims 600 were both cut to 30 mils (0.765 mm). The shims were stacked in a repeating sequence 700, 700, 200, 200, 600, 600, 200, 200, 300, 300, 200, 200, 600, 600, 200, 200. As assembled the width of the dispensing openings 1203 and 1201 were each 0.203 mm, and the land spacings between openings were 0.203 mm. The extrusion orifices were aligned in a collinear, alternating arrangement, and resulting dispensing surface was as shown in FIGS. 18A and 18B. The total width of the shim setup was about 12.5 cm.

The inlet fittings on the two end blocks were each connected to three conventional single-screw extruders. Each extruder feeding cavities 1212a, 1212b and 1212c were loaded with styrene-ethylene/butylene-styrene block copolymer elastomer (obtained under the trade designation "MD6751" from Kraton, Belpre, Ohio) dry blended with 3% pink, yellow, and purple colorant masterbatch, respectively, (yellow colorant obtained under the trade designation "YELLOW 116" from Americhem, Cuyahoga Falls, Ohio, neon pink and purple obtained under the trade designation "PAN813C NEON PINK" and "PAN266C PURPLE" from Clariant, Minneapolis, Minn.).

The flow rate of the pink polymer exiting openings 1201 was 2.0 kg/hr, and the flow rate of the yellow polymer exiting openings 1203 was 3.08 kg/hr, and the flow rate of the purple polymer exiting openings 1201 was 1.36 kg/hr. The melt was extruded vertically into an extrusion quench takeaway. The quench takeaway speed was 1.67 m/min, and the melt drop distance was 4 cm. The extrusion temperature was 232° C. The polymer exiting openings 1203 was oscillating. The quench roll was a smooth, temperature-controlled chrome plated 20-cm diameter steel roll. The quench temperature, which was 10° C., was controlled with internal water flow. The web was further cooled on the quench roll with compressed air flow through four 2.5-inch (6.35 cm) Loc-Line® Swivel Nozzle 75 (Lockwood Products, INC, Lake Oswego, Oreg.). The web path wrapped 180 degrees around the chrome steel roll and then to a windup roll.

Figure 33A:
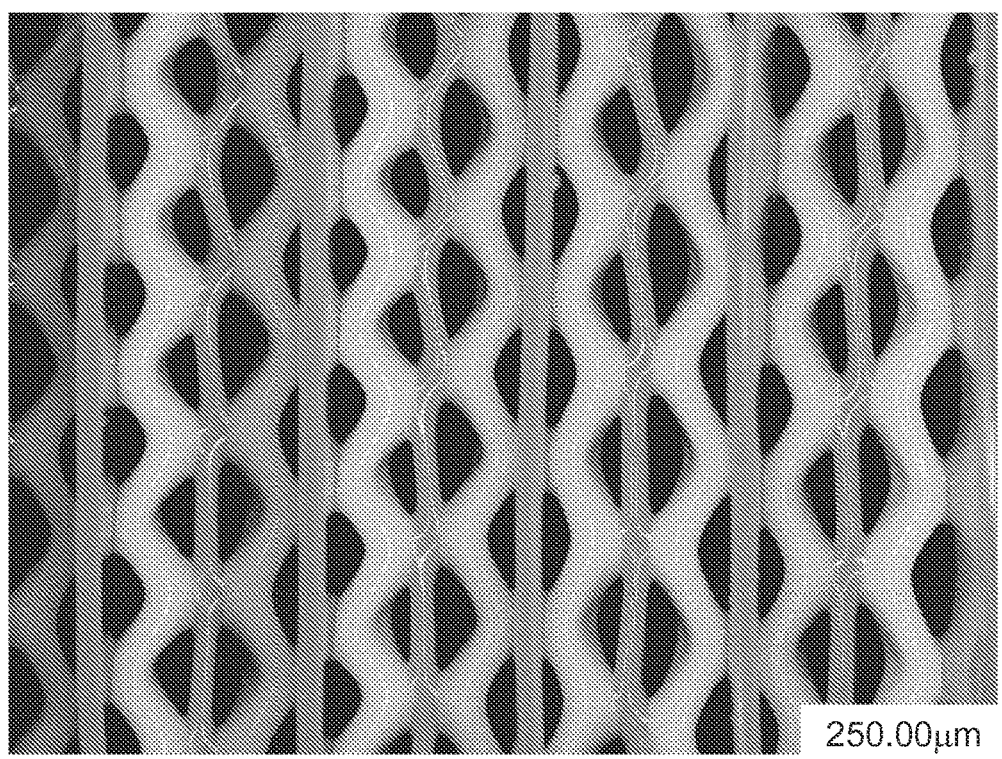
FIGS. 33A and 33B are photographs of top and side views, respectively, of the polymeric netting of Example 4.
Figure 33B:
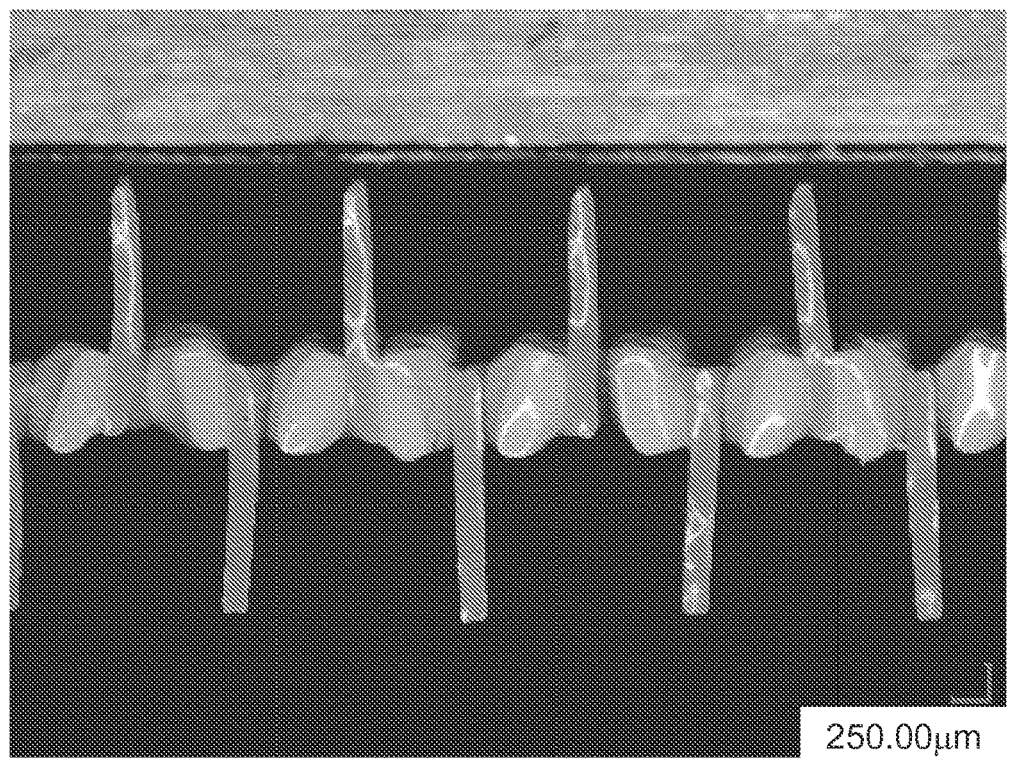

Photographs of the polymeric netting obtained are shown in FIGS. 33A and 33B. Using an optical microscope at 30× magnification, the polymeric strand width and height were determined to be 306 micrometers and 747 micrometers, respectively, the pink polymeric ribbon width and height were determined to be 204 micrometers and 1736 micrometers, respectively, and the purple polymeric ribbon width and height were determined to be 200 micrometers and 1782 micrometers, respectively. The basis weight of the polymeric netting was measured as described in Example 1 and found to be 680 g/m$^2$, and its overall caliper was 3.03 mm.

Example 4a

The top sheet was removed from a 270 mm by 90 mm pad obtained from First Quality Retail Services under the trade designation "OPTIONS ULTRA THINS", and the top sheet was replaced with a piece of the polymeric netting prepared in Example 4. The piece of the polymeric netting had dimensions of approximately 260 mm by 90 mm. The polymeric netting was placed on top of the acquisition/distribution layer without adhesive.

Example 4b

A piece of the polymeric netting made as described in Example 4 (approximately 260 mm by 90 mm) was soaked in a solution made from 90 grams of water and 10 grams of surfactant obtained from Dow Chemical Company under the trade designation "TRITON X-100", removed from the solution, and dried as described in Example 1b. The top sheet was removed from a 270 mm by 90 mm pad obtained from First Quality Retail Services under the trade designation "OPTIONS ULTRA THINS", and the top sheet was replaced with the soaked and dried polymeric netting. The polymeric netting was placed on top of the acquisition/distribution layer without adhesive.

Example 4c

The top sheet was removed from a 270 mm by 90 mm pad obtained from First Quality Retail Services under the trade designation "OPTIONS ULTRA THINS", and the acquisition/distribution was removed and replaced with a piece of the polymeric netting made as described in Example 4. The piece of the polymeric netting had dimensions of approximately 165 mm by 50 mm. The polymeric netting was placed on top of the absorbent without adhesive, and the original topsheet was positioned on top of the polymeric netting without adhesive.

Example 5

Example 5 was prepared using the method described above for Example 2 with the following modifications. The total width of the shim setup was about 13 cm. Each extruder feeding cavities 1112a and 1112b were loaded with styrene-ethylene/butylene-styrene block copolymer elastomer (obtained under the trade designation "G1645" from Kraton). No colorant was added. The extrusion temperature was 254° C. The quench takeaway speed was 1.52 m/min, and the melt drop distance was 3 cm. Using an optical microscope at 30× magnification, the polymeric strand width and height were determined to be 450 micrometers and 700 micrometers, respectively, and the polymeric ribbon width and height were determined to be 200 micrometers and 2400 micrometers, respectively. The basis weight of the polymeric netting was measured as described in Example 1 and found to be 641 g/m², and its overall caliper was 2400 micrometers.

Example 6

Example 6 was prepared using the method described above for Example 1 with the following modifications. Shim 400 shown in FIG. 13 was used instead of shim 100 shown in FIG. 9. The height of the dispensing openings 456 of shims 400 were cut to 20 mils (0.508 mm). The shims were stacked in a repeating sequence 400, 400, 200, 200, 300, 300, 200, 200. The total width of the shim setup was about 10 cm.

The inlet fittings on the two end blocks were each connected to three conventional single-screw extruders. Each extruder feeding cavities 1012a and 1012c were loaded with styrene-ethylene/butylene-styrene block copolymer elastomer (obtained under the trade designation "1130120" from Kraton) dry blended with 2 wt. % deep green and 3 wt. % green colorant masterbatches, respectively (deep green colorant was obtained under the trade designation "DEEP SATURATED GREEN", and green colorant was obtained under the trade designation "PAN802C GREEN", both from Clariant).

The flow rate of the polymer exiting openings 1003 in an oscillating fashion was 1.3 kg/hr, and flow rate of the polymer exiting openings 1001 was 2.25 kg/hr. The quench takeaway speed was 1.5 m/min, and the melt drop distance was 4 cm. The extrusion temperature was 232° C.

Figure 34A:
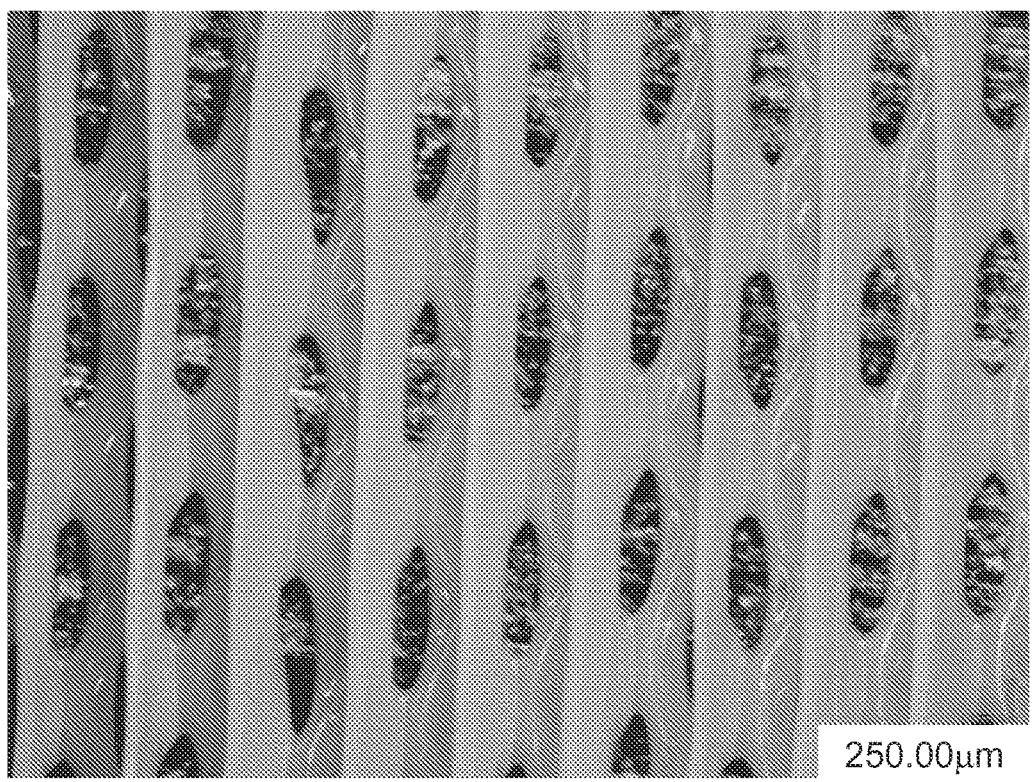
FIGS. 34A and 34B are photographs of top and side views, respectively, of the polymeric netting of Example 6.
Figure 34B:
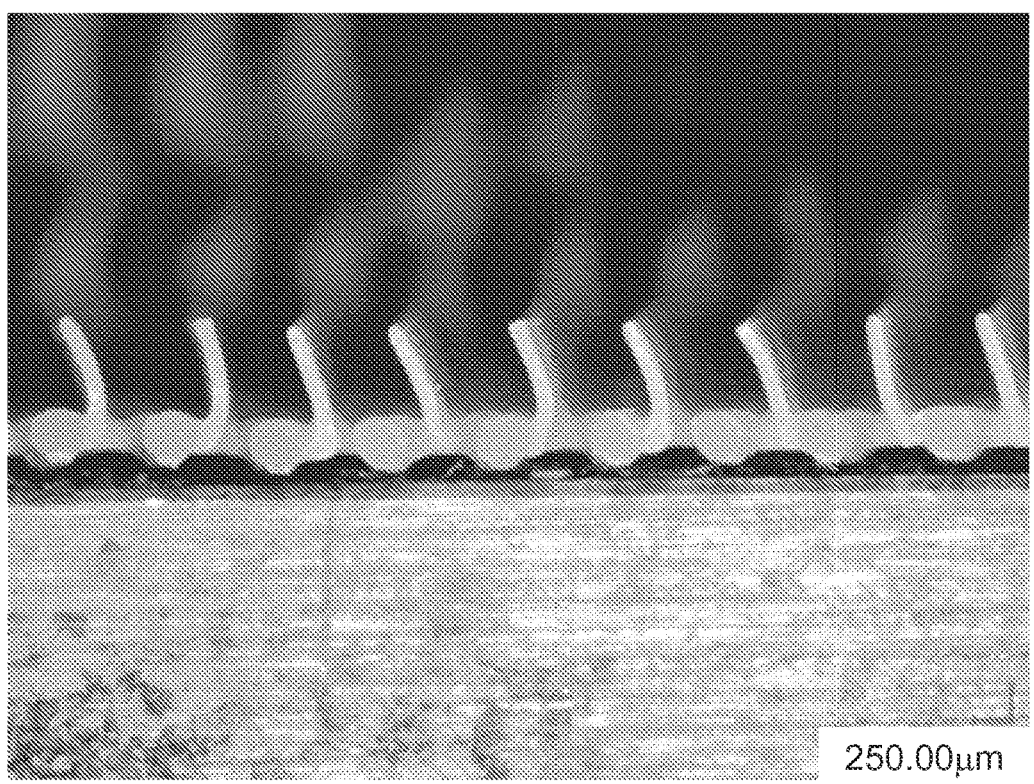
Figure 35:
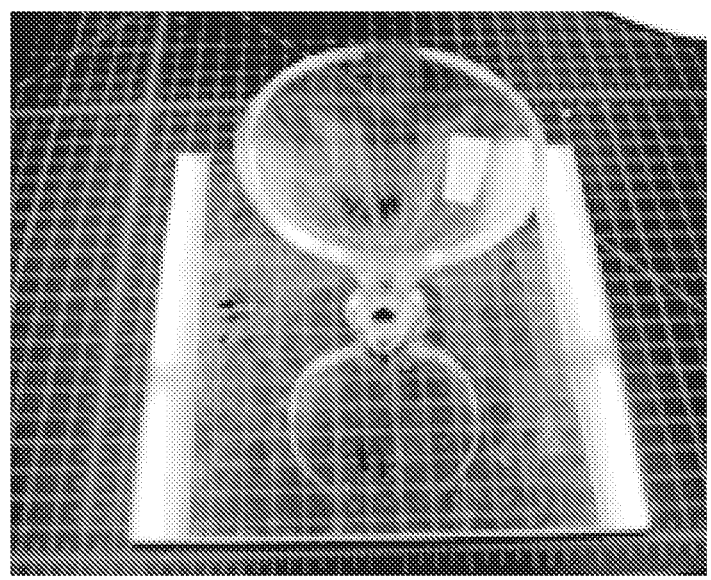
FIG. 35 is a photograph of a test jig used to evaluate the fluid strike-through time for Examples 1, 1b, 4a, 4b, 6a, and 6b.

Photographs of the polymeric netting obtained are shown in FIGS. 34A and 34B. Using an optical microscope at 30× magnification, the polymeric strand width and height were determined to be 350 micrometers and 360 micrometers respectively, and the polymeric ribbon width and height were determined to be 110 micrometers and 925 micrometers, respectively. The basis weight of the polymeric netting was measured as described in Example 1 and found to be 240 g/m², and its overall caliper was 925 micrometers.

Example 6a

The top sheet was removed from a 270 mm by 90 mm pad obtained from First Quality Retail Services under the trade designation "OPTIONS ULTRA THINS", and the top sheet was replaced with a piece of the polymeric netting prepared in Example 6. The piece of the polymeric netting had dimensions of approximately 260 mm by 90 mm. The polymeric netting was placed on top of the acquisition/distribution layer without adhesive.

Example 6b

A piece of the polymeric netting made as described in Example 6 (approximately 260 mm by 90 mm) was soaked in a solution made from 90 grams of water and 10 grams of surfactant obtained from Dow Chemical Company under the trade designation "TRITON X-100", removed from the solution, and dried as described in Example 1b. The top sheet was removed from a 270 mm by 90 mm pad obtained from First Quality Retail Services under the trade designation "OPTIONS ULTRA THINS", and the top sheet was replaced with the soaked and dried polymeric netting. The polymeric netting was placed on top of the acquisition/distribution layer without adhesive.

Example 6c

The top sheet was removed from a 270 mm by 90 mm pad obtained from First Quality Retail Services under the trade designation "OPTIONS ULTRA THINS", and the acquisition/distribution was removed and replaced with a piece of the polymeric netting made as described in Example 6. The piece of the polymeric netting had dimensions of approximately 165 mm by 50 mm. The polymeric netting was placed on top of the absorbent without adhesive, and the original topsheet was positioned on top of the polymeric netting without adhesive.

Comparative Example A

Comparative Example A was an unmodified 270 mm by 90 mm pad obtained from First Quality Retail Services under the trade designation "OPTIONS ULTRA THINS".

Comparative Example B

Comparative Example B was a 270 mm by 90 mm pad obtained from First Quality Retail Services under the trade designation "OPTIONS ULTRA THINS" in which the topsheet had been removed and replaced.

Test Methods

Strike-Through Time:

The strike through time was measured using a test jig shown in FIG. 19. The jig was made of a poly(methyl methacrylate) sheet and had a dimension of 203 mm by 203 mm by 5 mm. A glass funnel with 15-mm diameter circular opening at the bottom was fit into a complimentary opening in the poly(methyl methacrylate) sheet, and the funnel was sealed into the opening with wax. Comparative Examples A and B and the Examples were each individually placed between the test jig and a poly(methyl methacrylate) sheet having a dimension of 203 mm by 203 mm by 5 mm having no opening. The opening in the test jig was placed approximately over the center of the pad. Four 250-gram weights were placed on top of the poly(methyl methacrylate) sheet, one in each of the four corners, which provided a 572 Pa (0.083 psi) force onto the pad. The bottom of the funnel was in contact with the pad. A volume of 20 mL of 0.9% NaCl aqueous solution including a small amount of red dye obtained from Aldrich Chemical Company, Milwaukee, Wis., under the trade designation "DIRECT RED 81" was poured through the funnel. The strike-through time was measured with a stopwatch in seconds from the time the solution was poured into the funnel and the time the funnel was totally empty. One sample was tested for each Example and Comparative Example.

Rewet:

The test jig was removed from the pad at the end of the Strike-through Time evaluation, and the pad was allowed to stand for five minutes after the solution was applied. Ten pieces of pre-weighed VWR filter paper #110 (11 cm circle) were then applied on the top of the pad in the center in a stack, and a 152 mm by 78 mm weight (1967.2 grams) was placed on top of the filter paper for three minutes. The weight was removed, and the pieces of filter paper were reweighed. The rewet in grams was recorded as the weight gain on the pieces of filter paper.

Fluid Distribution:

After the weight was removed from the sample in the Rewet evaluation, the distance that the solution traveled along the pad lengthwise and widthwise was measured using a ruler.

The Strike-Through Time, Rewet, and Fluid Distribution length and width for each of Comparative Examples A and B and Examples 1, 1b, 1c, 4a, 4b, 4c, 6a, 6b, and 6c are reported in Table 1, below.

TABLE 1

| Example | Strike-Through Time (seconds) | Rewet (grams) | Fluid Distribution Length (mm) | Fluid Distribution Width (mm) |
|---|---|---|---|---|
| Comp. Ex. A | 7.8 | 0.046 | 115 | 65 |
| Comp. Ex. B | 5.3 | 0.702 | 100 | 70 |
| Example 1 | 5.3 | 0.024 | 120 | 65 |
| Example 1b | 3.5 | 0.034 | 130 | 65 |
| Example 6a | 4.5 | 0.024 | 130 | 65 |
| Example 6b | 4.6 | 0.022 | 135 | 65 |
| Example 4a | 2.3 | 1.655[a] | 150 | 65 |
| Example 4b | 1.6 | 0.163 | 180 | 50 |
| Example 1c | 7.4 | 0.369[b] | 110 | 65 |
| Example 6c | 6.3 | 0.564[b] | 150 | 65 |
| Example 4c | 2.4 | 0.708[b] | 190 | 50 |

[a]The liquid did not go through the netting, so the rewet value is higher.
[b]It is believed that the disruption of the pad created air gaps and SAP contamination on the topsheet to cause higher rewet values.

Respirator Examples

Recovery

The recovery times of three different examples of polymeric nettings were determined. Each sample was placed in a TA Instruments Q800 Dynamic Mechanical Analyzer set in Creep mode. And the following standardized test procedures were utilized: ASTM D-4065 Determining and Reporting Dynamic Mechanical Properties of Plastics; ASTM D-4092 Standard Terminology to Dynamic Mechanical Measurements on Plastics; and ASTM E-473 Terminology Relating to Thermal Analysis. During testing, a sample of uniform geometry was placed under a small initial stress for a period of time. The stress was then removed and material recovery was measured for a set period of time. Each sample was placed between parallel plates of 15 mm and 40 mm in diameter respectively. A 5 kilo Pascal stress was provided to the sample for 1 minute followed by a two-minute recovery under no stress.

Example 7

A co-extrusion die as generally depicted in FIGS. 22 and 23 and assembled with a multi shim repeating pattern of extrusion orifices as generally illustrated in FIGS. 12A and 12B was prepared. The thickness of the shims in the repeat sequence was 4 mils (0.102 mm). These shims were formed from stainless steel, with perforations cut by a wire electron discharge machining Referring to FIG. 11, the height of dispensing orifices 356 of shims 300 were cut to 100 mils (2.54 mm). Referring to FIG. 9, the height of the dispensing orifice 156 of shims 100 were cut to 20 mils (0.508 mm). The shims were stacked in a repeating sequence 100, 100, 200, 200, 300, 300, 200, 200. As assembled the width of the dispensing openings 1001 and 1003 were each 0.203 mm, and the land spacings between openings were 0.203 mm. The extrusion orifices were aligned in a collinear, alternating arrangement, and resulting dispensing surface was as shown in FIG. 12B. The total width of the shim setup was about 13 cm. (5 inches)

The inlet fittings on the two end blocks were each connected to three conventional single-screw extruders. Each extruder feeding cavities 1012a and 1012c were loaded with styrene-ethylene/butylene-styrene block copolymer elastomer (obtained under the trade designation "1643" from Kraton, Belpre, Ohio) dry blended with 3% orange or blue colorant masterbatch, respectively, (orange and blue obtained under the trade designation "Orange PP" and "Blue PP" from Clariant, Minneapolis, Minn.).

The flow rate of the polymer exiting openings 1003 was 1.4 kg/hr, and flow rate of the polymer exiting openings 1001 was 1.8 kg/hr. The melt was extruded vertically into an extrusion quench takeaway. The quench takeaway speed was 0.75 m/min, and the melt drop distance was 3 cm. The extrusion temperature was 204° C. The polymer exiting openings 1003 was oscillating. The quench roll was a smooth temperature controlled chrome plated 20-cm diameter steel roll. The quench temperature, which was 10° C., was controlled with internal water flow. The web path wrapped 180 degrees around the chrome steel roll and then to a windup roll.

Using an optical microscope at 30× magnification, the polymeric strand width and height were determined to be 145 micrometers and 597 micrometers respectively, and the polymeric ribbon width and height were determined to be 168 micrometers and 1943 micrometers, respectively. The basis weight of the polymeric netting was measured by weighing three 2 inch by 10 inch (5.1 cm by 25.4 cm) pieces of the netting with an analytical balance and averaging the values. The basis weight of the polymeric netting was found to be 544 g/m², and its overall caliper was 1943 micrometers.

Example 8

A co-extrusion die as generally depicted in FIGS. 22 and 23 and assembled with a multi shim repeating pattern of extrusion orifices as generally illustrated in FIGS. 12A and 12B was prepared. The thickness of the shims in the repeat sequence was 4 mils (0.102 mm). These shims were formed from stainless steel, with perforations cut by a wire electron discharge machining Referring to FIG. 11, the height of dispensing orifices 356 of shims 300 were cut to 100 mils (2.54 mm). Referring to FIG. 9, the height of the dispensing orifice 156 of shims 100 were cut to 20 mils (0.508 mm). The shims were stacked in a repeating sequence 100, 100, 200, 200, 300, 300, 200, 200. As assembled the width of the dispensing openings 1001 and 1003 were each 0.203 mm, and the land spacings between openings were 0.203 mm. The extrusion orifices were aligned in a collinear, alternating arrangement, and resulting dispensing surface was as shown in FIG. 12B. The total width of the shim setup was about 13 cm. (5 inches)

The inlet fittings on the two end blocks were each connected to three conventional single-screw extruders. Each extruder feeding cavities 1012a and 1012c were loaded with styrene-ethylene/butylene-styrene block copolymer elastomer (obtained under the trade designation "1645" from Kraton, Belpre, Ohio) dry blended with 3% black or green colorant masterbatch, respectively, (black and green obtained under the trade designation "Black PP" and "Green PP" from Clariant, Minneapolis, Minn.).

The flow rate of the polymer exiting openings 1003 was 1.4 kg/hr, and flow rate of the polymer exiting openings 1001 was 1.8 kg/hr. The melt was extruded vertically into an extrusion quench takeaway. The quench takeaway speed was 0.75 m/min, and the melt drop distance was 3 cm. The extrusion temperature was 232° C. The polymer exiting openings 1003 was oscillating. The quench roll was a smooth temperature controlled chrome plated 20-cm diameter steel roll. The quench temperature, which was 10° C., was controlled with internal water flow. The web path wrapped 180 degrees around the chrome steel roll and then to a windup roll.

Using an optical microscope at 30× magnification, the polymeric strand width and height were determined to be 228 micrometers and 546 micrometers respectively, and the polymeric ribbon width and height were determined to be 135 micrometers and 1537 micrometers, respectively. The basis weight of the polymeric netting was measured by weighing three 2 inch by 10 inch (5.1 cm by 25.4 cm) pieces of the netting with an analytical balance and averaging the values. The basis weight of the polymeric netting was found to be 527 g/m², and its overall caliper was 1537 micrometers.

Example 9

A co-extrusion die as generally depicted in FIGS. 22 and 23 and assembled with a multi shim repeating pattern of extrusion orifices as generally illustrated in FIGS. 12A and 12B was prepared. The thickness of the shims in the repeat sequence was 4 mils (0.102 mm). These shims were formed from stainless steel, with perforations cut by a wire electron discharge machining Referring to FIG. 11, the height of dispensing orifices 356 of shims 300 were cut to 100 mils (2.54 mm). Referring to FIG. 9, the height of the dispensing orifice 156 of shims 100 were cut to 20 mils (0.508 mm). The shims were stacked in a repeating sequence 100, 100, 200, 200, 300, 300, 200, 200. As assembled the width of the dispensing openings 1001 and 1003 were each 0.203 mm, and the land spacings between openings were 0.203 mm. The extrusion orifices were aligned in a collinear, alternating arrangement, and resulting dispensing surface was as shown in FIG. 12B. The total width of the shim setup was about 13 cm. (5 inches)

The inlet fittings on the two end blocks were each connected to three conventional single-screw extruders. Each extruder feeding cavities 1012a and 1012c were loaded with styrene-ethylene/butylene-styrene block copolymer elastomer (obtained under the trade designation "MD 6843" from Kraton, Belpre, Ohio) dry blended with 3% black or red colorant masterbatch, respectively, (black and red obtained under the trade designation "Black PP" and "Red PP" from Clariant, Minneapolis, Minn.).

The flow rate of the polymer exiting openings 1003 was 1.4 kg/hr, and flow rate of the polymer exiting openings 1001 was 1.8 kg/hr. The melt was extruded vertically into an extrusion quench takeaway. The quench takeaway speed was 0.75 m/min, and the melt drop distance was 3 cm. The extrusion temperature was 260° C. The polymer exiting openings 1003 was oscillating. The quench roll was a smooth temperature controlled chrome plated 20-cm diameter steel roll. The quench temperature, which was 10° C., was controlled with internal water flow. The web path wrapped 180 degrees around the chrome steel roll and then to a windup roll.

Using an optical microscope at 30× magnification, the polymeric strand width and height were determined to be 241 micrometers and 609 micrometers respectively, and the polymeric ribbon width and height were determined to be 165 micrometers and 2108 micrometers, respectively. The basis weight of the polymeric netting was measured by weighing three 2 inch by 10 inch (5.1 cm by 25.4 cm) pieces of the netting with an analytical balance and averaging the values. The basis weight of the polymeric netting was found to be 381 g/m², and its overall caliper was 2108 micrometers.

Comparative Example C

Comparative Example C was an unmodified polyurethane-ester LC 165-33 foam available from Foamex (Media, Pa.).

Comparative Example D

Comparative Example D was an unmodified Nolutex™ polyurethane foam available from Filtrona Porous Technologies (Colonial Heights, Va.).

Results

Figure 43:
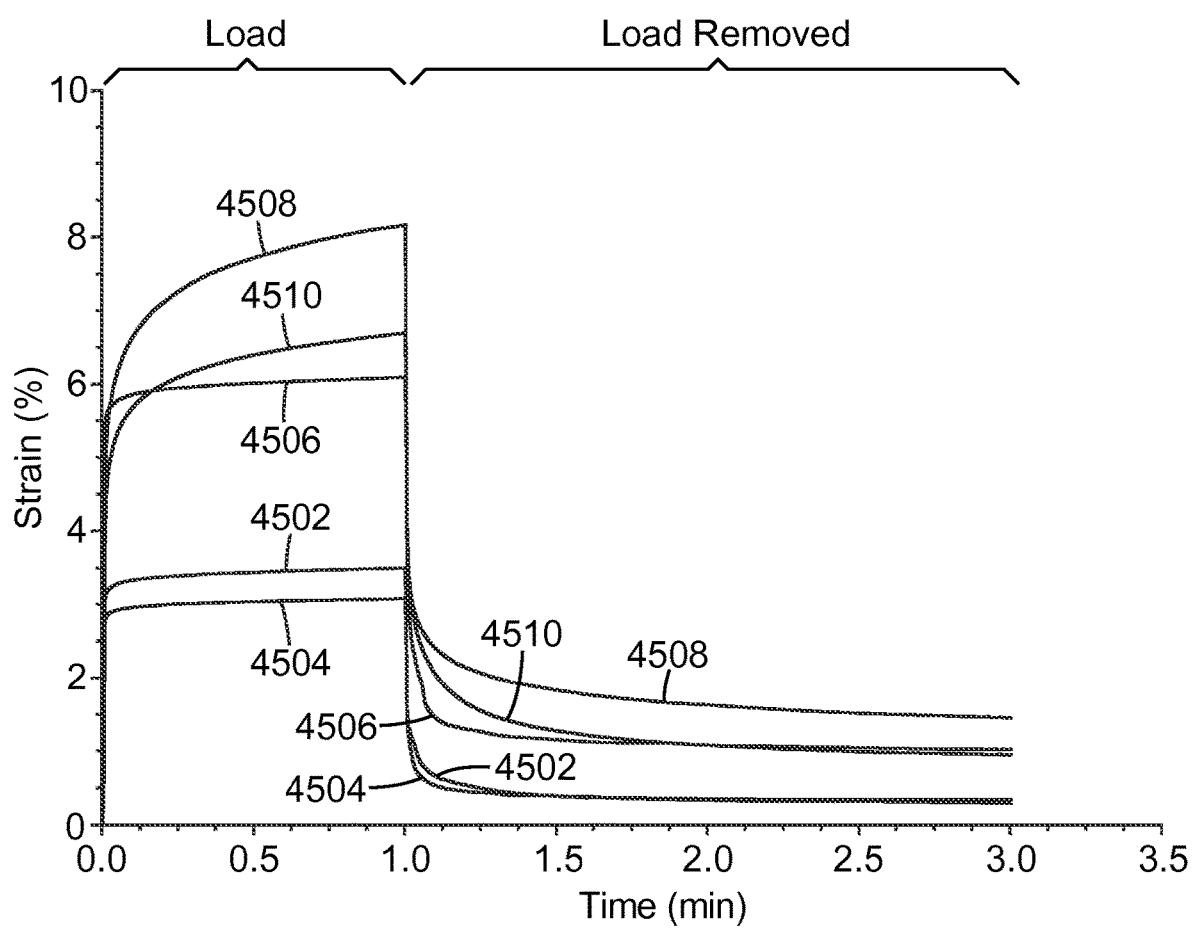
FIG. 43 is a graph of percent strain versus time for several examples of polymeric netting compared to polyurethane ester foam and polyurethane foam.

FIG. 43 is a graph of percent strain versus time for Examples 7-9 of polymeric netting compared to Comparative Examples C and D. Curve 4502 represents Example 9, curve 4504 represents Example 7, and curve 4506 represents Example 8. Further, curve 4508 represents Comparative Example C and curve 4510 represents Comparative Example D.

As can be seen in FIG. 43, the comparative foam examples exhibited a much greater % strain under the 5 kilo Pascal load than the polymeric netting examples. Further, when the load was removed at 1 minute, the foam examples had a much longer deformation recovery time than the polymeric netting examples. In general, the polymeric netting Examples 7-9 developed and recovered from deformation more quickly than the comparative foam examples C-D.

All references and publications cited herein are expressly incorporated herein by reference in their entirety into this disclosure, except to the extent they may directly contradict this disclosure. Illustrative embodiments of this disclosure are discussed and reference has been made to possible variations within the scope of this disclosure. These and other variations and modifications in the disclosure will be apparent to those skilled in the art without departing from the scope of the disclosure, and it should be understood that this disclosure is not limited to the illustrative embodiments set forth herein. Accordingly, the disclosure is to be limited only by the claims provided below.

What is claimed is:

1. A respirator comprising:
a mask body comprising a perimeter;
a harness attached to the mask body; and
a face seal disposed adjacent at least a portion of the perimeter of the mask body, wherein the face seal comprises a polymeric netting comprising polymeric ribbons and polymeric strands, each of the polymeric ribbons and strands having a length, width, and height, wherein the length is the longest dimension, the width is the shortest dimension, and the height is the dimension transverse to the length and the width, wherein the polymeric ribbons have a height-to-width aspect ratio of at least 5 to 1, a major surface that is intermittently bonded to only one polymeric strand, and a height that is at least two times greater than a height of the one polymeric strand.

2. The respirator of claim 1, wherein the polymeric ribbons each have a center line bisecting the major surface and first and second edges symmetrically disposed on opposite sides of the center line, wherein the major surface is intermittently bonded to only one polymeric strand at a location closer to the first edge than the second edge.

3. The respirator of claim 2, wherein the first edges of the polymeric ribbons comprise a different composition than the second edges of the polymeric ribbons.

4. The respirator of claim 1, wherein the polymeric netting comprises a percent recovery of at least 90%.

5. The respirator of claim 4, wherein the polymeric netting comprises a percent recovery of at least 98%.

6. The respirator of claim 1, wherein the polymeric ribbons comprise an average height and the polymeric strands comprise an average height, and wherein a ratio of the average height of the polymeric ribbons to the a.verag eight of the polymeric strands is at least 2 to 1.

7. The respirator of claim 6, wherein the ratio of the average height of the polymeric ribbons to the average height of the polymeric strands is at least 3 to 1.

8. The respirator of claim 1, wherein the polymeric ribbons each have a center line bisecting the major surface, and wherein the major surface is intermittently bonded to only one polymeric strand at a location including the center line.

9. The respirator of claim 1, wherein the polymeric ribbons and polymeric strands alternate in at least a portion of the polymeric netting.

10. The respirator of claim 1, wherein the face seal is disposed adjacent an upper perimeter segment of the mask body and is configured to contact a nose of a wearer.

11. The respirator of claim 1, wherein the face seal is disposed adjacent the entire perimeter of the mask body.

12. The respirator of claim 1, wherein the polymeric netting comprises a deformation recovery time of less than 60 seconds.

13. The respirator of claim 1, wherein the respirator comprises a filtering face-piece respirator.

14. The respirator of claim 1, wherein the respirator comprises a flat-fold respirator.

15. The respirator of claim 1, wherein the polymeric ribbons of the polymeric netting comprise a first polymer and the polymeric strands of the polymeric netting comprise a second polymer different from the first polymer.

* * * * *